United States Patent
Takeda et al.

(10) Patent No.: US 11,034,659 B2
(45) Date of Patent: Jun. 15, 2021

(54) PYRIMIDINE DERIVATIVE

(71) Applicant: Daiichi Sankyo Company, Limited, Tokyo (JP)

(72) Inventors: Yasuyuki Takeda, Funabashi (JP); Yamato Suzuki, Shinagawa-ku (JP); Toshiharu Noji, Ota-ku (JP); Hidenobu Murafuji, Shinagawa-ku (JP); Satoshi Muneoka, Shinagawa-ku (JP); Hidekazu Inoue, Ota-ku (JP); Bitoku Takahashi, Shinagawa-ku (JP); Rie Inaba, Ota-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 56 days.

(21) Appl. No.: 16/473,749

(22) PCT Filed: Dec. 26, 2017

(86) PCT No.: PCT/JP2017/046504
§ 371 (c)(1),
(2) Date: Jun. 26, 2019

(87) PCT Pub. No.: WO2018/124000
PCT Pub. Date: Jul. 5, 2018

(65) Prior Publication Data
US 2020/0172494 A1 Jun. 4, 2020

(30) Foreign Application Priority Data
Dec. 27, 2016 (JP) .............................. JP2016-253857

(51) Int. Cl.
*A61K 31/506* (2006.01)
*A61K 31/505* (2006.01)
(Continued)

(52) U.S. Cl.
CPC ............ *C07D 239/34* (2013.01); *A61P 11/12* (2018.01); *C07B 2200/13* (2013.01)

(58) Field of Classification Search
CPC .. A61K 31/506; A61K 31/505; C07D 239/52; C07D 239/34
(Continued)

(56) References Cited

U.S. PATENT DOCUMENTS 6,169,104 B1 1/2001 Tusé et al.
2012/0172351 A1 7/2012 Negoro et al.

FOREIGN PATENT DOCUMENTS

JP 2001-518935 A 10/2001
JP 2012-529422 A 11/2012
(Continued)

OTHER PUBLICATIONS

Extended European Search Report dated Apr. 23, 2020, issued in European Application No. 17887642.1, filed on Dec. 26, 2017, 8 pages.
(Continued)

*Primary Examiner* — Joseph R Kosack
*Assistant Examiner* — Sagar Patel
(74) *Attorney, Agent, or Firm* — Christensen O'Connor Johnson Kindness PLLC

(57) ABSTRACT

Cystic fibrosis is developed through mutation of Cystic Fibrosis Transmembrane conductance Regulator (CFTR), which is one type of chloride channel. An object of the present invention is to provide compounds effective in the treatment of cystic fibrosis that open a chloride channel different from CFTR, which is the cause of the disease, and do not depend on CFTR.

Compounds of the present invention are compounds or pharmaceutically acceptable salts thereof that open calcium dependent chloride channels (CaCCs) via G-protein coupled receptor 39 (GPR39) agonism to have strong chloride ion-secretory action, and are represented by the following general formula (I):

General formula (I):

[Formula 1]

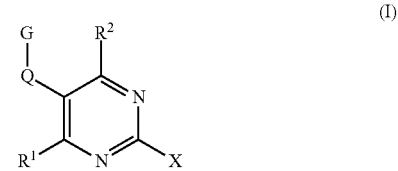

(I)

wherein,
X represents a carboxyl group or a tetrazolyl group;
Q represents a $C_1$-$C_3$ alkylene group, an oxygen atom, a sulfur atom, etc.;
G represents a phenyl group where the phenyl group may have 1 to 3 substituents independently selected from the group consisting of a halogen atom, a cyano group, a $C_1$-$C_6$ alkyl group, etc.;
$R^1$ represents a $C_1$-$C_6$ alkyl group, etc.;
$R^2$ represents a $C_1$-$C_6$ alkyl group that may have 1 to 3 substituents independently selected from the following group A, or a group selected from the following group B:
Group A: a phenyl group and a pyridyl group, wherein the phenyl group and the pyridyl group may have 1 to 3 substituents independently selected from the following group D;
Group B: —OH, —O-M, —SH, —S-M, —$NH_2$, —NH-M, and —N-$M_2$, wherein M is a $C_1$-$C_6$ alkyl group that may have 1 or 2 substituents independently selected from the following group C, or a $C_3$-$C_6$ cycloalkyl group that may have 1 or 2 substituents independently selected from the following group C;

(Continued)

Group C: a halogen atom, a cyano group, a phenyl group, a pyridyl group, etc., wherein the phenyl group and the pyridyl group may have 1 to 3 substituents independently selected from the following group D; and Group D: a halogen atom, a cyano group, a $C_1$-$C_6$ alkyl group, etc.

25 Claims, 7 Drawing Sheets

(51) Int. Cl.
    *C07D 239/52*     (2006.01)
    *C07D 239/34*     (2006.01)
    *A61P 11/12*     (2006.01)

(58) Field of Classification Search
    USPC .................................. 514/269; 544/335, 319
    See application file for complete search history.

(56) References Cited

FOREIGN PATENT DOCUMENTS

| WO | 2008/109178 A1 | 9/2008 | |
|---|---|---|---|
| WO | 2013/059648 A1 | 4/2013 | |
| WO | WO-2016140978 A1 * | 9/2016 | ........... C07D 213/79 |

OTHER PUBLICATIONS

Fjellström, O., et al., "Novel Zn2+ Modulated GPR39 Receptor Agonists Do Not Drive Acute Insulin Secretion in Rodents," PLOS One 10(12):e0145849, Dec. 2015, pp. 1-25.

International Search Report and Written Opinion dated Mar. 6, 2018, issued in corresponding International Application No. PCT/JP2017/046504, filed Dec. 26, 2017, 11 pages.

Moss, R.B., "Pitfalls of Drug Development: Lessons Learned From Trials of Denufosol in Cystic Fibrosis," Journal of Pediatrics 162(4):676-680, Apr. 2013.

Namkung W., et al., "Small-Molecule Activators of TMEM16A, a Calcium-Activated Chloride Channel, Stimulate Epithelial Chloride Secretion and Intestinal Contraction," FASEB Journal 25:4048-4062, Nov. 2011.

Peukert, S., et al., "Discovery of 2-Pyridylpyrimidines as the First Orally Bioavailable GPR39 Agonists," ACS Medicinal Chemistry Letters 5:1114-1118, 2014.

Ramsey, B.W., et al., "A CFTR Potentiator in Patients With Cystic Fibrosis and the G551D Mutation," New England Journal of Medicine 365(18):1663-1672, Nov. 2011.

Van Goor, F., et al., "Rescue of CF Airway Epithelial Cell Function In Vitro by a CFTR Potentiator, VX-770," Proceedings of the National Academy of Sciences of the USA (PNAS) 106(44):18825-18830, Nov. 2009.

Zeng F., et al., "GPR39 Is Coupled to TMEM16A in Intestinal Fibroblast-Like Cells," PLOS One 7(10):e47686, Oct. 2012, pp. 1-11.

* cited by examiner

[Figure 1]
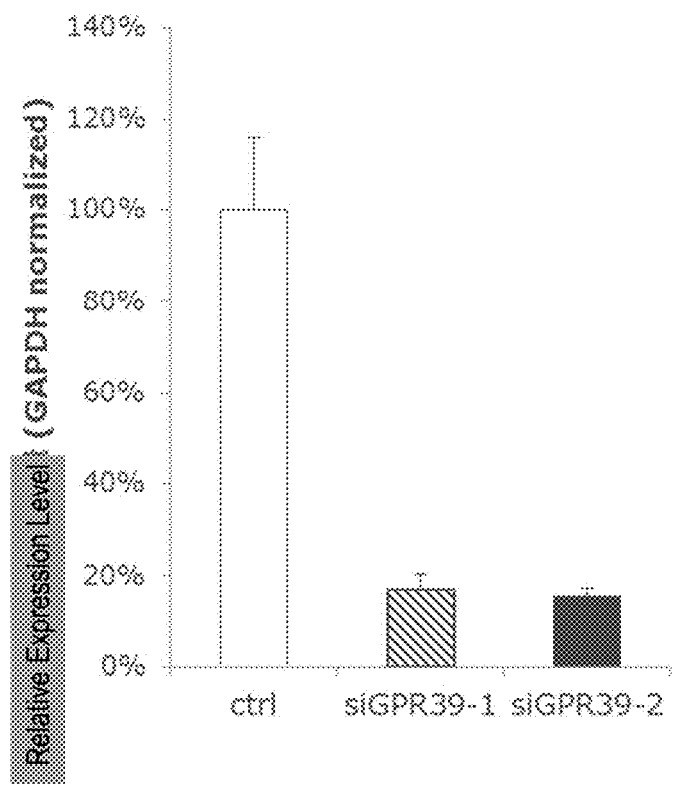
[Figure 2]
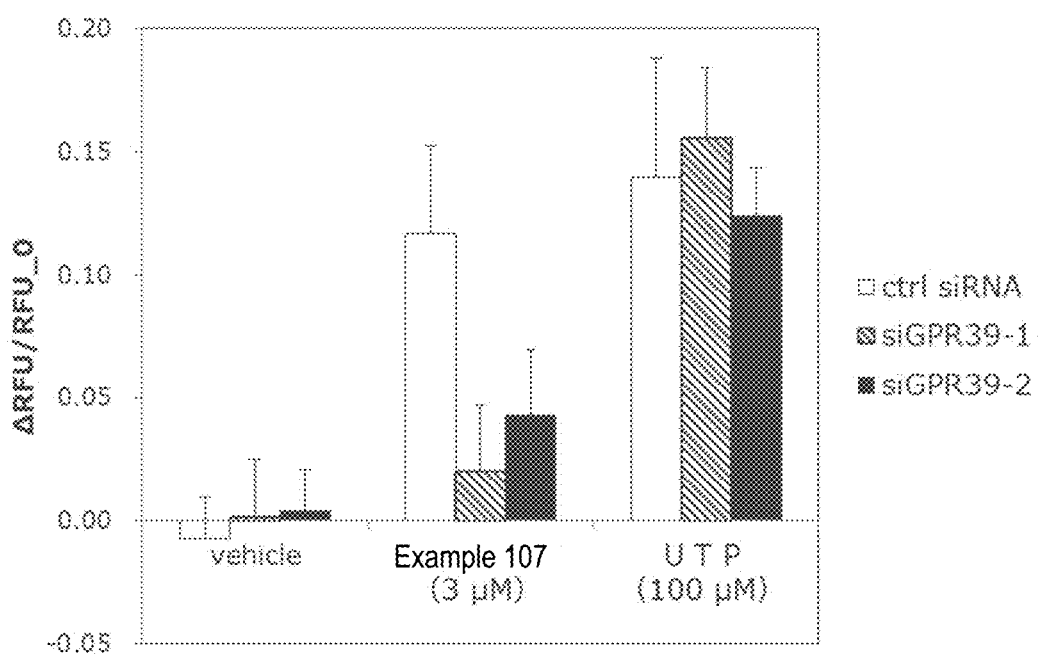

[Figure 3]
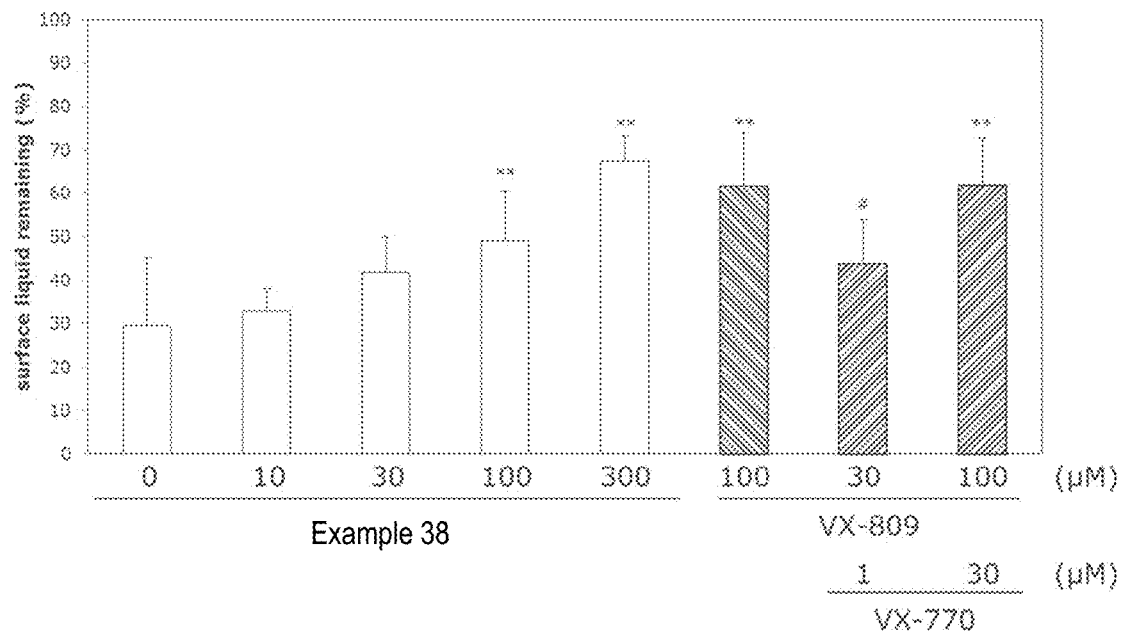
[Figure 4]
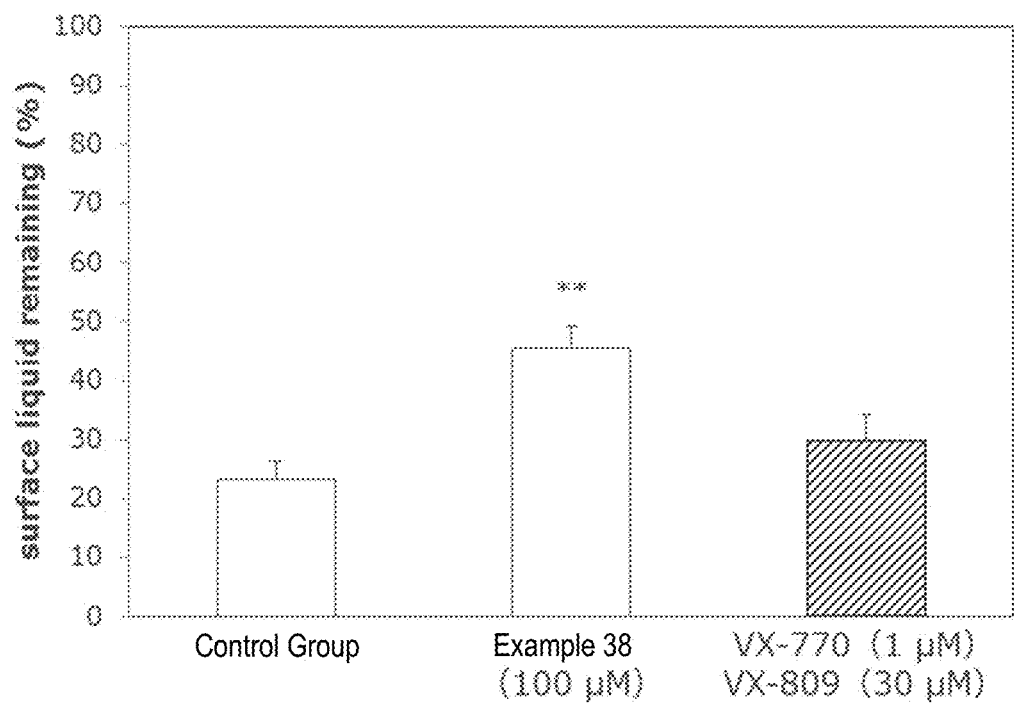

[Figure 5]
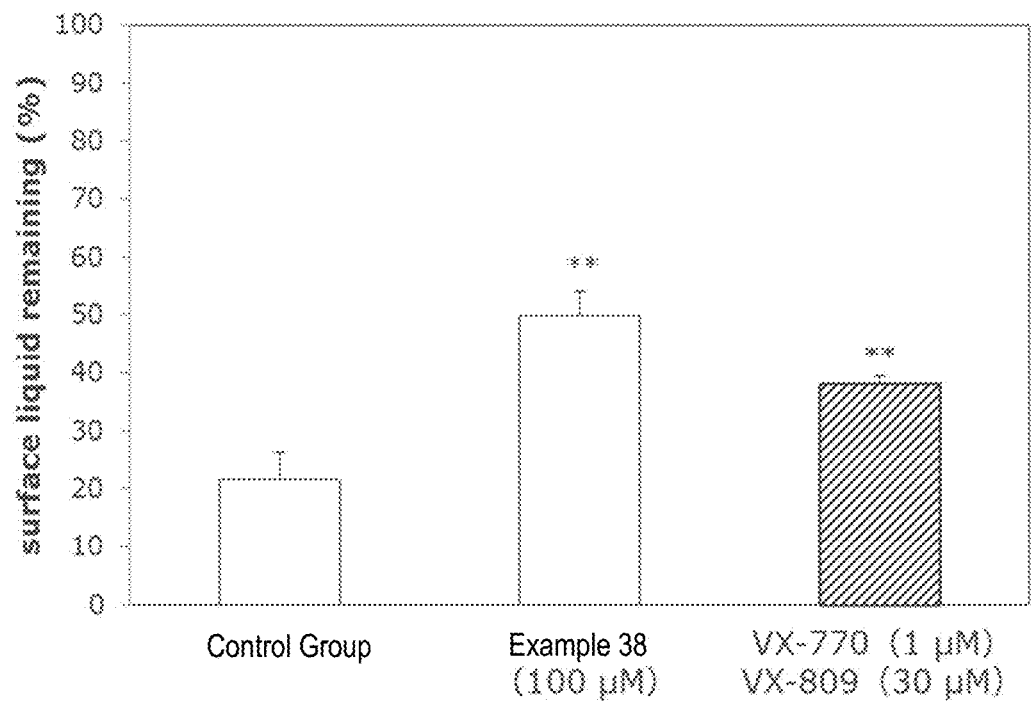
[Figure 6]
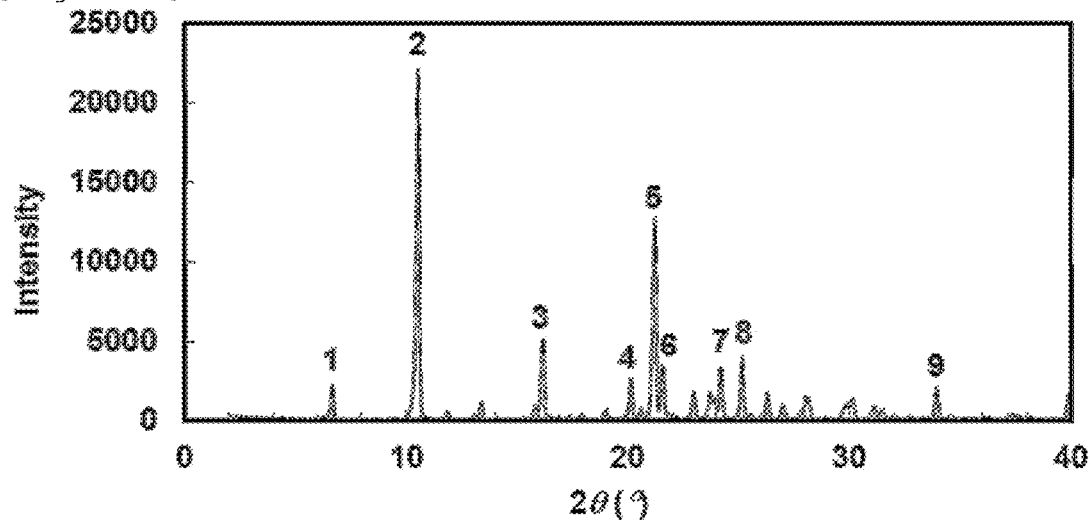

[Figure 7]
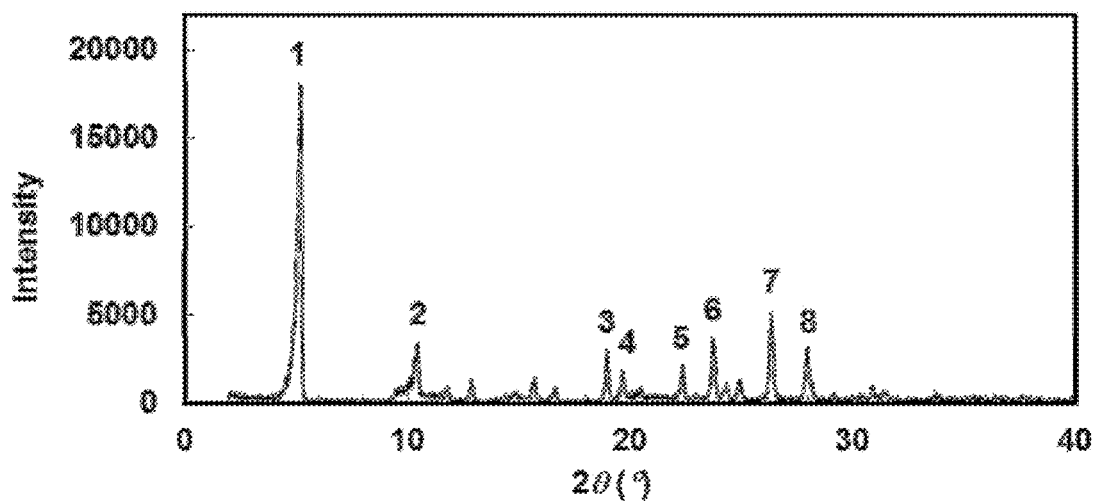
[Figure 8]
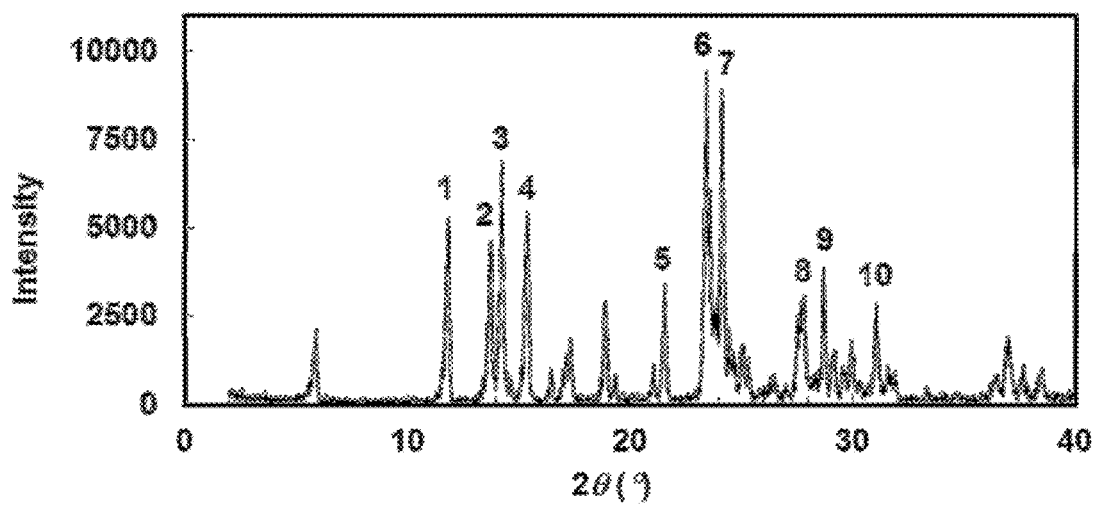

[Figure 9]
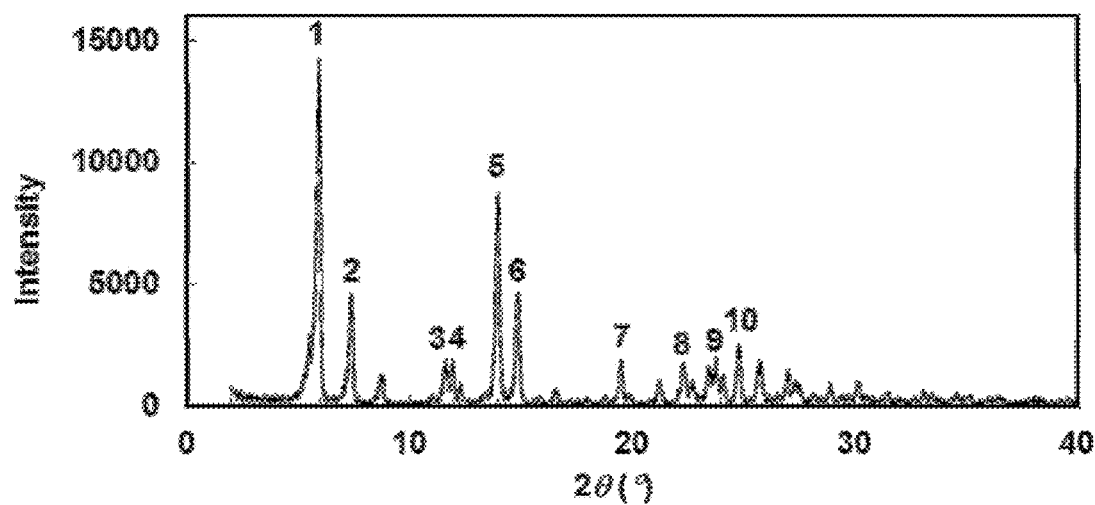
[Figure 10]
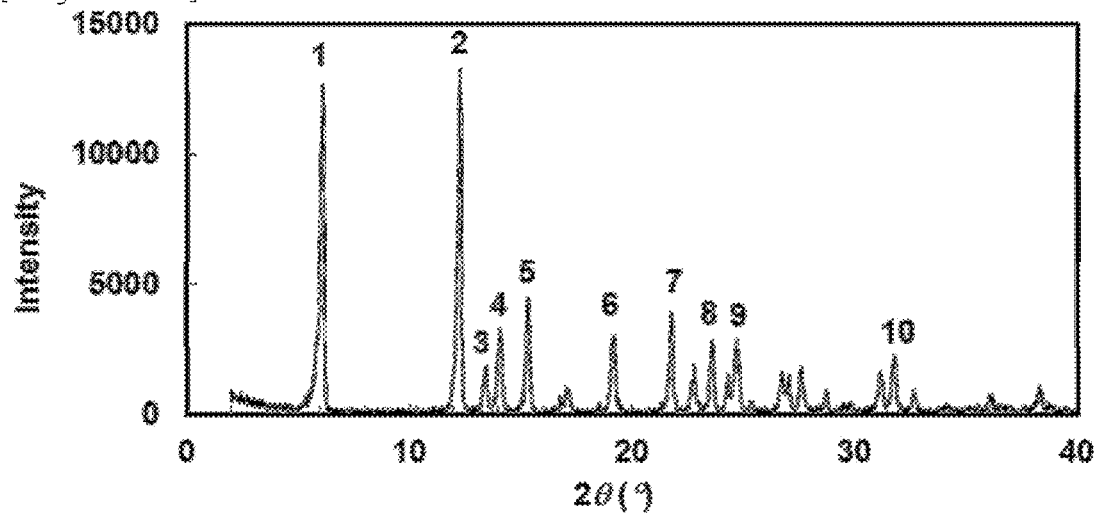

[Figure 11]
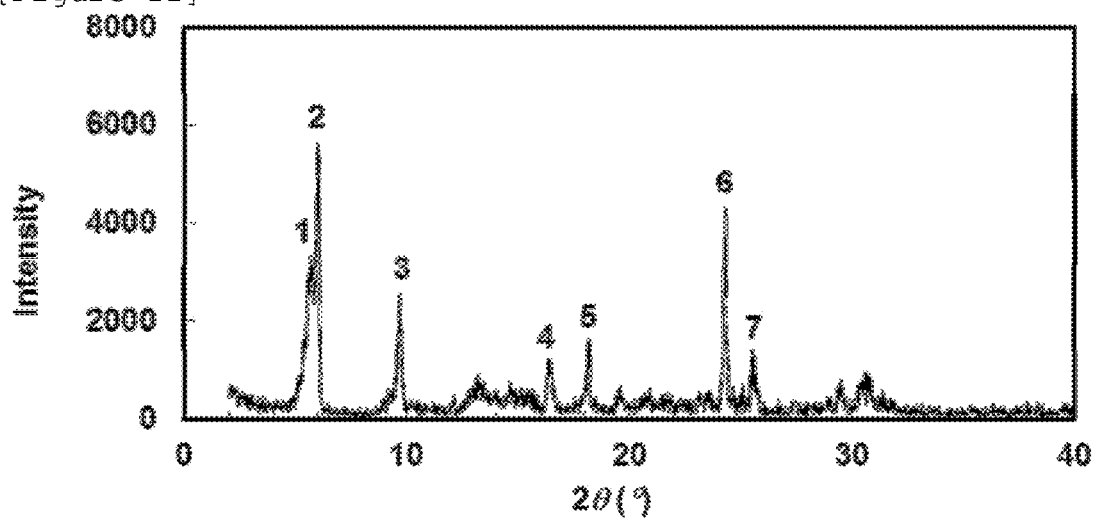
[Figure 12]
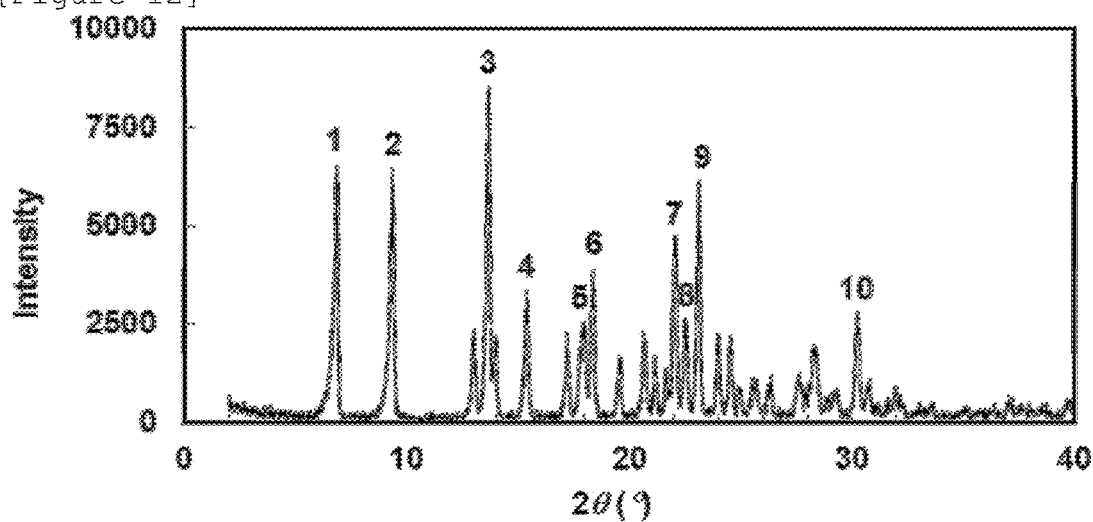

[Figure 13]
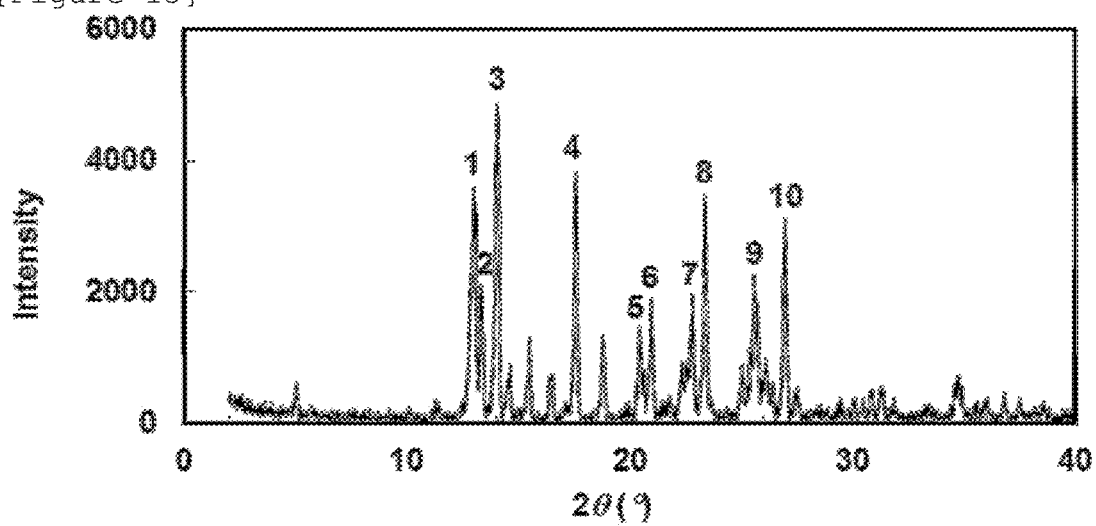

PYRIMIDINE DERIVATIVE

TECHNICAL FIELD

The present invention relates to compounds or pharmaceutically acceptable salts thereof which are useful as a therapeutic agent for cystic fibrosis, etc. that have excellent G protein-coupled receptor 39 (abbreviated as GPR39 herein) agonism and open a Calcium-activated Chloride Channel (abbreviated as CaCC herein) via activation of GPR39.

BACKGROUND ART

Cystic fibrosis is a severe genetic disease that is developed through genetic mutation of a Cystic Fibrosis Transmembrane conductance Regulator (abbreviated as CFTR herein), which is one type of chloride channel, and it is said that there are more than 70,000 patients throughout the world. Although development of treatment methods for the disease has been progressed recently, the average lifetime for those patients is still about 40 years, and no sufficiently satisfactory treatment method has been established at the current time.

CFTR is a major cAMP dependent anion channel that is expressed systemically on the lumen membrane of epithelial cells. When this channel decreases in function because of genetic mutation, transportation of ions and water via epithelial membrane/mucous membrane is disturbed in the respiratory tract, intestinal tract, pancreatic duct, bile duct, sweat duct, etc., and the mucus/secretory fluid in the lumen becomes unduly viscous, leading to the occurrence of lumen occlusion or a compromised host. Especially, disturbance in the lung is critical, and most of the cystic fibrosis patients die of tracheal obstruction or respiratory failure due to infection of the respiratory organ. Since CFTR was identified as the responsible gene for cystic fibrosis, research related to this disease has been advanced, and it has now been reported that there are approximately 1900 or more types of mutation associated with the disease. These mutations are categorized into six classes according to the type of CFTR dysfunction caused by the mutation (class I: nonsense mutation, class II: misfolding mutation of the protein, class III: mutation of abnormal channel opening, class IV: mutation of decreased channel conductance, class V: mutation of decreased CFTR production quantity, and class VI: mutation of decreased CFTR stability), and among them, class I, class II and class III mutations in particular, in which almost no chloride ions are secreted, bring about severe symptoms and have very high unmet medical needs.

Conventional treatments of cystic fibrosis have mainly focused on symptomatic therapy using ibuprofen or antimicrobial agents, but recently, Kalydeco® (ivacaftor (a CFTR potentiator)) and Orkambi® (a combination of ivacaftor (a CFTR potentiator) and lumacaftor (a CFTR corrector)), which act on CFTR directly and improve CFTR functions, have been launched on the market. However, Kalydeco has effects only on some of the patients with class III and class IV mutations, and Orkambi has effects only on ΔF508 homozygous mutation, among the class II mutations. Moreover, although a statistically significant improvement of respiratory functions has been confirmed for Orkambi, the efficacy is still limiting, and there are a large number of patients who have not received sufficient therapeutic agents, mainly with class I and class II mutations. As a method for solving these problems, mention can be made of opening chloride channels other than CFTR and having them compensate for the CFTR dysfunction. It is believed that acquisition of compounds with such a profile theoretically enables treatment of all cystic fibrosis patients independent of the type of CFTR mutation. Such an idea has so far led to development of Denufosol, which is a $P2Y_2$ (one type of G protein-coupled receptor (GPCR)) agonist, with a concept of having it open a Calcium-activated Chloride Channels (CaCC), which is a chloride channel different from CFTR. However, its development is now interrupted because of some reasons, such as Denufosol was unstable in the lung of patients (Non Patent Reference 1). It is also reported that low molecular weight compounds that directly act on and activate a CaCC have been screened and are promising as a therapeutic agent for cystic fibrosis (Non Patent Reference 2), but it is still uncertain whether those compounds display sufficient drug efficacy in a clinical situation. As explained above, since prior therapeutic agents of cystic fibrosis have effects only on some patients with limited mutations and the drug efficacy of Orkambi against ΔF508 homozygous mutation is not sufficient, further effective therapeutic agents are needed. The therapeutic concept for a compound that opens a chloride channel other than CFTR and compensates for the CFTR dysfunction has also been proposed already, but those displaying drug efficacy in clinical situations have not yet been found at the current time.

Since most cystic fibrosis patients die of tracheal obstruction or respiratory failure due to infection of the respiratory organ, it is important for a therapeutic agent for cystic fibrosis to have the possibility of being able to improve respiratory functions in a nonclinical drug efficacy evaluation. Meanwhile, since there is no animal model reflecting an inadequate pulmonary function of cystic fibrosis, in vitro drug efficacy evaluations are mainly conducted. For in vitro drug efficacy evaluations, a three-dimensional culturing system using airway epithelial cells derived from cystic fibrosis patients (Air-Liquid Interface assay; ALI assay) has been widely used as a system of evaluating drug efficacy since this system is similar to the pulmonary condition of cystic fibrosis patients in that the system rapidly absorbs moisture and hardly secretes moisture. Indeed, Kalydeco moves moisture in the ALI assay (Non Patent Reference 3), and as a result of development as a therapeutic agent of cystic fibrosis, its efficacy in clinical situations has been confirmed (Non Patent Reference 4).

GPR39 (G protein-coupled receptor 39) is a member of the ghrelin receptor family, and has been reported to express in the gastrointestinal tract, pancreas, liver, kidney, adipose tissue, thyroid gland, heart, lung, etc. Ligands for GPR39 have been unidentified for a long time, but there used to be a time when the ligand was presumed to be a peptide since GPR39 is a member of the ghrelin receptor family and obestatin was believed to be the natural ligand. However, in recent reports, it is said that obestatin is not a ligand of GPR39, but zinc ($Zn^{2+}$) is.

It has been reported that GPR39 is expressed in mouse intestinal fibroblast-like cells and activation of GPR39 is associated with activation of CaCCs (Non Patent Reference 5), but GPR39 functions in cells derived from cystic fibrosis patients are still unknown and there has been no report that a compound that is able to activate GPR39 and persistently open CaCCs has been found.

To date, AZ7914, AZ4237, AZ1395 (Non Patent Reference 6), a pyridylpyrimidine compound (Non Patent Reference 7), etc. have been reported as GPR39 agonists.

However, development of compounds with a novel structure that display excellent GPR39 agonism is still sought.

CITATION LIST

Non Patent References

Non Patent Reference 1: Journal of Pediatrics (J Pediatrics); 162(4): 676-80. (2013)
Non Patent Reference 2: FASEB Journal (FASEB J.); 25(11): 4048-62. (2011)
Non Patent Reference 3: Proceedings of the National Academy of Science of the United States of America (Proc Natl Acad Sci USA.); 106(44): 18825-30. (2009)
Non Patent Reference 4: The New England Journal of Medicine (N Engl J Med.); 365(18). (2011)
Non Patent Reference 5: PLoS ONE (PLoS One.); 7(10): e47686. (2012)
Non Patent Reference 6: PLOS ONE (PLOS ONE), Dec. 31, 2015
Non Patent Reference 7: ACS Medicinal Chemistry Letters (ACS Med. Chem. Lett.), 5, 1114-1118 (2014)

SUMMARY OF INVENTION

Technical Problem

The present inventors focused on the aspect that, in cystic fibrosis, which is developed through the CFTR mutation, by opening chloride channels different from CFTR, which is the cause of the disease, the CFTR dysfunction can be compensated for, leading to treatment. As a result of diligent studies, the present inventors have found that pyrimidine derivatives with a particular chemical structure open CaCCs via GPR39 agonism and are effective in treatment of cystic fibrosis without depending on CFTR, thereby completing the present invention.

Thus, according to the present invention, an ameliorating agent for cystic fibrosis that has a GPR39 agonist as the active component is provided.

Solution to Problem

The present invention is as follows.
(1) A compound represented by general formula (I):

[Formula 1]

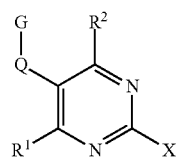
(I)

wherein,
X represents a carboxyl group or a tetrazolyl group;
Q represents a $C_1$-$C_3$ alkylene group, an oxygen atom, a sulfur atom, or $R^aN$, where
  $R^a$ represents a hydrogen atom or a $C_1$-$C_3$ alkyl group; G represents a phenyl group, where
  the phenyl group may have 1 to 3 substituents independently selected from the group consisting of a halogen atom, a cyano group, a $C_1$-$C_6$ alkyl group, a $C_1$-$C_3$ alkoxy group, and a trihalo $C_1$-$C_6$ alkyl group;

$R^1$ represents a $C_1$-$C_6$ alkyl group, a $C_1$-$C_3$ alkoxy $C_1$-$C_6$ alkyl group, or a $C_3$-$C_6$ cycloalkyl group; and
$R^2$ represents a $C_1$-$C_6$ alkyl group that may have 1 to 3 substituents independently selected from the following group A, or a group selected from the following group B, or a pharmaceutically acceptable salt thereof.
Group A: a phenyl group and a pyridyl group, wherein the phenyl group and the pyridyl group may have 1 to 3 substituents independently selected from the following group D;
Group B: —OH, —O-M, —SH, —S-M, —$NH_2$, —NH-M, and —N-$M_2$, wherein M is a $C_1$-$C_6$ alkyl group that may have 1 or 2 substituents independently selected from the following group C, or a $C_3$-$C_6$ cycloalkyl group that may have 1 or 2 substituents independently selected from the following group C;
Group C: a halogen atom, a hydroxy group, a cyano group, a carbamoyl group, a carboxyl group, a $C_1$-$C_6$ alkoxycarbonyl group, a $C_1$-$C_3$ alkoxy group, a phenyl group, and a pyridyl group,
wherein the phenyl group and the pyridyl group may have 1 to 3 substituents independently selected from the following group D; and
Group D: a halogen atom, a cyano group, a $C_1$-$C_6$ alkyl group, a $C_1$-$C_6$ alkoxy group, and a trihalo $C_1$-$C_6$ alkyl group.

In the present invention, mention may be preferably made of the following:
(2) A compound or a pharmaceutically acceptable salt thereof according to (1), wherein, in formula (I), X represents a carboxyl group.
(3) A compound or a pharmaceutically acceptable salt thereof according to (1) or (2), wherein, in formula (I), Q represents a methylene group, an oxygen atom, or a sulfur atom.
(4) A compound or a pharmaceutically acceptable salt thereof according to any one of (1) to (3), wherein, in formula (I), G is a phenyl group having 1 to 3 substituents independently selected from the group consisting of a chlorine atom, a fluorine atom, a cyano group, a $C_1$-$C_3$ alkyl group, a $C_1$-$C_3$ alkoxy group and a trihalomethyl group, or an unsubstituted phenyl group.
(5) A compound or a pharmaceutically acceptable salt thereof according to any one of (1) to (3), wherein, in formula (I), G is a phenyl group having 1 to 2 substituents independently selected from the group consisting of a chlorine atom and a fluorine atom.
(6) A compound or a pharmaceutically acceptable salt thereof according to any one of (1) to (5), wherein, in formula (I), $R^1$ represents a $C_1$-$C_6$ alkyl group.
(7) A compound or a pharmaceutically acceptable salt thereof according to any one of (1) to (6), wherein, in formula (I), $R^2$ is a $C_1$-$C_6$ alkyl group that may be substituted with one pyridyl group, or —O-M, —S-M, —NH-M, wherein M is a $C_1$-$C_6$ alkyl group that may have 1 or 2 substituents independently selected from the following group $C^1$, or a $C_3$-$C_6$ cycloalkyl group that may have one substituent independently selected from the following group $C^1$:
Group $C^1$: a halogen atom, a cyano group, a phenyl group, and a pyridyl group, wherein the phenyl group and the pyridyl group may have 1 to 3 substituents independently selected from the following group $D^1$; and
Group $D^1$: a halogen atom, a cyano group, a $C_1$-$C_6$ alkyl group.

(8) A compound or a pharmaceutically acceptable salt thereof according to any one of (1) to (7), wherein, in formula (I), Q represents a methylene group, an oxygen atom, or a sulfur atom;

G is a phenyl group having 1 to 2 substituents independently selected from the group consisting of a chlorine atom and a fluorine atom;

$R^1$ is a $C_1$-$C_3$ alkyl group; and $R^2$ is a $C_1$-$C_6$ alkyl group that may be substituted with one pyridyl group, or —O-M, —S-M, —NH-M, wherein M is a $C_1$-$C_6$ alkyl group that may have 1 or 2 substituents independently selected from the following group $C^1$, or a $C_3$-$C_6$ cycloalkyl group that may have one substituent independently selected from the following group $C^1$:

Group $C^1$: a halogen atom, a cyano group, a phenyl group, and a pyridyl group, wherein the phenyl group and the pyridyl group may have 1 to 3 substituents independently selected from the following group $D^1$; and Group $D^1$: a halogen atom, a cyano group, a $C_1$-$C_6$ alkyl group.

(9) A compound or a pharmaceutically acceptable salt thereof according to (1), wherein the compound is any one selected from the following group:

5-(2,4-dichlorobenzyl)-4-(ethylamino)-6-methylpyrimidine-2-carboxylic acid;
5-((2-chlorophenyl)thio)-4-(ethylamino)-6-methylpyrimidine-2-carboxylic acid;
5-(2-chlorobenzyl)-4-methoxy-6-methylpyrimidine-2-carboxylic acid;
5-(2-chlorobenzyl)-4-ethyl-6-methoxypyrimidine-2-carboxylic acid;
5-(2-chloro-3-fluorobenzyl)-4-ethyl-6-methoxypyrimidine-2-carboxylic acid;
5-(2-chlorobenzyl)-4-ethyl-6-(3-fluoropropoxy)pyrimidine-2-carboxylic acid;
5-(2,4-dichlorobenzyl)-4-methyl-6-(methylthio)pyrimidine-2-carboxylic acid;
4-(benzyloxy)-5-(2-chlorobenzyl)-6-methylpyrimidine-2-carboxylic acid;
5-(2-chlorobenzyl)-4-methyl-6-(pyridin-4-ylmethoxy)pyrimidine-2-carboxylic acid;
5-(2-chlorobenzyl)-4-methyl-6-(2-(pyridin-4-yl)ethyl)pyrimidine-2-carboxylic acid;
5-(2,4-dichlorophenoxy)-4-methyl-6-(methylamino)pyrimidine-2-carboxylic acid;
5-(2,4-dichlorobenzyl)-4-methoxy-6-methylpyrimidine-2-carboxylic acid;
5-(2,3-dichlorobenzyl)-4-ethyl-6-methoxypyrimidine-2-carboxylic acid;
5-(2-chlorobenzyl)-4-ethoxy-6-methylpyrimidine-2-carboxylic acid;
5-(2-chloro-3-fluorobenzyl)-4-ethoxy-6-ethylpyrimidine-2-carboxylic acid;
5-(2,3-dichlorobenzyl)-4-methoxy-6-methylpyrimidine-2-carboxylic acid;
5-(2-chlorobenzyl)-4-(cis-3-cyanocyclobutoxy)-6-methylpyrimidine-2-carboxylic acid;
5-(2,4-dichlorobenzyl)-4,6-dimethylpyrimidine-2-carboxylic acid; and
5-(2,4-dichlorobenzyl)-N,6-dimethyl-2-(1H-tetrazol-5-yl)pyrimidine-4-amine.

(10) A compound according to (1) or a pharmaceutically acceptable salt thereof, wherein the compound is any one selected from the following group:

5-(2,4-dichlorobenzyl)-4-(ethylamino)-6-methylpyrimidine-2-carboxylic acid;
5-((2-chlorophenyl)thio)-4-(ethylamino)-6-methylpyrimidine-2-carboxylic acid;
5-(2-chlorobenzyl)-4-methoxy-6-methylpyrimidine-2-carboxylic acid;
5-(2-chlorobenzyl)-4-ethyl-6-methoxypyrimidine-2-carboxylic acid;
5-(2-chloro-3-fluorobenzyl)-4-ethyl-6-methoxypyrimidine-2-carboxylic acid;
5-(2-chlorobenzyl)-4-ethyl-6-(3-fluoropropoxy)pyrimidine-2-carboxylic acid;
5-(2,4-dichlorobenzyl)-4-methyl-6-(methylthio)pyrimidine-2-carboxylic acid;
4-(benzyloxy)-5-(2-chlorobenzyl)-6-methylpyrimidine-2-carboxylic acid;
5-(2-chlorobenzyl)-4-methyl-6-(pyridin-4-ylmethoxy)pyrimidine-2-carboxylic acid; and
5-(2-chlorobenzyl)-4-methyl-6-(2-(pyridin-4-yl)ethyl)pyrimidine-2-carboxylic acid.

(11) A compound or a pharmaceutically acceptable salt thereof according to (1), wherein the compound is 5-(2-chlorobenzyl)-4-methoxy-6-methylpyrimidine-2-carboxylic acid.

(12) A compound or a pharmaceutically acceptable salt thereof according to (1), wherein the compound is 5-(2-chlorobenzyl)-4-ethyl-6-methoxypyrimidine-2-carboxylic acid.

(13) A compound or a pharmaceutically acceptable salt thereof according to any one of (1) to (12), wherein the pharmaceutically acceptable salt is a hydrochloride salt, a trifluoroacetate salt, a magnesium salt, a calcium salt, a zinc salt, a sodium salt, a tert-butylamine salt, or a diisopropylamine salt.

(14) A compound or a pharmaceutically acceptable salt thereof according to (1), wherein the compound or the pharmaceutically acceptable salt thereof is 5-(2-chlorobenzyl)-4-methoxy-6-methylpyrimidine-2-carboxylic acid, or a magnesium salt, a calcium salt, a zinc salt, a sodium salt, a tert-butylamine salt, or a diisopropylamine salt thereof.

(15) A compound or a pharmaceutically acceptable salt thereof according to (1), which is a bis[5-(2-chlorobenzyl)-4-methoxy-6-methylpyrimidine-2-carboxylic acid]magnesium salt having a crystal form having main peaks at diffraction angles 2θ=11.82, 13.74, 14.26, 15.38, 21.56, 23.42, 24.14, 27.82, 28.72, and 31.06 in a powder X-ray diffraction pattern obtained by irradiation with copper Kα radiation (wavelength λ=1.54 angstroms).

(16) A compound or a pharmaceutically acceptable salt thereof according to (1), which is a bis[5-(2-chlorobenzyl)-4-methoxy-6-methylpyrimidine-2-carboxylic acid]magnesium salt having a crystal form having main peaks at diffraction angles 2θ=5.18, 10.44, 18.98, 19.68, 22.36, 23.76, 26.34, and 27.96 in a powder X-ray diffraction pattern obtained by irradiation with copper Kα radiation (wavelength λ=1.54 angstroms).

(17) A compound or a pharmaceutically acceptable salt thereof according to (1), which is 5-(2-chlorobenzyl)-4-methoxy-6-methylpyrimidine-2-carboxylic acid having a crystal form having main peaks at diffraction angles 2θ=6.68, 10.54, 16.16, 20.16, 21.22, 21.58, 24.20, and 25.16, 33.92 in a powder X-ray diffraction pattern obtained by irradiation with copper Kα radiation (wavelength λ=1.54 angstroms).

(18) A pharmaceutical composition comprising a compound or a pharmaceutically acceptable salt thereof according to any one of (1) to (17).

(19) A pharmaceutical composition according to (18), for use in the treatment of cystic fibrosis.
(20) A compound or a pharmaceutically acceptable salt thereof according to any one of (1) to (17), for use in the treatment of cystic fibrosis.
(21) A method for treating cystic fibrosis comprising administering a pharmacologically effective amount of a compound or a pharmaceutically acceptable salt thereof according to any one of (1) to (17) to a warm-blooded animal.
(22) A method for treating according to (21), wherein the warm-blooded animal is a human.
(23) A pharmaceutical composition according to (18), wherein the pharmaceutical composition is for use in the prevention or treatment of a disease that is prevented or treated via G-protein coupled receptor 39 agonism.
(24) A pharmaceutical composition according to (23), wherein the disease is cystic fibrosis, non-CF bronchiectasis, primary ciliary dyskinesia, dry eye, constipation, adiposity, diabetes mellitus, ulcerative colitis, Crohn's disease, depression, or COPD.
(25) A pharmaceutical composition according to (18), wherein the pharmaceutical composition is for use in the prevention or treatment of a disease whose symptoms are prevented, ameliorated, or relieved by opening a calcium dependent chloride channel.
(26) A pharmaceutical composition according to (25), wherein the disease is cystic fibrosis, non-CF bronchiectasis, primary ciliary dyskinesia, dry eye, constipation, adiposity, diabetes mellitus, ulcerative colitis, Crohn's disease, depression, or COPD.

In addition, another aspect of the present invention is as follows.

(1a) A compound represented by general formula (I):

[Formula 2]

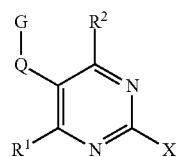

wherein,
X represents a carboxyl group or a tetrazolyl group;
Q represents a $C_1$-$C_3$ alkylene group, an oxygen atom, a sulfur atom, or $R^aN$, where
$R^a$ represents a hydrogen atom or a $C_1$-$C_3$ alkyl group; G represents a phenyl group, where
the phenyl group may have 1 to 3 substituents independently selected from the group consisting of a halogen atom, a cyano group, a $C_1$-$C_6$ alkyl group, a $C_1$-$C_3$ alkoxy group, and a trihalo $C_1$-$C_6$ alkyl group;
$R^1$ represents a $C_1$-$C_6$ alkyl group, a $C_1$-$C_3$ alkoxy $C_1$-$C_6$ alkyl group, or a $C_3$-$C_6$ cycloalkyl group; and
$R^2$ represents a $C_1$-$C_6$ alkyl group that may have 1 to 3 substituents independently selected from the following group A, or a group selected from the following group B, or a pharmaceutically acceptable salt thereof.
Group A: a phenyl group and a pyridyl group, wherein the phenyl group and the pyridyl group may have 1 to 3 substituents independently selected from the following group D;
Group B: —OH, —O-M, —SH, —S-M, —NH$_2$, —NH-M, and —N-M$_2$, wherein M is a $C_1$-$C_6$ alkyl group that may have 1 or 2 substituents independently selected from the following group C, or a $C_3$-$C_6$ cycloalkyl group that may have 1 or 2 substituents independently selected from the following group C;
Group C: a halogen atom, a hydroxy group, a cyano group, a carbamoyl group, a carboxyl group, a $C_1$-$C_6$ alkoxycarbonyl group, a $C_1$-$C_3$ alkoxy group, a phenyl group, and a pyridyl group,
wherein the phenyl group and the pyridyl group may have 1 to 3 substituents independently selected from the following group D; and
Group D: a halogen atom, a cyano group, a $C_1$-$C_6$ alkyl group, a $C_1$-$C_6$ alkoxy group, and a trihalo $C_1$-$C_6$ alkyl group.

(2a) A compound or a pharmaceutically acceptable salt thereof according to (1a), wherein, in formula (I), X represents a carboxyl group.
(3a) A compound or a pharmaceutically acceptable salt thereof according to (1a) or (2a), wherein, in formula (I), Q represents a methylene group, an oxygen atom, or a sulfur atom.
(4a) A compound or a pharmaceutically acceptable salt thereof according to any one of (1a) to (3a), wherein, in formula (I), G is a phenyl group having 1 to 3 substituents independently selected from the group consisting of a chlorine atom, a fluorine atom, a cyano group, a $C_1$-$C_3$ alkyl group, a $C_1$-$C_3$ alkoxy group and a trihalomethyl group, or an unsubstituted phenyl group.
(5a) A compound or a pharmaceutically acceptable salt thereof according to any one of (1a) to (3a), wherein, in formula (I), G is a phenyl group having 1 to 2 substituents independently selected from the group consisting of a chlorine atom and a fluorine atom.
(6a) A compound or a pharmaceutically acceptable salt thereof according to any one of (1a) to (5a), wherein, in formula (I), $R^1$ represents a $C_1$-$C_6$ alkyl group.
(7a) A compound or a pharmaceutically acceptable salt thereof according to any one of (1a) to (6a), wherein, in formula (I), $R^2$ is a $C_1$-$C_6$ alkyl group that may be substituted with one pyridyl group, or —O-M, —S-M, —NH-M,
wherein M is a $C_1$-$C_6$ alkyl group that may have 1 or 2 substituents independently selected from the following group $C^1$, or a $C_3$-$C_6$ cycloalkyl group that may have one substituent independently selected from the following group $C^1$:
Group $C^1$: a halogen atom, a cyano group, a phenyl group, and a pyridyl group,
wherein the phenyl group and the pyridyl group may have 1 to 3 substituents independently selected from the following group $D^1$; and
Group $D^1$: a halogen atom, a cyano group, a $C_1$-$C_6$ alkyl group.
(8a) A compound or a pharmaceutically acceptable salt thereof according to any one of (1a) to (7a), wherein, in formula (I), Q represents a methylene group, an oxygen atom, or a sulfur atom;
G is a phenyl group having 1 to 2 substituents independently selected from the group consisting of a chlorine atom and a fluorine atom;
$R^1$ is a $C_1$-$C_3$ alkyl group; and
$R^2$ is a $C_1$-$C_6$ alkyl group that may be substituted with one pyridyl group, or —O-M, —S-M, —NH-M, wherein M is a $C_1$-$C_6$ alkyl group that may have 1 or 2 substituents independently selected from the following group $C^1$, or a $C_3$-$C_6$ cycloalkyl group that may have one substituent independently selected from the following group $C^1$:

Group C¹: a halogen atom, a cyano group, a phenyl group, and a pyridyl group,
wherein the phenyl group and the pyridyl group may have 1 to 3 substituents independently selected from the following group D¹; and
Group D¹: a halogen atom, a cyano group, a $C_1$-$C_6$ alkyl group.
(9a) A compound or a pharmaceutically acceptable salt thereof, wherein the compound is any one selected from the following group:
5-(2,4-dichlorobenzyl)-4-(ethylamino)-6-methylpyrimidine-2-carboxylic acid;
5-((2-chlorophenyl)thio)-4-(ethylamino)-6-methylpyrimidine-2-carboxylic acid;
5-(2-chlorobenzyl)-4-methoxy-6-methylpyrimidine-2-carboxylic acid;
5-(2-chlorobenzyl)-4-ethyl-6-methoxypyrimidine-2-carboxylic acid;
5-(2-chloro-3-fluorobenzyl)-4-ethyl-6-methoxypyrimidine-2-carboxylic acid;
5-(2-chlorobenzyl)-4-ethyl-6-(3-fluoropropoxy)pyrimidine-2-carboxylic acid;
5-(2,4-dichlorobenzyl)-4-methyl-6-(methylthio)pyrimidine-2-carboxylic acid;
4-(benzyloxy)-5-(2-chlorobenzyl)-6-methylpyrimidine-2-carboxylic acid;
5-(2-chlorobenzyl)-4-methyl-6-(pyridin-4-ylmethoxy)pyrimidine-2-carboxylic acid;
5-(2-chlorobenzyl)-4-methyl-6-(2-(pyridin-4-yl)ethyl)pyrimidine-2-carboxylic acid;
5-(2,4-dichlorophenoxy)-4-methyl-6-(methylamino)pyrimidine-2-carboxylic acid;
5-(2,4-dichlorobenzyl)-4-methoxy-6-methylpyrimidine-2-carboxylic acid;
5-(2,3-dichlorobenzyl)-4-ethyl-6-methoxypyrimidine-2-carboxylic acid;
5-(2-chlorobenzyl)-4-ethoxy-6-methylpyrimidine-2-carboxylic acid;
5-(2-chloro-3-fluorobenzyl)-4-ethoxy-6-ethylpyrimidine-2-carboxylic acid;
5-(2,3-dichlorobenzyl)-4-methoxy-6-methylpyrimidine-2-carboxylic acid;
5-(2-chlorobenzyl)-4-(cis-3-cyanocyclobutoxy)-6-methylpyrimidine-2-carboxylic acid;
5-(2,4-dichlorobenzyl)-4,6-dimethylpyrimidine-2-carboxylic acid; and
5-(2,4-dichlorobenzyl)-N,6-dimethyl-2-(1H-tetrazol-5-yl)pyrimidine-4-amine.
(10a) 5-(2,4-Dichlorobenzyl)-4-(ethylamino)-6-methylpyrimidine-2-carboxylic acid or a pharmaceutically acceptable salt thereof.
(11a)
5-((2-Chlorophenyl)thio)-4-(ethylamino)-6-methylpyrimidine-2-carboxylic acid or a pharmaceutically acceptable salt thereof.
(12a)
5-(2-Chlorobenzyl)-4-methoxy-6-methylpyrimidine-2-carboxylic acid or a pharmaceutically acceptable salt thereof.
(13a)
5-(2-Chlorobenzyl)-4-ethyl-6-methoxypyrimidine-2-carboxylic acid or a pharmaceutically acceptable salt thereof.
(14a)
5-(2-Chloro-3-fluorobenzyl)-4-ethyl-6-methoxypyrimidine-2-carboxylic acid or a pharmaceutically acceptable salt thereof.
(15a)
5-(2-Chlorobenzyl)-4-ethyl-6-(3-fluoropropoxy)pyrimidine-2-carboxylic acid or a pharmaceutically acceptable salt thereof.
(16a)
5-(2,4-Dichlorobenzyl)-4-methyl-6-(methylthio)pyrimidine-2-carboxylic acid or a pharmaceutically acceptable salt thereof.
(17a)
4-(Benzyloxy)-5-(2-chlorobenzyl)-6-methylpyrimidine-2-carboxylic acid or a pharmaceutically acceptable salt thereof.
(18a)
5-(2-Chlorobenzyl)-4-methyl-6-(pyridin-4-ylmethoxy)pyrimidine-2-carboxylic acid or a pharmaceutically acceptable salt thereof.
(19a)
5-(2-Chlorobenzyl)-4-methyl-6-(2-(pyridin-4-yl)ethyl)pyrimidine-2-carboxylic acid or a pharmaceutically acceptable salt thereof.
(20a)
A pharmaceutical composition comprising a compound or a pharmaceutically acceptable salt thereof according to any one of (1a) to (19a).
(21a)
A pharmaceutical composition according to (20a) for use in the treatment of cystic fibrosis.
(22a)
A compound or a pharmaceutically acceptable salt thereof according to any one of (1a) to (19a) for use in the treatment of cystic fibrosis.
(23a)
A method for treating cystic fibrosis comprising administering a pharmacologically effective amount of a compound or a pharmaceutically acceptable salt thereof according to any one of (1a) to (19a) to a warm-blooded animal.

In the present invention, a "halogen atom" means a fluorine atom, a chlorine atom, a bromine atom, or an iodine atom. Preferably, the halogen atom is a chlorine atom or a bromine atom.

In the present invention, a "$C_1$-$C_6$ alkyl group" means a straight or branched alkyl group having 1 to 6 carbon atoms. Examples thereof include a methyl group, an ethyl group, a propyl group, an isopropyl group, a butyl group, an isobutyl group, an s-butyl group, a t-butyl group, a pentyl group, an isopentyl group, a 2-methylbutyl group, a neopentyl group, a 1-ethylpropyl group, a hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, and a 1,2-dimethylbutyl group. Straight or branched alkyl groups having 1 to 4 carbon atoms ($C_1$-$C_4$ alkyl groups) are preferred, a methyl group or an ethyl group ($C_1$-$C_2$ alkyl groups) is more preferred, and a methyl group (a $C_1$ alkyl group) is yet more preferred.

In the present invention, a "$C_1$-$C_3$ alkyl group" means a straight or branched alkyl group having 1 to 3 carbon atoms. Examples thereof include a methyl group, an ethyl group, a propyl group, and an isopropyl group. A methyl group or an ethyl group ($C_1$-$C_2$ alkyl groups) is preferred, and a methyl group (a $C_1$ alkyl group) is yet more preferred.

In the present invention, a "$C_3$-$C_6$ cycloalkyl group" means a cyclopropyl group, a cyclobutyl group, a cyclopentyl group, or a cyclohexyl group. A cyclohexyl group is preferred.

In the present invention, a "trihalo $C_1$-$C_6$ alkyl group" means a group in which three "halogen atoms," as described above, bind to the above described "$C_1$-$C_6$ alkyl group".

Examples thereof include a trifluoromethyl group, a trichloromethyl group, a 2,2,2-trifluoroethyl group, a 3,3,3-trifluoropropyl group, and a 2,2,2-trichloroethyl group. Groups in which three "halogen atoms" that are identical to or different from each other bind to the above described "$C_1$-$C_2$ alkyl group" (trihalo $C_1$-$C_2$ alkyl groups) are preferred, trihalomethyl groups (trihalo $C_1$ alkyl groups) are more preferred, and a trifluoromethyl group is yet more preferred.

In the present invention, a "$C_1$-$C_3$ alkylene group" means a straight or branched alkylene group having 1 to 3 carbon atoms. Examples thereof include a methylene group, an ethylene group, a propylene group, and an isopropylene group. A methylene group or an ethylene group ($C_1$-$C_2$ alkylene groups) is preferred, and a methylene group (a $C_1$ alkylene group) is yet more preferred.

In the present invention, a "$C_1$-$C_6$ alkoxy group" means a group in which the above described "$C_1$-$C_6$ alkyl group" binds to an oxygen atom, and means a straight or branched alkoxy group having 1 to 6 carbon atoms. Examples thereof include a methoxy group, an ethoxy group, a propoxy group, an isopropoxy group, a butoxy group, an isobutoxy group, an s-butoxy group, a t-butoxy group, a pentoxy group, a 2-methylbutoxy group, a 3-ethylpropoxy group, a neopentoxy group, a hexyloxy group, and a 2,3-dimethylbutoxy group. Straight or branched alkoxy groups having 1 to 4 carbon atoms ($C_1$-$C_4$ alkoxy groups) are preferred, a methoxy group or an ethoxy group ($C_1$-$C_2$ alkoxy groups) is more preferred, and a methoxy group (a $C_1$ alkoxy group) is yet more preferred.

In the present invention, a "$C_1$-$C_3$ alkoxy group" means a group in which the above described "$C_1$-$C_3$ alkyl group" binds to an oxygen atom, and means a straight or branched alkoxy group having 1 to 3 carbon atoms. Examples thereof include a methoxy group, an ethoxy group, a propoxy group, and an isopropoxy group. A methoxy group or an ethoxy group ($C_1$-$C_2$ alkoxy groups) is preferred, and a methoxy group (a $C_1$ alkoxy group) is yet more preferred.

In the present invention, a "$C_1$-$C_3$ alkoxy $C_1$-$C_6$ alkyl group" means a group in which one "$C_1$-$C_3$ alkoxy group," as described above, binds to the above described "$C_1$-$C_6$ alkyl group." Examples thereof include a methoxymethyl group, an ethoxymethyl group, a propoxymethyl group, an isopropoxymethyl group, a 2-methoxyethyl group, a 2-ethoxyethyl group, and a 3-isopropoxypropyl group. Groups in which one "$C_1$-$C_2$ alkoxy group," as described above, binds to the above described "$C_1$-$C_2$ alkyl group" ($C_1$-$C_2$ alkoxy $C_1$-$C_2$ alkyl groups) are preferred, and a methoxymethyl group (a $C_1$ alkoxy $C_1$ alkyl group) is yet more preferred.

In the present invention, a "$C_1$-$C_6$ alkoxycarbonyl group" means a group in which one "$C_1$-$C_6$ alkoxy group," as described above, binds to a carbonyl group. Examples thereof include a methoxycarbonyl group, an ethoxycarbonyl group, a propoxycarbonyl group, an isopropoxycarbonyl group, a butoxycarbonyl group, an isobutoxycarbonyl group, an s-butoxycarbonyl group, and a t-butoxycarbonyl group. Groups in which one "$C_1$-$C_4$ alkoxy group," as described above, binds to a carbonyl group ($C_1$-$C_4$ alkoxycarbonyl groups) are preferred, a methoxycarbonyl group or an ethoxycarbonyl group ($C_1$-$C_2$ alkoxycarbonyl groups) is more preferred, and an ethoxycarbonyl group (a $C_2$ alkoxycarbonyl group) is yet more preferred.

In the present invention, a "$C_1$-$C_6$ alkyl group that may have 1 to 3 substituents independently selected from the group A" means a $C_1$-$C_6$ alkyl group or a $C_1$-$C_6$ alkyl group that has 1 to 3 substituents independently selected from the group A. Preferred is a $C_1$-$C_2$ alkyl group or a $C_1$-$C_2$ alkyl group that has one substituent selected from the group A, wherein the phenyl group or the pyridyl group, which is a substituent selected from the group A, is unsubstituted or substituted with 1 to 3 halogen atoms. More preferred are a methyl group, an ethyl group, a phenylmethyl group, a phenylethyl group, a 4 chlorophenylmethyl group, a 2-chlorophenylmethyl group, a 3-chlorophenylmethyl group, a 2-pyridylmethyl group, a 3-pyridylmethyl group, a 4-pyridylmethyl group, a 2-pyridylethyl group, a 3-pyridylethyl group, and a 4-pyridylethyl group.

In the present invention, a "$C_1$-$C_6$ alkyl group that may have 1 or 2 substituents independently selected from the group C" means a $C_1$-$C_6$ alkyl group or a $C_1$-$C_6$ alkyl group that has 1 or 2 substituents independently selected from the group C. Preferred is a $C_1$-$C_4$ alkyl group or a $C_1$-$C_4$ alkyl group that has one substituent selected from the group C, wherein the substituent selected from the group C is a halogen atom, a hydroxy group, a cyano group, a carbamoyl group, a carboxyl group, a $C_1$-$C_3$ alkoxy group, a phenyl group, or a pyridyl group. Herein, the phenyl group or the pyridyl group may be unsubstituted or have 1 to 3 substituents independently selected from the group D, wherein the substituent of the group D is preferably a halogen atom, a cyano group, or a $C_1$-$C_4$ alkyl group. More preferred are a methyl group, an ethyl group, a propyl group, an isopropyl group, a fluoropropyl group, a hydroxyethyl group, a hydroxybutyl group, a 1-carbamoylethyl group, a carboxymethyl group, a propyloxypropyl group, a phenylmethyl group, a 2-fluorophenylmethyl group, a 3-fluorophenylmethyl group, a 4-fluorophenylmethyl group, a 2,4-difluorophenylmethyl group, a 3-cyanophenylmethyl group, a 2-pyridylmethyl group, a 3-pyridylmethyl group, a 4-pyridylmethyl group, and a 4-methyl-3-pyridylmethyl group.

In the present invention, a "$C_3$-$C_6$ cycloalkyl group that may have 1 or 2 substituents independently selected from the group C" means a $C_3$-$C_6$ cycloalkyl group or a $C_3$-$C_6$ cycloalkyl group that has 1 or 2 substituents independently selected from the group C. Preferred are $C_3$-$C_6$ cycloalkyl groups or $C_3$-$C_6$ cycloalkyl groups that have one substituent selected from the group C, wherein the substituent selected from the group C is a cyano group. A cyanocyclobutyl group is more preferred.

In the present invention, X is preferably a carboxyl group.

In the present invention, Q is preferably a $C_1$ alkylene group, an oxygen atom, a sulfur atom, or $R^a$N, wherein $R^a$ is a hydrogen atom, and more preferably a methylene group (a $C_1$ alkylene group), an oxygen atom, or a sulfur atom.

In the present invention, a preferred substituent of G is independently selected from the group consisting of a fluorine atom, a chlorine atom, a cyano group, a $C_1$-$C_3$ alkyl group, a $C_1$-$C_3$ alkoxy group, and a trihalo $C_1$-$C_3$ alkyl group (preferably a trihalomethyl group).

In the present invention, G is preferably a phenyl group that has 1 to 2 preferred substituents of G, as described above, or an unsubstituted phenyl group, and more preferably a phenyl group that has 1 to 2 substituents independently selected from a fluorine atom and a chlorine atom.

In the present invention, $R^1$ is preferably a $C_1$-$C_6$ alkyl group, a $C_1$ alkoxy-$C_1$ alkyl group, or a $C_3$ cycloalkyl group, more preferably a $C_1$-$C_6$ alkyl group, and yet more preferably a $C_1$-$C_3$ alkyl group.

In the present invention, a preferred group A is a phenyl group substituted with a $C_1$-$C_6$ alkyl group, an unsubstituted phenyl group, and an unsubstituted pyridyl group.

In the present invention, a preferred example where $R^2$ is a $C_1$-$C_6$ alkyl group is a $C_1$-$C_6$ alkyl group that is substituted with one substituent from the preferred group A or unsubstituted. More preferred is a $C_1$-$C_6$ alkyl group that is substituted with an unsubstituted pyridyl group or unsubstituted.

In the present invention, when $R^2$ represents a group that is selected from the group B, a preferred group B is —O-M, —S-M, —NH$_2$, —NH-M, and —NM$_2$, and more preferably —O-M, —S-M, and —NH-M.

In the present invention, M is preferably a $C_1$-$C_6$ alkyl group (preferably a $C_1$-$C_4$ alkyl group) that may have 1 or 2 substituents independently selected from the group C, or a $C_3$-$C_6$ cycloalkyl group (preferably a $C_4$ cycloalkyl group) that may have one substituent independently selected from the group C. Herein, a preferred group C is a halogen atom, a hydroxy group, a cyano group, a carbamoyl group, a carboxyl group, a $C_1$-$C_3$ alkoxy group, a phenyl group, and a pyridyl group, wherein the phenyl group and the pyridyl group may have 1 to 3 groups independently selected from the group D. Herein, the group D is preferably a halogen atom, a cyano group, and a $C_1$-$C_6$ alkyl group.

In the present invention, M is more preferably a $C_1$-$C_6$ alkyl group (preferably a $C_1$-$C_4$ alkyl group) that may have 1 or 2 substituents independently selected from the group $C^1$, or a $C_3$-$C_6$ cycloalkyl group (preferably a $C_4$ cycloalkyl group) that may have one substituent independently selected from the group $C^1$. Herein, the group $C^1$ is a halogen atom, a cyano group, a phenyl group, and a pyridyl group, wherein the phenyl group and the pyridyl group may have 1 to 3 substituents independently selected from the group $D^1$. Herein, the group $D^1$ is a halogen atom, a cyano group, and a $C_1$-$C_6$ alkyl group.

M is more preferably an unsubstituted $C_1$-$C_3$ alkyl group, a $C_1$-$C_3$ alkyl group that has 1 or 2 halogen atoms, a $C_1$-$C_3$ alkyl group that is substituted with one unsubstituted phenyl group, a $C_1$-$C_3$ alkyl group that is substituted with one unsubstituted pyridyl group, or a $C_4$ cycloalkyl group that is substituted with one cyano group.

In the present invention, a preferred combination of substituents in general formula (I) is as follows:
Q represents a methylene group (a $C_1$ alkylene group), an oxygen atom, or a sulfur atom;
G is a phenyl group having 1 to 2 substituents independently selected from the group consisting of a chlorine atom and a fluorine atom;
$R^1$ is a $C_1$-$C_3$ alkyl group; and
$R^2$ is a $C_1$-$C_6$ alkyl group that may be substituted with one pyridyl group, or —O-M, —S-M, —NH-M,
wherein M is a $C_1$-$C_6$ alkyl group that may have 1 or 2 substituents independently selected from the following group $C^1$, or a $C_3$-$C_6$ cycloalkyl group that may have one substituent independently selected from the following group $C^1$:
Group $C^1$: a halogen atom, a cyano group, a phenyl group, and a pyridyl group,
wherein the phenyl group and the pyridyl group may have 1 to 3 substituents independently selected from the following group $D^1$; and
Group $D^1$: a halogen atom, a cyano group, a $C_1$-$C_6$ alkyl group.

A compound of the present invention represented by general formula (I) or a pharmaceutically acceptable salt thereof may have all isomers (keto-enol isomers, diastereoisomers, optical isomers, rotational isomers, etc.)

A compound of the present invention represented by general formula (I) or a pharmaceutically acceptable salt thereof may have various isomers when an asymmetric carbon atom is present in the molecule. In the compounds of the present invention, these isomers and mixtures of these isomers are all shown with a single formula, that is, general formula (I). Therefore, the present invention encompasses all of these isomers and mixtures of these isomers in arbitrary ratios.

The stereoisomers described above can be obtained by synthesizing a compound according to the present invention using an optically active raw material compound or using an asymmetric synthesis or asymmetric induction technique, or by isolating the synthesized compound according to the present invention by a common optical resolution or separation method if desired.

A compound of the present invention represented by general formula (I) or a pharmaceutically acceptable salt thereof may contain an atomic isotope at a non-natural ratio for one or more atoms constituting such a compound. Examples of the atomic isotope include deuterium ($^2$H), tritium ($^3$H), iodine-125 ($^{125}$I), and carbon-14 ($^{14}$C). Furthermore, the compound may be radiolabeled with a radioisotope, such as tritium ($^3$H), iodine-125 ($^{125}$I), or carbon-14 ($^{14}$C). Such a radiolabeled compound is useful as a therapeutic or prophylactic agent, a research reagent, such as an assay reagent, and a diagnostic agent, for example an in vivo diagnostic imaging agent. All isotopic variants of the compound of the present invention shall fall within the scope of the present invention, regardless of being radioactive or not.

A "pharmaceutically acceptable salt thereof" refers to a salt that can be used as a medicament without significant toxicity. A compound of the present invention represented by general formula (I) can be formed into a salt by having the compound react with an acid when it has a basic group, or by having the compound react with a base when it has an acidic group.

Examples of salts based on a basic group may include inorganic acid salts including hydrohalide salts, such as hydrofluoride salts, hydrochloride salts, hydrobromide salts and hydroiodide salts, nitrate salts, perchlorate salts, sulfate salts, and phosphate salts; organic acid salts including $C_1$-$C_6$ alkylsulfonic acid salts, such as methanesulfonate salts, trifluoromethanesulfonate salts and ethanesulfonate salts, arylsulfonic acid salts, such as benzenesulfonate salts and p-toluenesulfonate salts, acetate salts, trifluoroacetate salts, malate salts, fumarate salts, succinate salts, citrate salts, ascorbate salts, tartarate salts, oxalate salts, and maleate salts; and amino acid salts, such as glycine salts, lysine salts, arginine salts, ornithine salts, glutamic acid salts and aspartic acid salts.

Meanwhile, examples of salts based on an acidic group may include, but are not limited to, metal salts including alkali metal salts, such as sodium salts, potassium salts and lithium salts, alkaline earth metal salts, such as calcium salts and magnesium salts, aluminum salts, iron salts, and zinc salts; amine salts including inorganic salts, such as ammonium salts, and organic salts, such as tert-butylamine salts, tert-octylamine salts, diisopropylamine salts, dibenzylamine salts, morpholine salts, glucosamine salts, phenyl glycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts, and tris(hydroxymethyl)aminomethane salts; and amino acid salts, such as glycine salts, lysine salts, arginine salts, ornithine salts, glutamic acid salts and aspartic acid salts.

Examples of preferred salts include hydrochloride salts, trifluoroacetate salts, magnesium salts, calcium salts, zinc salts, sodium salts, tert-butylamine salts, or diisopropylamine salts.

A compound of the present invention represented by general formula (I) may be formed into a salt in combination with the above described acid or base at any ratio. For example, hydrochloric acid salts encompass salts that may be formed, such as monohydrochloride, dihydrochloride and trihydrochloride salts, and magnesium salts encompass salts that may be formed, such as monomagnesium and hemimagnesium salts. In the names of a compound of the present invention, "monoacidic salts" or "monobasic salts" may be set forth as "acidic salts" wherein "mono" in the name is omitted. For example, "monohydrochloride salts" may be indicated as "hydrochloride salts" and "monomagnesium salts" as "magnesium salts."

When a compound of the present invention represented by general formula (I) or a pharmaceutically acceptable salt thereof is left in the atmosphere or recrystallized, a hydrate may be formed due to the attachment of adsorbed water or the absorption of water molecules. Such hydrates also fall within pharmaceutically acceptable salts of the present invention.

When a compound of the present invention represented by general formula (I) or a pharmaceutically acceptable salt thereof is left in a solvent or recrystallized in a solvent, a solvate may be formed by absorbing a certain kind of solvent. Such solvates also fall within salts of the present invention.

Each of the hydrates or solvates formed by a compound of the present invention represented by general formula (I) or a pharmaceutically acceptable salt thereof in combination with water or a solvent in any ratio, or a mixture thereof is encompassed by the present invention. For example, hydrates that may be formed, such as monohydrates, dihydrates, hemihydrates and ½ hydrates, and solvates that may be formed, such as monosolvates, disolvates, hemisolvates, and ½ solvates, are encompassed by the present invention. In the names of a compound of the present invention, the term "hydrates" or "solvates" with no hydration number or solvation number encompasses hydrates or solvates with any hydration or solvation number.

More specifically, preferred examples of a compound of the present invention represented by general formula (I) or a pharmaceutically acceptable salt thereof include the following:

5-(2,4-dichlorobenzyl)-4-(ethylamino)-6-methylpyrimidine-2-carboxylic acid or a pharmaceutically acceptable salt thereof;

5-((2-chlorophenyl)thio)-4-(ethylamino)-6-methylpyrimidine-2-carboxylic acid or a pharmaceutically acceptable salt thereof;

5-(2-chlorobenzyl)-4-methoxy-6-methylpyrimidine-2-carboxylic acid or a pharmaceutically acceptable salt thereof;

5-(2-chlorobenzyl)-4-ethyl-6-methoxypyrimidine-2-carboxylic acid or a pharmaceutically acceptable salt thereof;

5-(2-chloro-3-fluorobenzyl)-4-ethyl-6-methoxypyrimidine-2-carboxylic acid or a pharmaceutically acceptable salt thereof;

5-(2-chlorobenzyl)-4-ethyl-6-(3-fluoropropoxy)pyrimidine-2-carboxylic acid or a pharmaceutically acceptable salt thereof;

5-(2,4-dichlorobenzyl)-4-methyl-6-(methylthio)pyrimidine-2-carboxylic acid or a pharmaceutically acceptable salt thereof;

4-(benzyloxy)-5-(2-chlorobenzyl)-6-methylpyrimidine-2-carboxylic acid or a pharmaceutically acceptable salt thereof;

5-(2-chlorobenzyl)-4-methyl-6-(pyridin-4-ylmethoxy)pyrimidine-2-carboxylic acid or a pharmaceutically acceptable salt thereof; or 5-(2-chlorobenzyl)-4-methyl-6-(2-(pyridin-4-yl)ethyl)pyrimidine-2-carboxylic acid or a pharmaceutically acceptable salt thereof.

As further preferred examples, mention may be made of 5-(2-chlorobenzyl)-4-methoxy-6-methylpyrimidine-2-carboxylic acid or a pharmaceutically acceptable salt thereof; or 5-(2-chlorobenzyl)-4-ethyl-6-methoxypyrimidine-2-carboxylic acid or a pharmaceutically acceptable salt thereof.

More preferably, mention may be made of 5-(2-chlorobenzyl)-4-methoxy-6-methylpyrimidine-2-carboxylic acid, or a magnesium salt, a calcium salt, a zinc salt, a sodium salt, a tert-butylamine salt, or a diisopropylamine salt thereof. They may be in the form of a hydrate.

A compound of the present invention represented by general formula (I) or a pharmaceutically acceptable salt thereof may produce a crystal having a plurality of different internal structures and physicochemical properties (a crystalline polymorph) depending on reaction conditions and crystallization conditions. Each of these crystals or a mixture thereof at any ratio is encompassed by the present invention. In the case where a crystalline solid and an amorphous solid may coexist with each other, a mixture thereof at any ratio is encompassed by the present invention. Thus, a crystal of the present invention having a particular crystalline form may contain a crystal having another crystalline form or an amorphous solid. The content percentage of a particular crystal is preferably 50% or more, more preferably 80% or more, still more preferably 90% or more, even more preferably 93% or more, particularly preferably 95% or more, and most preferably 97% or more.

In the present invention, a crystal refers to a solid whose internal structure is three-dimensionally composed of a regular repetition of constituent atoms (or a group thereof) and is distinguished from an amorphous solid, which does not have such a regular internal structure. It is possible to examine whether a certain solid is a crystal or not by crystallographically well known methods (powder X-ray crystal diffraction, differential thermal analysis, etc.)

When a crystal of the present invention is left in the atmosphere, a hydrate may be formed due to absorption of moisture and attachment of adhesion water, or by heating the crystal to 25 to 150° C. in normal atmospheric conditions, etc. Furthermore, a crystal of the present invention may contain an attached residual solvent, or a solvent used at the time of crystallization in the solvate.

In this specification, a crystal of the present invention may be expressed on the basis of powder X-ray diffraction data. In the powder X-ray diffraction, measurement and analysis may be performed by methods conventionally used in this field, and for example, the powder X-ray diffraction can be performed by a method described in the Examples. Furthermore, in general, in the case of a hydrated or dehydrated crystal, the lattice constant thereof may vary with the addition or removal of crystalline water, thereby changing the diffraction angle (2θ) in powder X-ray diffraction. In addition, the peak intensity may vary due to a difference between growth surfaces of the crystal (crystal habit), etc. Accordingly, when a crystal of the present invention is expressed with diffraction angles of main peaks in a powder X-ray diffraction pattern, even if the diffraction angles differ slightly, the identity of crystalline forms may be recognized with an appropriate reference to the whole pattern of the spectrum. In addition to crystals having a corresponding X-ray diffraction pattern, hydrated and dehydrated crystals obtained therefrom are also encompassed within the scope of the present invention.

In the powder X-ray diffraction patterns of FIGS. 6 to 13 below, diffraction intensity [counts/sec (cps)] is shown on the vertical axis, and diffraction angle 2θ (degree) is shown on the horizontal axis. The spacing d (Å) can be calculated according to the equation: $2d \sin \theta = n\lambda$, wherein n=1. In this equation, the wavelength λ of the copper Kα radiation is 1.54 Å. The position (numerical value) and relative intensity of the spacing d may vary depending on measurement conditions. Thus, even if the spacing d differs slightly, the identity of crystalline forms may be recognized with an appropriate reference to the whole pattern of the spectrum. The crystalline form may also be identified with the spacing d that corresponds to a main peak in the powder X-ray diffraction pattern. Main peaks may be selected appropriately as characteristic peaks among, for example, peaks having a relative intensity that is not less than the appropriately predetermined numerical value.

One more specific aspect of a crystal of the present invention is a crystal of a hydrate, a magnesium salt hydrate, a calcium salt hydrate, a zinc salt hydrate, a sodium salt anhydride, a tert-butylamine salt anhydride, or a diisopropylamine salt anhydride of 5-(2-chlorobenzyl)-4-methoxy-6-methylpyrimidine-2-carboxylic acid, and more preferably a crystal of the hydrate or the magnesium salt hydrate.

More preferably, it is a crystal of bis[5-(2-chlorobenzyl)-4-methoxy-6-methylpyrimidine-2-carboxylic acid] magnesium salt having main peaks at diffraction angles 2θ=11.82, 13.74, 14.26, 15.38, 21.56, 23.42, 24.14, 27.82, 28.72, and 31.06 in a powder X-ray diffraction pattern obtained by irradiation with copper Kα radiation (wavelength λ=1.54 angstroms). The crystal exhibits the powder X-ray diffraction pattern of FIG. 8 by irradiation with copper Kα radiation (wavelength λ=1.54 angstroms).

As another preferred example, mention may also be made of a crystal of bis[5-(2-chlorobenzyl)-4-methoxy-6-methylpyrimidine-2-carboxylic acid] magnesium salt having main peaks at diffraction angles 2θ=5.18, 10.44, 18.98, 19.68, 22.36, 23.76, 26.34, and 27.96 in a powder X-ray diffraction pattern obtained by irradiation with copper Kα radiation (wavelength λ=1.54 angstroms). The crystal exhibits the powder X-ray diffraction pattern of FIG. 7 by irradiation with copper Kα radiation (wavelength λ=1.54 angstroms).

Furthermore, as another preferred example, mention may also be made of a crystal of 5-(2-chlorobenzyl)-4-methoxy-6-methylpyrimidine-2-carboxylic acid having main peaks at diffraction angles 2θ=6.68, 10.54, 16.16, 20.16, 21.22, 21.58, 24.20, 25.16, and 33.92 in a powder X-ray diffraction pattern obtained by irradiation with copper Kα radiation (wavelength λ=1.54 angstroms). The crystal exhibits the powder X-ray diffraction pattern of FIG. 6 by irradiation with copper Kα radiation (wavelength λ=1.54 angstroms).

Advantageous Effects of the Invention

A compound of the present invention represented by general formula (I) or a pharmaceutically acceptable salt thereof has strong chloride ion-secretory action via GPR39 agonism and moves moisture. Therefore, a compound of the present invention or a pharmacologically acceptable salt thereof is useful as a prophylactic or therapeutic agent of a disease that is prevented or treated via GPR39 agonism, or a disease whose symptoms are prevented, ameliorated, or relieved by opening a calcium dependent chloride channel. Specific examples of such a disease include cystic fibrosis, non-CF bronchiectasis, primary ciliary dyskinesia, dry eye, constipation, adiposity, diabetes mellitus, ulcerative colitis, Crohn's disease, depression, COPD, and the like.

A preferred disease is cystic fibrosis.

BRIEF DESCRIPTION OF DRAWINGS

FIG. 1 is a graph showing change in expression level of human GPR39 in CuFi-1 cells through siRNA treatment (mRNA expression analysis). The vertical axis is expressed as a relative expression level towards the control siRNA treated group. The graph is shown with the mean value (N=3) and the standard deviation.

FIG. 2 is a graph showing effects on the chloride secretory activity of each compound in CuFi-1 cells through siRNA treatment. The vertical axis is expressed as an increase in the rate of the average value of fluorescence values at five points between 110 and 120 seconds, relative to the average value of fluorescence values at 17 points between 1 and 34 seconds within the measurement time of 120 seconds. The graph is shown with the mean value (N=8) and the standard deviation.

FIG. 3 is a graph showing the moisture transporting action of each compound in MucilAir-CF™ cells (lot #MD048502), which have a ΔF508 homozygous mutation in the class II mutation of CFTR. The vertical axis is expressed as a percentage of remaining moisture. The mean value and the standard deviation are shown. Dunnett's multiple comparison test with the group without addition of Example 38 or the control groups is performed, and groups with a p-value of no more than 0.01 are shown with **. By using #, it is shown that the p-value via Student's t test is 0.032 between the group without addition of Example 38 and the group to which a combination of VX-809 (30 μM) and VX-770 (1 μM) is added.

FIG. 4 is a graph showing the moisture transporting action of each compound in MucilAir-CF™ cells (lot #MD020802), which have a 2184ΔA+W1282X mutation in the class I mutation of CFTR. The vertical axis is expressed as a percentage of remaining moisture. The mean value and the standard deviation are shown. Dunnett's multiple comparison test with the group without addition of Example 38 or the control groups was performed, and groups with a p-value of no more than 0.01 are shown with **.

FIG. 5 is a graph showing the moisture transporting action of each compound in MucilAir-CF™ cells (lot #MD062201), which have a N1303K heterozygous mutation in the class II mutation of CFTR. The vertical axis is expressed as a percentage of remaining moisture. The mean value and the standard deviation are shown. Dunnett's multiple comparison test with the group without addition of Example 38 or the control groups was performed, and groups with a p-value of no more than 0.01 are shown with **.

FIG. 6 shows a powder X-ray diffraction pattern of the crystal obtained in Example 107.

FIG. 7 shows a powder X-ray diffraction pattern of the crystal obtained in Example 108.

FIG. 8 shows a powder X-ray diffraction pattern of the crystal obtained in Example 109.

FIG. 9 shows a powder X-ray diffraction pattern of the crystal obtained in Example 110.

FIG. 10 shows a powder X-ray diffraction pattern of the crystal obtained in Example 111.

FIG. 11 shows a powder X-ray diffraction pattern of the crystal obtained in Example 112.

FIG. 12 shows a powder X-ray diffraction pattern of the crystal obtained in Example 113.

FIG. 13 shows a powder X-ray diffraction pattern of the crystal obtained in Example 114.

DESCRIPTION OF EMBODIMENTS

Next, typical production processes for compounds represented by general formula (I) will be described. Compounds of the present invention can be produced by various production processes. The production processes shown below are given merely for illustrative purposes and the present invention should not be construed to be limited thereby. A compound represented by general formula (I) and production intermediates thereof may be produced utilizing various known reactions mentioned below. Upon production, functional groups may be protected with appropriate protecting groups at the stage of the raw material or an intermediate. Examples of such functional groups may include a hydroxy group, a carboxyl group, an amino group, etc. For types of protecting groups, as well as conditions for introducing and removing these protecting groups, reference may be made to those described in, for example, Protective Groups in Organic Synthesis, Third Edition (T. W. Green and P. G. M. Wuts, John Wiley & Sons, Inc., New York).

[Production Process 1]

Among compounds represented by formula (I), compound 1a shown below may be produced, for example, via the following reaction formula:

wherein, G and $R^1$ have the same meanings as described above; $Q^1$ represents a $C_1$-$C_3$ alkylene group, and $P^a$, $P^b$, and $P^c$ represent protecting groups; and $R^{2a}$ represents a group selected from the following group $B^{1a}$.

Group $B^{1a}$: —O-$M^{1a}$, —S-$M^{1a}$, —NH-$M^{1a}$, and —N-$(M^{1a})_2$, wherein $M^{1a}$ is a $C_1$-$C_6$ alkyl group that may have 1 or 2 substituents independently selected from the following group $C^{1a}$, or a $C_3$-$C_6$ cycloalkyl group that may have 1 or 2 substituents independently selected from the following group $C^{1a}$;

Group $C^{1a}$: a fluorine atom, a hydroxy group, a cyano group, a carbamoyl group, a carboxyl group, a $C_1$-$C_6$ alkoxycarbonyl group, a $C_1$-$C_6$ alkoxy group, a phenyl group, and a pyridyl group, wherein the phenyl group and the pyridyl group may have 1 to 3 substituents independently selected from the following group $D^{1a}$; and Group $D^{1a}$: a halogen atom, a cyano group, a $C_1$-$C_6$ alkyl group, a $C_1$-$C_6$ alkoxy group, and a trihalo $C_1$-$C_6$ alkyl group.

[Formula 3]

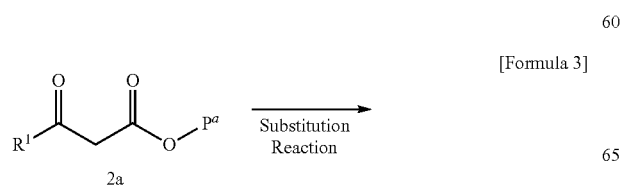

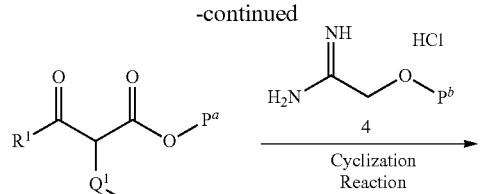

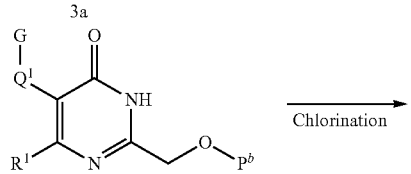

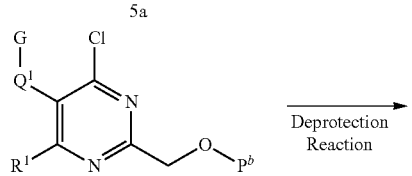

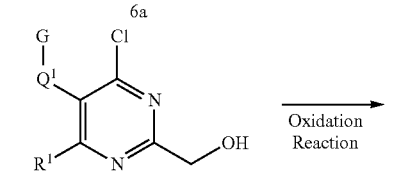

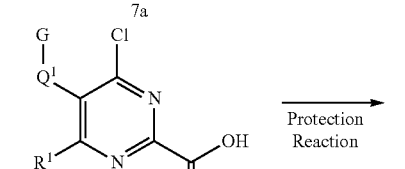

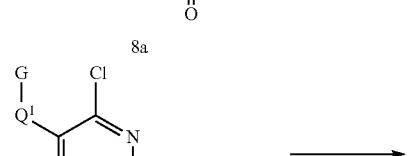

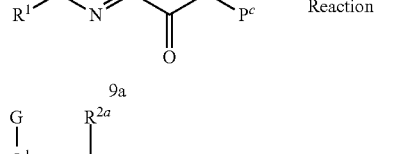

(1) Conversion of Compound 2a to Compound 3a

The conversion of compound 2a to compound 3a may be performed by having the ester compound 2a react with a corresponding alkyl halide in an appropriate solvent that does not exert adverse effects on the reaction (for example, benzene, toluene, diethyl ether, dichloromethane, tetrahydrofuran, N,N-dimethylformamide, or the like, or a mixed solvent thereof) in the presence of an appropriate base (for example, sodium hydride, sodium methoxide, potassium tert-butoxide, etc., or a mixture thereof) at a temperature from −30° C. to the boiling point of the solvent used for the reaction, preferably from 0° C. to 100° C. The reaction time is preferably from 10 minutes to 72 hours, and more preferably from 8 hours to 24 hours.

As for compound 2a, the raw material for production, it may be commercially obtained or synthesized in accordance with known methods.

(2) Conversion of Compound 3a to Compound 5a

The conversion of compound 3a to compound 5a may be performed by having compound 4 react in an appropriate solvent that does not exert adverse effects on the reaction (for example, N,N-dimethylformamide, acetone, etc., or a mixed solvent thereof) in the presence of an appropriate base (for example, triethylamine, N,N-diisopropylethylamine, 4-dimethylaminopyridine, N-methylmorpholine, pyridine, 2,6-lutidine, diazabicyclo[5.4.0]undec-7-ene, etc., or a mixture thereof) at a temperature from room temperature to the boiling point of the solvent used for the reaction, preferably from 50° C. to 100° C. As for the amount of the base, an excess amount may be used. The reaction time is preferably from 1 hour to 72 hours, and more preferably from 8 hours to 24 hours.

Compound 4, the raw material for production, may be synthesized in accordance with a method described in a reference example.

(3) Conversion of Compound 5a to Compound 6a

The conversion of compound 5a to compound 6a may be performed by having a chlorination agent, such as carbon tetrachloride, trichloroacetonitrile, N-chlorosuccinimide, react in an appropriate solvent that does not exert adverse effects on the reaction (for example, toluene, 1,4-dioxane, 1,2-dichloroethane, tetrahydrofuran, etc., or a mixed solvent thereof) in the presence of triphenylphosphine at a temperature from −30° C. to the boiling point of the solvent used for the reaction, preferably from room temperature to 120° C. The reaction time is preferably from 10 minutes to 12 hours, and more preferably from 30 minutes to 2 hours. Moreover, when $P^b$ is a methyl group, the conversion may be performed by treating with an appropriate chlorination agent (for example, oxalyl chloride, thionyl chloride, phosphorous oxychloride, etc.) in an appropriate solvent that does not exert adverse effects on the reaction (for example, chloroform, dichloromethane, tetrahydrofuran, 1,4-dioxane, etc., or a mixed solvent thereof) at a temperature from −30° C. to 100° C. or the boiling point of the solvent used for the reaction, preferably from room temperature to 100° C. The reaction time is preferably from 10 minutes to 24 hours, and more preferably from 30 minutes to 12 hours. Bases, such as triethylamine, N,N-dimethylaniline, and N,N-diethylaniline may also be added, as necessary. Furthermore, it is possible to add N,N-dimethylformamide and the like as a reaction accelerator.

(4) Conversion of Compound 6a to Compound 7a

In the conversion of compound 6a to compound 7a, the reaction conditions of deprotection are different depending on the type of $P^b$. When $P^b$ is a methyl group, the conversion may be performed by treating with a deprotecting agent, such as boron tribromide, in an appropriate solvent that does not exert adverse effects on the reaction (for example, dichloromethane, chloroform, etc., or a mixed solvent thereof) at a temperature from −78° C. to the boiling point of the solvent used for the reaction, preferably from −40° C. to room temperature. The reaction time is preferably from 1 hour to 72 hours, and more preferably from 2 hours to 24 hours. When $P^b$ is a tert-butyl group, the conversion may be performed by treating with trifluoroacetic acid, hydrochloric acid, formic acid, or the like at a temperature from −30° C. to the boiling point of the solvent used for the reaction, preferably from −20° C. to room temperature. The reaction time is preferably from 10 minutes to 72 hours, and more preferably from 30 minutes to 24 hours.

(5) Conversion of Compound 7a to Compound 8a

The conversion of compound 7a to compound 8a may be performed through a general oxidation reaction of converting a primary alcohol to a carboxylic acid. Representative examples of oxidizing agents may include potassium permanganate, chromium trioxide and dilute sulfuric acid (Jones oxidation), or (2,2,6,6-tetramethyl-1-piperidinyl)oxyl (TEMPO) and a cooxidizing agent (such as hypochlorite salts, bromite salts, N-chlorosuccinimide). Examples of solvents used for the reaction include acetone, acetonitrile, water, etc., or a mixed solvent thereof, and the conversion may be performed at a reaction temperature of from −78° C. to 100° C. or the boiling point of the solvent, preferably from room temperature to 80° C., and in a reaction time from 1 hour to 48 hours, preferably 1 hour to 24 hours.

It is also possible to oxidize an aldehyde again, which is obtained by oxidizing compound 7a, to obtain compound 8a. As an oxidation reaction to obtain an aldehyde, reactions using chromic acid [pyridinium chlorochromate (PCC), pyridinium dichromate (PDC), etc.], dimethyl sulfoxide and oxalyl chloride (Swern oxidation), dimethyl sulfoxide and acetic anhydride, dimethyl sulfoxide and pyridine sulfur trioxide complex, 1,1,1-triacetoxy-1,1-dihydro-1,2-benziodoxol-3(1H)-one (Dess-Martin reagent), etc. are known. As an oxidation reaction to obtain a carboxylic acid from an aldehyde, Pinnick oxidation, which uses sodium chlorite in the coexistence of 2-methyl-2-butene, is known.

(6) Conversion of Compound 8a to Compound 9a

The conversion of compound 8a to compound 9a may be performed through a general protection reaction of the carboxyl group. For example, the conversion may be performed by treating with an appropriate acid catalyst (for example, hydrogen chloride, sulfuric acid, thionyl chloride, or the like) in a lower alcohol corresponding to $P^c$, such as methanol or ethanol, at a temperature from room temperature to the boiling point of the solvent used for the reaction, preferably from room temperature to 100° C. The reaction time is preferably from 10 minutes to 72 hours, and more preferably from 30 minutes to 24 hours.

Moreover, a tert-butyl ester may be obtained by treating with an appropriate esterification agent (for example, N,N-dimethylformamide di-tert-butyl acetal, 0-tert-butyl-N,N'-diisopropylisourea, etc.) in an appropriate solvent that does not exert adverse effects on the reaction (toluene, dichloromethane, etc., or a mixed solvent thereof) at a temperature from room temperature to the boiling point of the solvent used for the reaction, preferably from room temperature to 100° C. The reaction time is preferably from 10 minutes to 72 hours, and more preferably from 30 minutes to 24 hours.

(7) Conversion of Compound 9a to Compound 10a

The conversion of compound 9a to compound 10a is performed through a nucleophilic substitution reaction between compound 9a and an alcohol, amine, or thiol. For example, when an alcohol is used to perform the substitution reaction described above, the reaction may be performed by treating with an appropriate base (for example, sodium hydride, potassium carbonate, cesium carbonate, etc.) in an appropriate solvent that does not exert adverse effects on the reaction (tetrahydrofuran, acetone, acetonitrile, 1,4-dioxane, dimethyl sulfoxide, etc., or a mixed solvent thereof) at a temperature from room temperature to the boiling point of the solvent used for the reaction, preferably from room temperature to 100° C. The reaction time is preferably from 6 hours to 72 hours, and more preferably from 12 hours to 24 hours. As for the amount of the base used, one to excess molar equivalents relative to compound 9a may be used, and more preferably, 1 to 5 molar equivalents are used. As for the amount of the alcohol used, one to excess molar equivalents relative to compound 10a may be used, and it is also possible to perform the reaction using the alcohol as the solvent. It is also possible to perform the reaction using metal alkoxides. Furthermore, a catalytic amount of a crown ether may be added.

For example, when an amine is used to perform the reaction described above, the reaction may be performed by treating with an appropriate base (for example, inorganic bases, such as potassium carbonate and cesium carbonate, organic bases, such as triethylamine and N,N-diisopropylethylamine), or by using an excess amount of the amine without using the base in an appropriate solvent that does not exert adverse effects on the reaction (tetrahydrofuran, 1,4-dioxane, etc., or a mixed solvent thereof) at a temperature from room temperature to the boiling point of the solvent used for the reaction, preferably from room temperature to 100° C. The reaction time is preferably from 6 hours to 72 hours, and more preferably from 12 hours to 24 hours. As for the amount of the base used, one to excess molar equivalents relative to compound 9a may be used, and more preferably, 1 to 2 molar equivalents are used. As for the amount of the amine used, 1 to 2 molar equivalents will do when the base is used, and a range of 2 to 30 molar equivalents relative to compound 9a is preferred when the base is not used. The reaction described above may also be conducted by treating in a sealed tube or under microwave irradiation.

Moreover, when a thiol is used to perform the substitution reaction described above, the reaction may be performed by conducting a basically similar method as for the case when an alcohol is used.

(8) Conversion of Compound 10a to Compound 1a

In the conversion of compound 10a to compound 1a, the reaction conditions of deprotection are different depending on the type of $P^c$. When $P^c$ is a methyl group, the conversion may be performed by treating with an appropriate base (for example, sodium hydroxide, potassium hydroxide, lithium hydroxide, potassium tert-butoxide, or the like) in an appropriate solvent that does not exert adverse effects on the reaction (for example, mention may be made of methanol, ethanol, water, tetrahydrofuran, 1,4-dioxane, etc., or a mixed solvent thereof, but an organic solvent that is miscible with water at any ratio is preferable) at a temperature from −30° C. to the boiling point of the solvent used for the reaction, preferably from room temperature to 100° C. The reaction time is preferably from 10 minutes to 72 hours, and more preferably from 30 minutes to 24 hours. When $P^c$ is a tert-butyl group, the conversion may be performed by, in addition to the above described deprotection reaction, treating with trifluoroacetic acid, hydrochloric acid, formic acid, or the like at a temperature from −30° C. to the boiling point of the solvent used for the reaction, preferably from −20° C. to room temperature. The reaction time is preferably from 10 minutes to 72 hours, and more preferably from 30 minutes to 24 hours.

[Production Process 2]

Compound 1a may also be obtained by performing the substitution reaction described in step (7) of the above [production process 1] to compound 8a of the [production process 1].

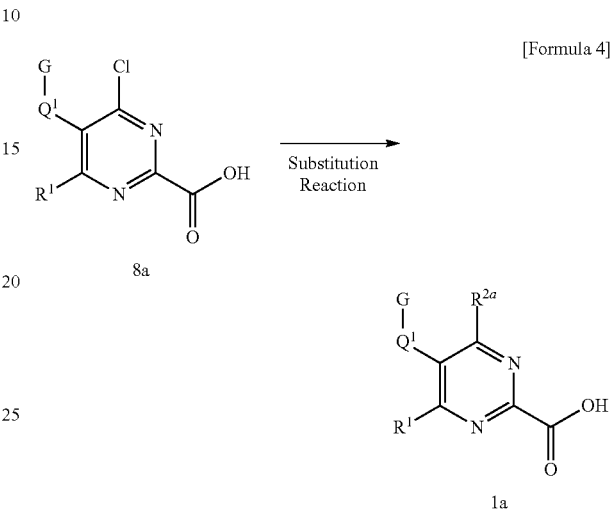

(1) Conversion of Compound 8a to Compound 1a

The conversion of compound 8a to compound 1a may be conducted by a similar substitution reaction as for the method described in step (7) of the above [production process 1].

[Production Process 3]

Among compounds represented by formula (I), compound 1b shown below may be produced, for example, via the following reaction formula:
wherein, G, $R^1$, $P^a$, $P^b$, and $R^{2a}$ have the same meanings as described above.

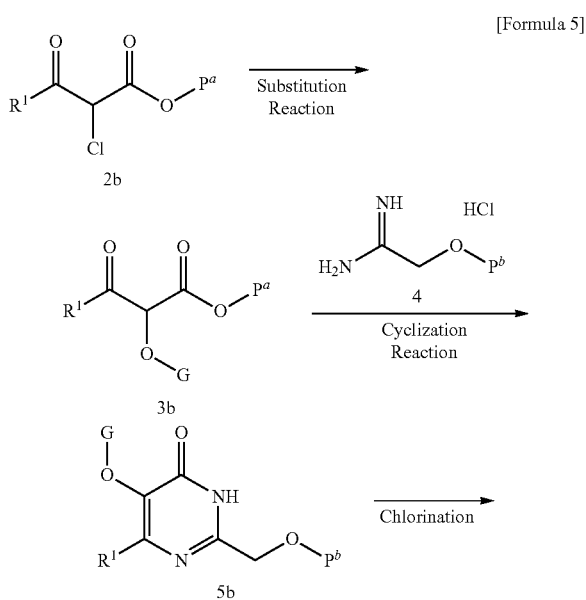

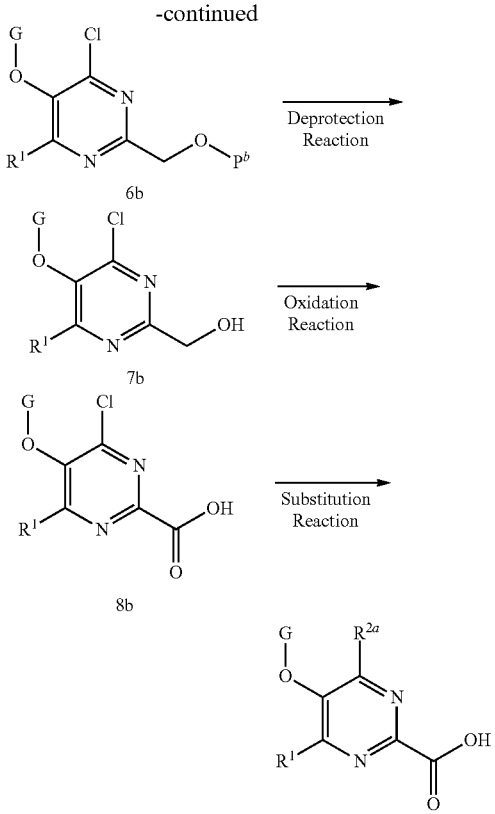

(1) Conversion of Compound 2b to Compound 3b

The conversion of compound 2b to compound 3b may be performed by having a corresponding phenol derivative react in an appropriate solvent that does not exert adverse effects on the reaction (for example, N,N-dimethylformamide, acetone, etc., or a mixed solvent thereof) in the presence of an appropriate base (for example, potassium carbonate, cesium carbonate, etc.) at a temperature from room temperature to the boiling point of the solvent used for the reaction, preferably from 50° C. to 100° C. As for the amount of the base, an excess amount may be used. The reaction time is preferably from 1 hour to 72 hours, and more preferably from 8 hours to 24 hours.

(2) Conversion of Compound 3b to Compound 5b

The conversion of compound 3b to compound 5b may be conducted by a similar, general cyclization reaction as for the method described in step (2) of the above [production process 1].

(3) Conversion of Compound 5b to Compound 6b

The conversion of compound 5b to compound 6b may be conducted by a similar, general chlorination reaction as for the method described in step (3) of the above [production process 1].

(4) Conversion of Compound 6b to Compound 7b

The conversion of compound 6b to compound 7b may be conducted by a similar, general deprotection reaction as for the method described in step (4) of the above [production process 1].

(5) Conversion of Compound 7b to Compound 8b

The conversion of compound 7b to compound 8b may be conducted by a similar, general oxidation reaction as for the method described in step (5) of the above [production process 1].

(6) Conversion of Compound 8b to Compound 1b

The conversion of compound 8b to compound 1b may be conducted by a similar, general substitution reaction as for the method described in step (7) of the above [production process 1].

[Production Process 4]

Among compounds represented by formula (I), compound 1c shown below may be produced from a starting raw material of 6c, which may be produced through the above [production process 1] or the above [production process 3], for example, via the following reaction formula:

wherein, G, $R^1$, and $P^b$ have the same meanings as described above, but $P^b$ is desirably a tert-butyl group; $Q^2$ represents a $C_1$-$C_3$ alkylene group or an oxygen atom; and $M^b$ represents a hydrogen atom, a $C_1$-$C_6$ alkyl group that may have 1 or 2 substituents independently selected from the following group $C^{1b}$, or a $C_3$-$C_6$ cycloalkyl group that may have 1 or 2 substituents independently selected from the following group $C^{1b}$.

Group $C^{1b}$: a cyano group, a $C_1$-$C_6$ alkoxy group, a phenyl group, and a pyridyl group, wherein the phenyl group and the pyridyl group may have 1 to 3 substituents independently selected from the following group $D^{1b}$; and Group $D^{1c}$: a halogen atom, a cyano group, a $C_1$-$C_6$ alkyl group, a $C_1$-$C_6$ alkoxy group, and a trihalo $C_1$-$C_6$ alkyl group.

[Formula 6]

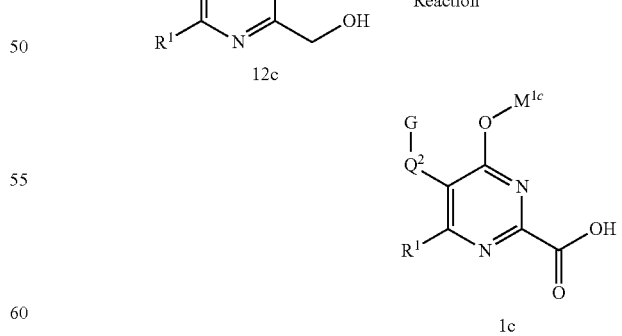

(1) Conversion of Compound 6c to Compound 11c

The conversion of compound 6c to compound 11c may be conducted by a similar substitution reaction as for the case when an alcohol is used, described in step (7) of the above [production process 1].

(2) Conversion of Compound 11c to Compound 12c

The conversion of compound 11c to compound 12c may be conducted by a similar, general deprotection reaction as for the method described in step (4) of the above [production process 1].

(3) Conversion of Compound 12c to Compound 1c

The conversion of compound 12c to compound 1c may be conducted by a similar, general oxidation reaction as for the method described in step (5) of the above [production process 1].

[Production Process 5]

Among compounds represented by formula (I), compound 1d shown below may be produced, for example, via the following reaction formula:

wherein, G, $R^1$, $P^a$, and $P^b$ have the same meanings as described above, but $P^b$ is desirably a tert-butyl group; and $M^{1d}$ represents a hydrogen atom, a $C_1$-$C_6$ alkyl group that may have 1 or 2 substituents independently selected from the following group $C^{1d}$, or a $C_3$-$C_6$ cycloalkyl group that may have 1 or 2 substituents independently selected from the following group C.

Group $C^{1d}$: a cyano group, a $C_1$-$C_6$ alkoxy group, a phenyl group, and a pyridyl group, wherein the phenyl group and the pyridyl group may have 1 to 3 substituents independently selected from the following group $D^{1d}$; and Group $D^{1d}$: a halogen atom, a cyano group, a $C_1$-$C_6$ alkyl group, a $C_1$-$C_6$ alkoxy group, and a trihalo $C_1$-$C_6$ alkyl group.

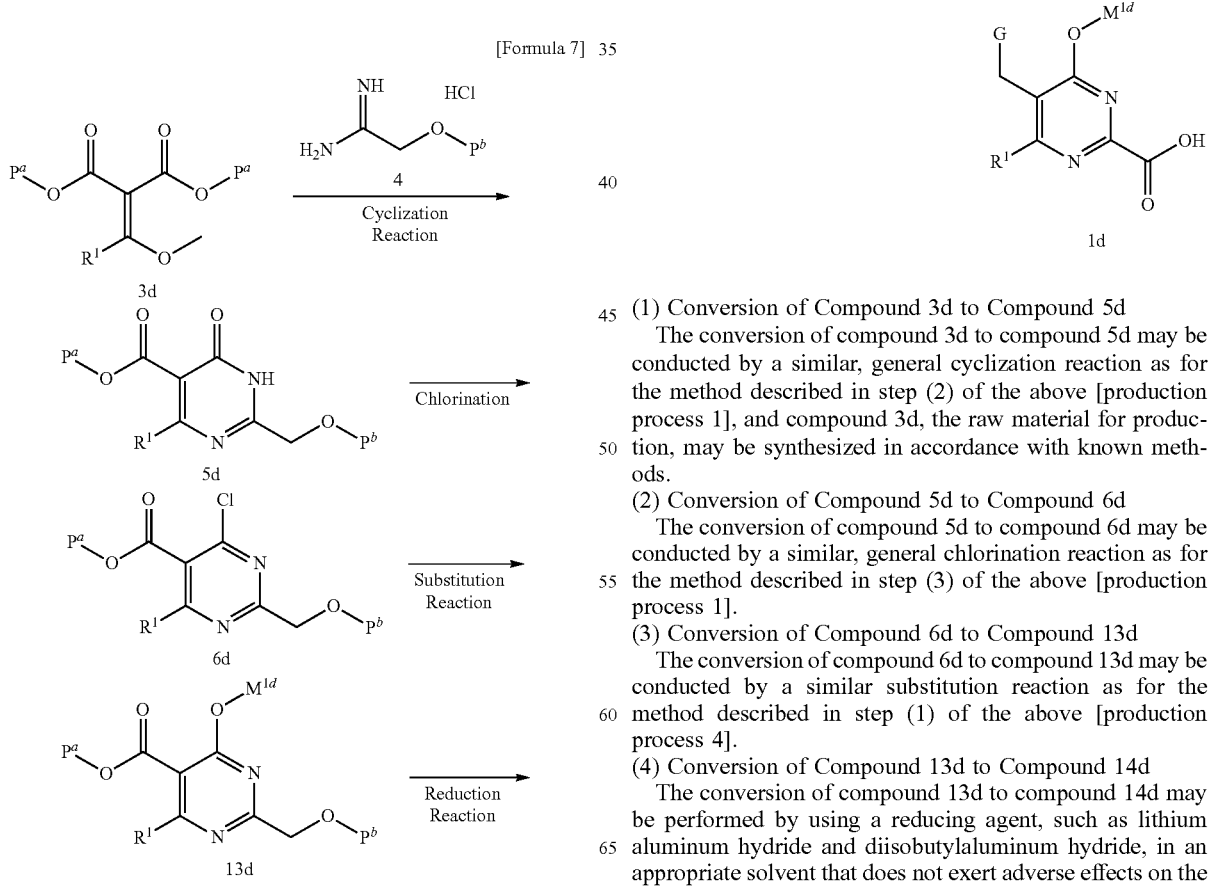

(1) Conversion of Compound 3d to Compound 5d

The conversion of compound 3d to compound 5d may be conducted by a similar, general cyclization reaction as for the method described in step (2) of the above [production process 1], and compound 3d, the raw material for production, may be synthesized in accordance with known methods.

(2) Conversion of Compound 5d to Compound 6d

The conversion of compound 5d to compound 6d may be conducted by a similar, general chlorination reaction as for the method described in step (3) of the above [production process 1].

(3) Conversion of Compound 6d to Compound 13d

The conversion of compound 6d to compound 13d may be conducted by a similar substitution reaction as for the method described in step (1) of the above [production process 4].

(4) Conversion of Compound 13d to Compound 14d

The conversion of compound 13d to compound 14d may be performed by using a reducing agent, such as lithium aluminum hydride and diisobutylaluminum hydride, in an appropriate solvent that does not exert adverse effects on the reaction (for example, diethyl ether, tetrahydrofuran, 1,4- dioxane, etc., or a mixed solvent thereof) at a temperature no more than room temperature, preferably from −78° C. to 0° C. The conversion may also be performed by using sodium borohydride or the like with a protic solvent, such as methanol, ethanol and water, or a mixed solvent thereof with the above described nonprotic solvent at a temperature no more than room temperature, preferably from −20° C. to around room temperature.

(5) Conversion of Compound 14d to Compound 15d

The conversion of compound 14d to compound 15d may be performed by having carbon tetrabromide react in an appropriate solvent that does not exert adverse effects on the reaction (for example, dichloromethane, 1,4-dioxane, 1,2-dichloroethane, tetrahydrofuran, etc., or a mixed solvent thereof) in the presence of triphenylphosphine at a temperature from −30° C. to the boiling point of the solvent used for the reaction, preferably from room temperature to 60° C. The reaction time is preferably from 30 minutes to 72 hours, and more preferably from 1 hour to 24 hours.

(6) Conversion of Compound 15d to Compound 11d

The conversion of compound 15d to compound 11d may be performed by conducting a coupling reaction with the use of known techniques in organic chemistry. Thus, the conversion is conducted in an appropriate solvent that does not exert adverse effects on the reaction (for example, N,N-dimethylformamide, tetrahydrofuran, dimethyl ethylene glycol, 1,4-dioxane, water or the like, or a mixed solvent thereof) in the presence of an appropriate organoboronic acid, organotin, organozinc, or organomagnesium derivative, etc., and an appropriate transition metal catalyst (as for the metal catalyst, palladium catalysts are preferable, and examples thereof include [1,1'-bis(diphenylphosphino)ferrocene]dichloropalladium(II)-dichloromethane complex, or dichlorobis(triphenylphosphine)palladium(II) and tetrakis(triphenylphosphine)palladium(0), etc.), as necessary with the addition of an organic or inorganic base (for example, sodium carbonate, potassium carbonate, cesium carbonate, tripotassium phosphate, N,N-diisopropylethylamine, etc.), a ligand (for example, triphenylphosphine, etc.), and a known reaction accelerating additive (for example, lithium chloride, copper iodide, or the like). In the above coupling reaction, the reaction temperature is preferably from 0° C. to 300° C., and more preferably from room temperature to 200° C. The reaction described above may also be conducted by treating in a sealed tube or under microwave irradiation. It is preferred that both of the organoboronic acid or the like and the base are used in an amount of one to excess molar equivalents relative to compound 15d, and it is more preferred that 1 to 1.5 molar equivalents for the organoboronic acid or the like and 1 to 5 molar equivalents for the base are used. The reaction time is preferably from 10 minutes to 60 hours, and more preferably from 30 minutes to 24 hours.

(7) Conversion of Compound 11d to Compound 12d

The conversion of compound 11d to compound 12d may be conducted by a similar, general deprotection reaction as for the method described in step (4) of the above [production process 1].

(8) Conversion of Compound 12d to Compound 1d

The conversion of compound 12d to compound 1d may be conducted by a similar, general oxidation reaction as for the method described in step (5) of the above [production process 1].

[Production Process 6]

Among compounds represented by formula (I), compound 1e shown below may be produced from a starting raw material of 9e, which may be produced through the above [production process 1] or the above [production process 3], for example, via the following reaction formula:

wherein, G, $R^1$, $P^c$, and $Q^2$ have the same meanings as described above; and $R^{2e}$ represents a $C_1$-$C_6$ alkyl group that may have 1 to 3 phenyl groups and pyridyl groups.

Here, the phenyl group and the pyridyl group may have 1 to 3 substituents independently selected from the following group $D^{1e}$:

Group $D^{1e}$: a cyano group, a $C_1$-$C_6$ alkyl group, a $C_1$-$C_6$ alkoxy group, and a trihalo $C_1$-$C_6$ alkyl group.

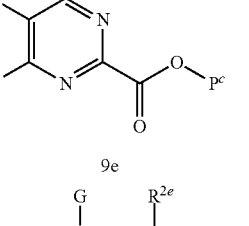

[Formula 8]

(1) Conversion of Compound 9e to Compound 10e

The conversion of compound 9e to compound 10e may be performed by conducting a similar, general coupling reaction as for the method described in step (6) of the above [production process 5].

Compound 10e may also be obtained by performing, to compound 9e, a coupling reaction using an alkyne compound (Sonogashira reaction) or a coupling reaction using an alkene compound (Mizoroki-Heck reaction) to obtain a corresponding alkyne compound or alkene compound, followed by performing a hydrogenation reaction.

(2) Conversion of Compound 10e to Compound 1e

The conversion of compound 10e to compound 1e may be performed by a similar, general deprotection reaction as for the method described in step (8) of the above [production process 1].

A compound of the present invention represented by general formula (I) can be formed into a pharmaceutically acceptable salt, if desired. A compound of the present invention represented by general formula (I) can be formed into a salt by having the compound react with an acid when it has a basic group, or by having the compound react with a base when it has an acidic group. Exemplary pharmaceutically acceptable salts (salts based on a basic group and salts based on an acidic group) are as described above.

In the present invention, the compound represented by general formula (I) encompasses compounds labeled with an atomic isotope or a radioisotope. Such labeled compounds can be produced by, for example, using a raw material labeled with an isotope instead of the raw material in the production method of the present invention.

A compound of the present invention represented by general formula (I) or a pharmaceutically acceptable salt thereof encompasses those in the form of a hydrate. Such hydrates may be produced by leaving the compound in the atmosphere or by having it recrystallized to absorb water molecules.

A compound of the present invention represented by general formula (I) or a salt thereof encompasses those in the form of a solvate. Such solvates may be produced by leaving the compound in a solvent or by having it recrystallized in a solvent to absorb a certain kind of solvent.

A compound of the present invention or a pharmacologically acceptable salt thereof can be administered in various forms. Examples of the dosage form may include oral administration with tablets, capsules, granules, emulsions, pills, powders, syrups (solutions) and the like, and parenteral administration with injections (intravenous, intramuscular, subcutaneous, or intraperitoneal administration), drip infusions, suppositories (rectal administration) and the like. Such various formulations can be prepared according to usual methods using a base component, as well as adjuvants that may normally be used in the field of preparing medicaments, such as excipients, binders, disintegrators, lubricants, correctives, solubilizers, suspending agents, and coating agents.

In the case of a tablet, examples of carriers that can be used include: excipients, such as lactose, sucrose, sodium chloride, glucose, urea, starch, calcium carbonate, kaolin, crystalline cellulose and silicic acid; binders, such as water, ethanol, propanol, simple syrup, glucose solutions, starch solutions, gelatin solutions, carboxymethylcellulose, shellac, methylcellulose, potassium phosphate and polyvinylpyrrolidone; disintegrators, such as dry starch, sodium alginate, agar powder, laminaran powder, sodium hydrogencarbonate, calcium carbonate, polyoxyethylene sorbitan fatty acid esters, sodium lauryl sulfate, monoglyceride stearate, starch and lactose; integration inhibitors, such as sucrose, stearin, cocoa butter and hydrogenated oil; absorption promoters, such as quaternary ammonium salts and sodium lauryl sulfate; moisturizing agents, such as glycerine and starch; adsorbents, such as starch, lactose, kaolin, bentonite and colloidal silicic acid; lubricants, such as purified talc, stearate salts, borax powder and polyethylene glycol; and others. Furthermore, tablets may be formed into those coated in usual manners, such as sugar-coated tablets, gelatin-coated tablets, enteric-coated tablets, film-coated tablets or double-layer tablets, and multilayered tablets, as necessary.

In the case of a pill, examples of carriers that can be used include: excipients, such as glucose, lactose, cocoa butter, starch, hydrogenated vegetable oil, kaolin and talc; binders, such as powdered gum arabic, powdered tragacanth, gelatin and ethanol; disintegrators, such as laminaran and agar; and others.

In the case of a suppository, a wide range of carriers conventionally known in this field can be used, and examples thereof include polyethylene glycol, cocoa butter, higher alcohols, higher alcohol esters, gelatin, semisynthetic glycerides, and the like.

In the case of an injection, the formulation may be prepared as a solution, an emulsion, or a suspension. Preferably, such solutions, emulsions, and suspensions are sterilized and are isotonic with blood. Solvents used for producing these solutions, emulsions, and suspensions are not particularly limited as long as they can be used as diluents for medical use, and examples thereof may include water, ethanol, propylene glycol, ethoxylated isostearyl alcohol, polyoxylated isostearyl alcohol, polyoxyethylene sorbitan fatty acid esters, and the like. In this case, a sufficient amount of sodium chloride, glucose, or glycerine for preparation of an isotonic solution may be included in the formulation, and usual solubilizers, buffering agents, soothing agents, and the like may also be included.

Furthermore, coloring agents, preservatives, flavors, flavoring agents, sweetening agents, and the like can be included in the above described formulation, as necessary. Moreover, other medical products may also be included.

The amount of an active component compound contained in the above described formulations is not particularly limited and appropriately selected within a wide range, but is usually 0.5 to 70% by weight in the total composition, preferably 1 to 30% by weight.

The dose varies depending on symptoms, age and the like of the patient (a warm-blooded animal, in particular, a human). However, it is desirable that, in the case of oral administration, a single dose from 0.01 mg/kg of body weight as the lower limit (preferably 0.1 mg/kg of body weight) to 500 mg/kg of body weight as the upper limit (preferably 100 mg/kg of body weight), and in the case of intravenous administration, a single dose from 0.001 mg/kg of body weight as the lower limit (preferably 0.01 mg/kg of body weight) to 50 mg/kg of body weight as the upper limit (preferably 10 mg/kg of body weight) is administered one to several times per day depending on symptoms.

Hereinafter, the present invention will be explained in more detail with reference to the Reference Examples, Examples, and Test Examples. However, the scope of the present invention shall not be limited to these examples.

Elution in column chromatography in the Reference Examples and Examples was performed under observation by thin layer chromatography (TLC). In the TLC observation, silica gel 60 F254 manufactured by Merck KGaA was used as a TLC plate; a solvent used as an eluting solvent in column chromatography was used as a developing solvent; and a UV detector was adopted in a detection method. In the column chromatography, an automatic purification apparatus from Yamazen Corp. or an automatic purification apparatus from Shokosha Co., Ltd. was appropriately used. The eluting solvent used was a solvent specified on the basis of a Reference Example or Example. The abbreviations used in the Reference Examples and Examples are as defined below.

mg: milligram, g: gram, µl: microliter, ml: milliliter, L: liter, M: molar concentration, and MHz: megahertz.

In the Examples below, nuclear magnetic resonance (hereinafter, referred to as $^1$H-NMR: 400 MHz) spectra were indicated by chemical shift δ values (ppm) determined with tetramethylsilane as a standard. Splitting patterns were indicated by s=singlet, d=doublet, t=triplet, q=quartet, sept=septet, m=multiplet, and br=broad.

Powder X-ray diffractometry was performed with a wavelength of CuKα at λ=1.54 angstroms using a reflection-type powder X-ray diffractometer (RINT-TTR III) manufactured by Rigaku Corp. Samples were measured using a non-reflecting sample holder (tube voltage: 50 kV, tube current: 300 mA, scanning range: 2 to 40°, scan rate: 20°/min, sampling width: 0.02°, rotational speed: 120 rpm).

In moisture measurement, a Karl Fischer moisture titrator (coulometric titration system MKC-610) manufactured by Kyoto Electronics Manufacturing Co., Ltd. was used (anolyte: HYDRANAL-Coulomat AG (Sigma-Aldrich Co. LLC), catholyte: HYDRANAL-Coulomat CG (Sigma-Aldrich Co. LLC)).

In thermal analysis (thermogravimetry differential thermal analysis: TG-DTA), TG/DTA6200 manufactured by Hitachi High-Tech Science Corp. was used (rate of temperature increase: 10° C./min, atmosphere gas: nitrogen, nitrogen gas flow rate: 200 mL/min).

Example 1

5-(2,4-Dichlorobenzyl)-4-(ethylamino)-6-methylpyrimidine-2-carboxylic acid hydrochloride

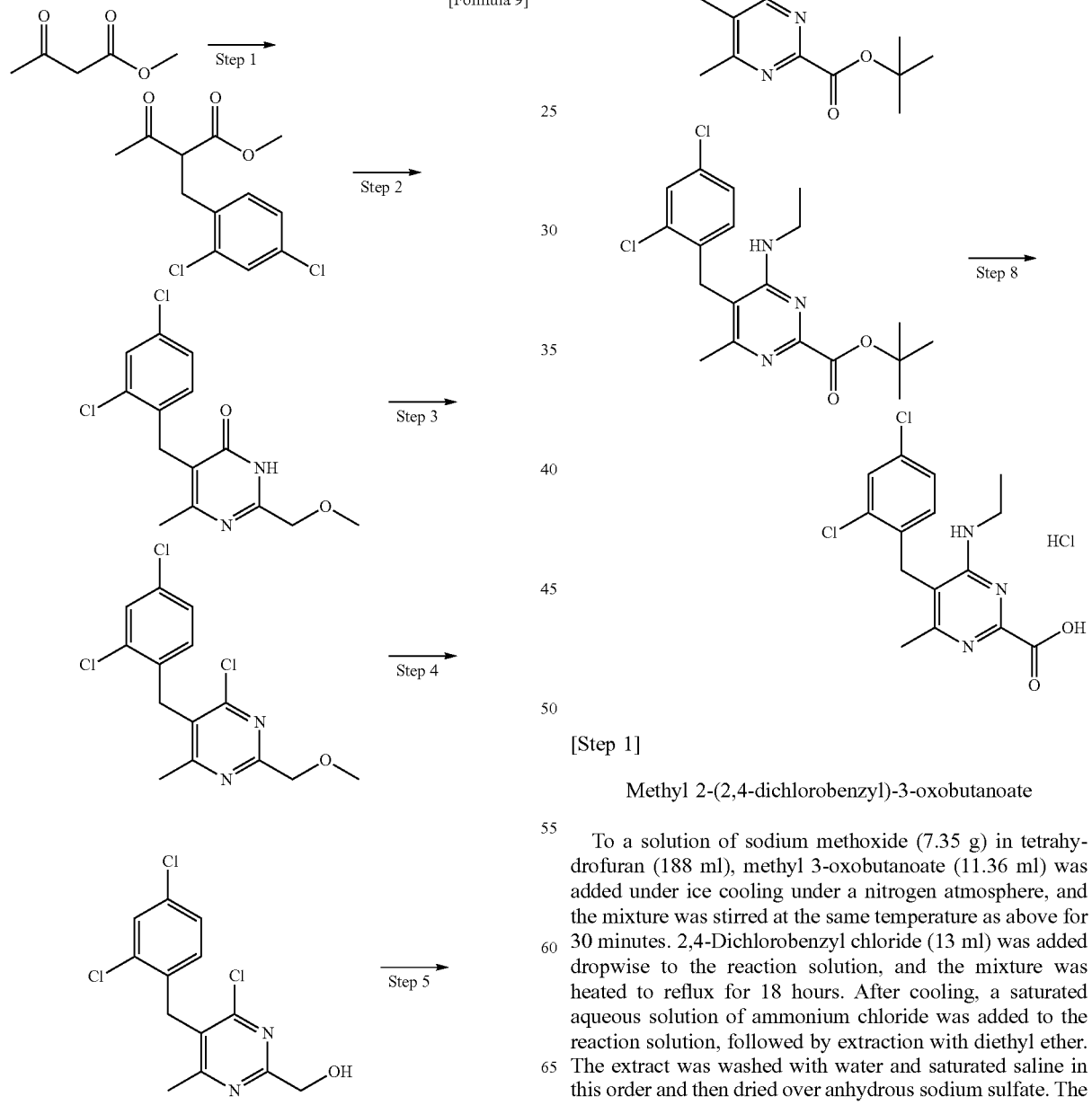

[Step 1]

Methyl 2-(2,4-dichlorobenzyl)-3-oxobutanoate

To a solution of sodium methoxide (7.35 g) in tetrahydrofuran (188 ml), methyl 3-oxobutanoate (11.36 ml) was added under ice cooling under a nitrogen atmosphere, and the mixture was stirred at the same temperature as above for 30 minutes. 2,4-Dichlorobenzyl chloride (13 ml) was added dropwise to the reaction solution, and the mixture was heated to reflux for 18 hours. After cooling, a saturated aqueous solution of ammonium chloride was added to the reaction solution, followed by extraction with diethyl ether. The extract was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (12.8 g).

$^1$H-NMR (CDCl$_3$) δ: 2.23 (3H, s), 3.23 (2H, s), 3.70 (3H, s), 3.91 (1H, dd, J=8.3, 6.7 Hz), 7.12-7.21 (2H, m), 7.37 (1H, d, J=2.0 Hz).

[Step 2]

5-(2,4-Dichlorobenzyl)-2-(methoxymethyl)-6-methylpyrimidin-4(3H)-one

To a solution of the compound (3.96 g) obtained in step 1 above in N,N-dimethylformamide (8 ml), the compound (4.4 g) obtained in step 1 of Reference Example 1 and 1,8-diazabicyclo[5.4.0]undec-7-ene (9 ml) were added, and the mixture was stirred at 70° C. for 7 hours under microwave irradiation. After cooling, the reaction solution was diluted with ice water. Ammonium chloride (7 g) was added to the aqueous solution, and the mixture was stirred for 30 minutes. The precipitate was collected by filtration, washed with water, and then dried under reduced pressure to obtain the title compound (4.53 g).

$^1$H-NMR (CDCl$_3$) δ: 2.21 (3H, s), 3.52 (3H, s), 3.95 (2H, s), 4.38 (2H, s), 6.96 (1H, d, J=8.3 Hz), 7.11 (1H, dd, J=8.3, 2.1 Hz), 7.38 (1H, d, J=2.1 Hz), 9.75 (1H, br s).

MS (m/z): 313 (M+H)$^+$.

[Step 3]

4-Chloro-5-(2,4-dichlorobenzyl)-2-(methoxymethyl)-6-methylpyrimidine

A solution of N-chlorosuccinimide (2.1 g) and triphenylphosphine (4.2 g) in 1,4-dioxane (160 ml) was stirred at room temperature for 30 minutes under a nitrogen atmosphere. A solution of the compound (1.07 g) obtained in step 2 above in 1,4-dioxane (160 ml) was added to the reaction solution, and the mixture was heated to reflux for 30 minutes. After cooling, the reaction solution was concentrated under reduced pressure, and the residue obtained was diluted with chloroform, washed with a saturated aqueous solution of sodium bicarbonate and water in this order, and then dried over anhydrous magnesium sulfate. The solvent was distilled off under reduced pressure, and the residue obtained was purified by silica gel column chromatography (n-hexane/ethyl acetate) to obtain the title compound (928 mg).

$^1$H-NMR (CDCl$_3$) δ: 2.46 (3H, s), 3.57 (3H, s), 4.21 (2H, s), 4.65 (2H, s), 6.58 (1H, d, J=8.4 Hz), 7.11 (1H, dd, J=8.4, 2.1 Hz), 7.46 (1H, d, J=2.1 Hz).

MS (m/z): 331 (M+H)$^+$.

[Step 4]

(4-Chloro-5-(2,4-dichlorobenzyl)-6-methylpyrimidin-2-yl)methanol

To a solution of the compound (927 mg) obtained in step 3 above in dichloromethane (5.6 ml), boron tribromide (1.0 M solution in dichloromethane, 2.8 ml) was added at −78° C. under an argon atmosphere, and the mixture was stirred for 4 hours under ice cooling. Methanol (113 μl) was added to the reaction solution, and then, the mixture was diluted with water, followed by extraction with chloroform. The extract was dried over anhydrous sodium sulfate. The solvent was distilled off under reduced pressure, and the residue obtained was dissolved in ethyl acetate. Then, n-hexane was added to the solution, and the precipitate was collected by filtration. The filtrate was concentrated under reduced pressure, and the residue obtained was purified by silica gel column chromatography (n-hexane/ethyl acetate). The compound obtained and the precipitate described above were combined to obtain the title compound (708 mg).

$^1$H-NMR (CDCl$_3$) δ: 2.46 (3H, s), 3.34-3.50 (1H, m), 4.21 (2H, br m), 4.80 (1H, br m), 6.59 (1H, d, J=8.4 Hz), 7.13 (1H, dd, J=8.4, 2.3 Hz), 7.47 (1H, d, J=2.3 Hz).

MS (m/z): 317 (M+H)$^+$.

[Step 5]

4-Chloro-5-(2,4-dichlorobenzyl)-6-methylpyrimidine-2-carboxylic acid

To a solution of the compound (700 mg) obtained in step 4 above in acetonitrile (11 ml), a sodium phosphate buffer solution (0.67 M, pH 6.7, 8.2 ml) and (2,2,6,6-tetramethylpiperidin-1-yl)oxyl (25 mg) were added, and the mixture was warmed to 35° C. Then, an aqueous sodium chlorite solution (2.0 M, 2.2 ml) and an aqueous sodium hypochlorite solution (0.26%, 1.3 ml) were added dropwise thereto over 3 hours. The mixture was stirred at 35° C. for 16 hours, then diluted with water under ice cooling, and rendered basic by the addition of a 2 M aqueous sodium hydroxide solution. Tert-butyl methyl ether was added to the mixed solution obtained to separate two layers. The aqueous layer was rendered acidic by the addition of 2 M hydrochloric acid under ice cooling, and the mixture was stirred for 30 minutes. The precipitate was collected by filtration, washed with water, and then dried under reduced pressure to obtain the title compound (693 mg).

$^1$H-NMR (DMSO-d$_6$) δ: 2.48 (3H, s), 4.24 (2H, s), 6.80 (1H, dd, J=8.4, 1.4 Hz), 7.29 (2H, dd, J=8.4, 2.2 Hz), 7.68-7.73 (1H, m).

MS (m/z): 331 (M+H)$^+$.

[Step 6]

Tert-butyl 4-chloro-5-(2,4-dichlorobenzyl)-6-methylpyrimidine-2-carboxylate

To a solution of the compound (500 mg) obtained in step 5 above in pyridine (3 ml), benzenesulfonyl chloride (233 μl) was added under a nitrogen atmosphere, and the mixed solution was stirred at room temperature for 1 hour. Tert-butyl alcohol (173 μl) was added to the reaction solution, and the mixture was stirred at room temperature for 2 hours. Benzenesulfonyl chloride (233 μl) was added again to the reaction solution, and the mixture was stirred for 1 hour. Then, tert-butyl alcohol (173 μl) was added thereto, and the mixture was stirred at room temperature for 1 hour. The reaction solution was poured into ice water, and the mixture was stirred for 10 minutes, followed by extraction with diethyl ether. The extract was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (431 mg).

$^1$H-NMR (CDCl$_3$) δ: 1.67 (9H, s), 2.53 (3H, s), 4.26 (2H, s), 6.53 (1H, d, J=8.3 Hz), 7.11 (1H, dd, J=8.3, 2.1 Hz), 7.47 (1H, d, J=2.1 Hz).

[Step 7]

Tert-butyl 5-(2,4-dichlorobenzyl)-4-(ethylamino)-6-methylpyrimidine-2-carboxylate To a solution of the compound (30 mg) obtained in step 6 above in 2-propanol (0.8 ml), an aqueous ethylamine solution (33%, 115 μl) was added, and the mixture was stirred at 95° C. for 3 hours. The reaction solution was concentrated under reduced pressure, and the residue obtained was purified by silica gel column chromatography (n-hexane/ethyl acetate) to obtain the title compound (22.7 mg).

$^1$H-NMR (CDCl$_3$) δ: 1.14 (3H, t, J=7.2 Hz), 1.65 (9H, s), 2.46 (3H, s), 3.48-3.57 (2H, m), 3.87 (2H, s), 4.33-4.56 (1H, br m), 6.68 (1H, d, J=8.4 Hz), 7.11 (1H, dd, J=8.4, 2.1 Hz), 7.46 (1H, d, J=2.1 Hz).

MS (m/z): 396 (M+H)$^+$.

[Step 8]

5-(2,4-Dichlorobenzyl)-4-(ethylamino)-6-methylpyrimidine-2-carboxylic acid hydrochloride To the compound (22.7 mg) obtained in step 7 above, a 4 M solution of hydrochloric acid in 1,4-dioxane (0.3 ml) was added, and the mixture was stirred at 50° C. for 1.5 hours. The reaction solution was concentrated under reduced pressure, and the residue obtained was dissolved in methanol. Diethyl ether was added to the solution, and the resulting precipitate was collected by filtration to obtain the title compound (13.7 mg).

$^1$H-NMR (DMSO-d$_6$) δ: 1.10 (3H, t, J=7.2 Hz), 2.20 (3H, s), 3.41-3.51 (2H, m), 3.93 (2H, s), 6.74 (1H, d, J=8.3 Hz), 7.30 (1H, dd, J=8.3, 2.3 Hz), 7.69 (1H, d, J=2.3 Hz).

MS (m/z): 340 (M+H)$^+$.

The following compounds were obtained by the same method as Example 1.

TABLE 1

| Example | Name and structure | Instrumental data |
| --- | --- | --- |
| 2 | 5-(2,4-Dichlorobenzyl)-4-methyl-6-(n-propylamino)pyrimidine-2-carboxylic acid hydrochloride | $^1$H-NMR (DMSO-d$_6$) δ: 0.81 (3H, t, J = 7.4 Hz), 1.48-1.60 (2H, m) 2.26 (3H, s) 3.40-3.48 (2H, m) 3.96 (2H, s) 6.81 (1H, d, J = 8.3 Hz) 7.30 (1H, dd, J = 8.3, 2.2 Hz) 7.70 (1H, d, J = 2.2 Hz) 8.28 (1H, br s). MS (m/z): 354 (M + H)$^+$. |
| 3 | 5-(2,4-Dichlorobenzyl)-4-(diethylamino)-6-methylpyrimidine-2-carboxylic acid hydrochloride | $^1$H-NMR (DMSO-d$_6$) δ: 1.13 (7 H, t, J = 6.8 Hz), 2.29 (3H, s), 3.37 (4 H, q, J = 6.8 Hz), 3.98 (2H, s), 7.06 (1H, d, J = 8.4 Hz), 7.39 (1H, dd, J = 8.4, 2.2 Hz), 7.74 (1H, d, J = 2.2 Hz). MS (m/z): 368 (M + H)$^+$. |
| 4 | (S)-4-((1-Amino-1-oxopropan-2-yl)amino)-5-(2,4-dichlorobenzyl)-6-methylpyrimidine-2-carboxylic hydrochloride | $^1$H-NMR (DMSO-d$_6$) δ: 1.32 (3H, d, J = 7.3 Hz), 2.28 (3H, s), 4.06 acid (2H, s), 4.76-4.87 (1H, m), 6.90 (1H, d, J = 8.4 Hz), 7.10 (1H, s), (1H, s), 7.69 (1H, d, J = 2.1 Hz), 7.98 (1H, br s). MS (m/z): 383 (M + H)$^+$. |

Example 5

5-(2,4-Dichlorobenzyl)-4-((3-isopropoxypropyl)amino)-6-methylpyrimidine-2-carboxylic acid

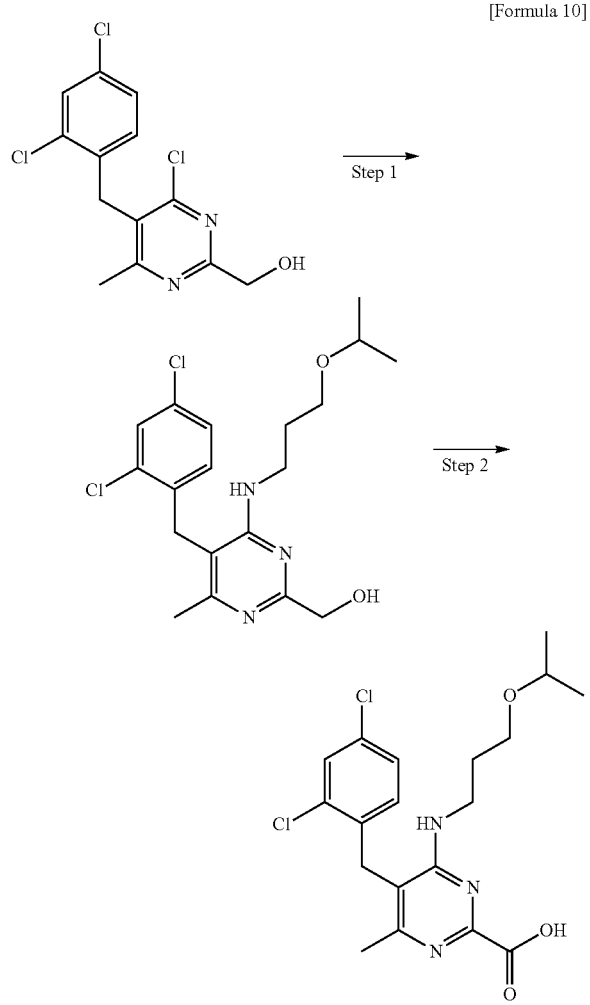

[Formula 10]

[Step 1]

(5-(2,4-Dichlorobenzyl)-4-((3-isopropoxypropyl)amino)-6-methylpyrimidin-2-yl)methanol To a solution of the compound (23 mg) obtained in step 4 of Example 1 in ethanol (1 ml), 3-isopropoxypropan-1-amine (51 µl) and N,N-diisopropylethylamine (126 µl) were added, and the mixture was stirred at 90° C. for 22 hours. The reaction solution was concentrated under reduced pressure, and the residue obtained was purified by silica gel column chromatography (chloroform/methanol) to obtain the title compound (25 mg), which was used in the next reaction as it was.

[Step 2]

5-(2,4-Dichlorobenzyl)-4-((3-isopropoxypropyl)amino)-6-methylpyrimidine-2-carboxylic acid To a solution of the compound (25 mg) obtained in step 1 above in 2-propanol (63 µl), chromium(VI) oxide (2.5 M solution in sulfuric acid, 25 µl) was added under ice cooling, and the mixture was stirred at room temperature for 1 hour. Acetone (628 µl) was added to the reaction solution, and the mixture was further stirred for 1 hour. The reaction solution was concentrated under reduced pressure, and then, the residue obtained was diluted with water, followed by extraction with ethyl acetate. The extract was washed with saturated saline and then dried over anhydrous magnesium sulfate. The solvent was distilled off under reduced pressure, and the residue obtained was purified by silica gel column chromatography (chloroform/methanol) to obtain the title compound (6.6 mg).

$^{1}$H-NMR (CDCl$_3$) δ: 0.98 (6H, d, J=6.1 Hz), 1.67-1.86 (2H, m), 2.40 (3H, s), 3.36-3.52 (3H, m), 3.58-3.75 (2H, m), 3.85 (2H, s), 6.00 (1H, br s), 6.64 (1H, d, J=7.9 Hz), 7.13 (1H, d, J=7.9 Hz), 7.45 (1H, s).

MS (m/z): 412 (M+H)$^{+}$.

Example 6

5-(2,4-Dichlorobenzyl)-4-((2-hydroxy-2-methylpropyl)amino)-6-methylpyrimidine-2-carboxylic acid

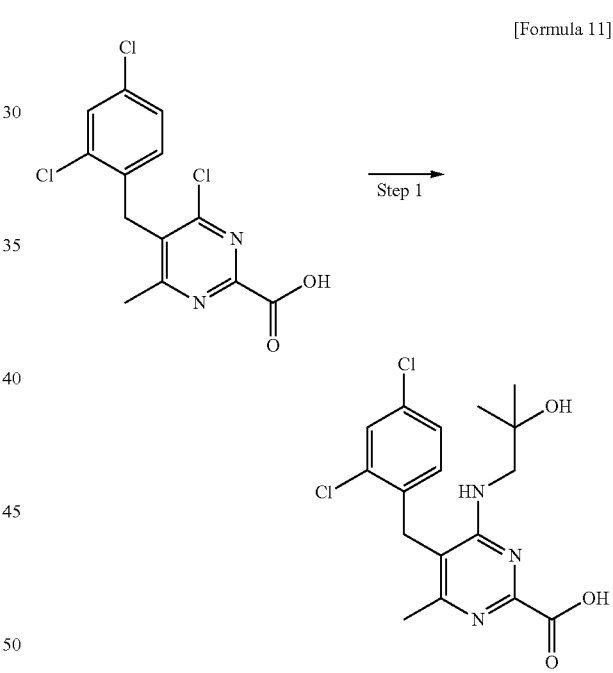

[Formula 11]

[Step 1]

5-(2,4-Dichlorobenzyl)-4-((2-hydroxy-2-methylpropyl)amino)-6-methylpyrimidine-2-carboxylic acid To a solution of the compound (28.6 mg) obtained in step 5 of Example 1 and 1-amino-2-methylpropan-2-ol (35 mg) in tetrahydrofuran (1 ml), N,N-diisopropylethylamine (0.15 ml) was added, and the mixture was stirred at 70° C. for 4 hours. The reaction solution was concentrated under reduced pressure, and the residue obtained was dissolved in chloroform. Acetic acid (0.15 ml) was added to the solution, followed by extraction with water. The extract was washed with ethyl acetate and then concentrated under reduced pressure. The residue obtained was purified by column chromatography (chloroform/methanol) using diol-modified silica gel to obtain the title compound (5.1 mg).

¹H-NMR (CDCl₃) δ: 1.06 (6H, s), 2.38 (3H, s), 3.31-3.51 (2H, br m), 3.86 (2H, s), 4.92 (1H, br s), 6.73 (1H, d, J=8.3 Hz), 7.06-7.15 (1H, m), 7.43 (1H, d, J=1.8 Hz).

MS (m/z): 384 (M+H)⁺.

Example 7

4-Amino-5-(2,4-dichlorobenzyl)-6-methylpyrimidine-2-carboxylic acid trifluoroacetate

[Formula 12]

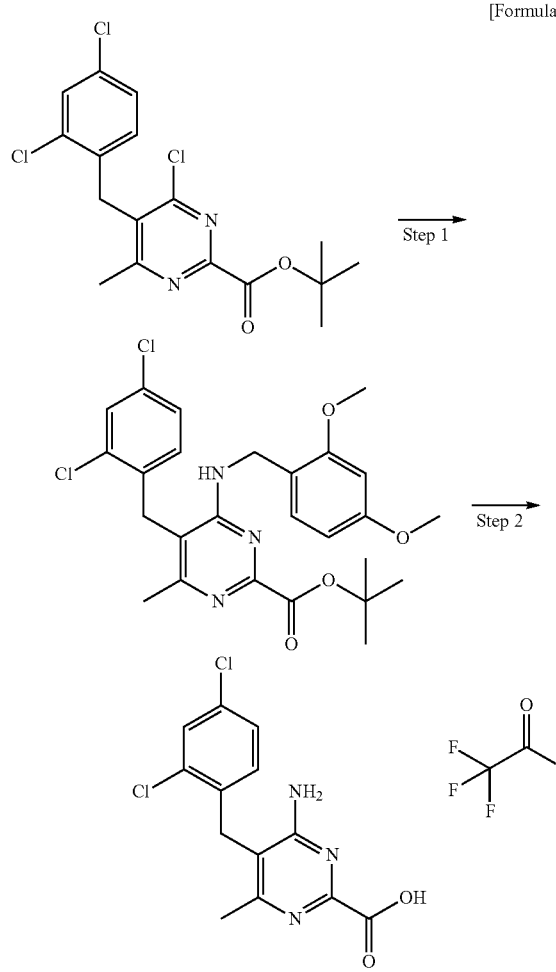

[Step 1]

tert-Butyl 5-(2,4-dichlorobenzyl)-4-((2,4-dimethoxybenzyl)amino)-6-methylpyrimidine-2-carboxylate To a solution of the compound (100 mg) obtained in step 6 of Example 1 in 2-propanol (1.3 ml), 2,4-dimethoxybenzylamine (78 µl) and triethylamine (0.18 ml) were added, and the mixture was stirred at 120° C. for 1 hour under microwave irradiation. After cooling, the reaction solution was diluted with water, followed by extraction with ethyl acetate. The extract was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (125 mg).

¹H-NMR (CDCl₃) δ: 1.68 (9H, s), 2.40 (3H, s), 3.57 (3H, s), 3.78 (3H, s), 3.83 (2H, s), 4.55 (2H, d, J=5.9 Hz), 5.11 (1H, t, J=5.9 Hz), 6.32-6.39 (2H, m), 6.52 (1H, d, J=8.4 Hz), 6.98 (1H, dd, J=8.3, 2.1 Hz), 7.28 (1H, d, J=8.3 Hz), 7.44 (1H, d, J=2.1 Hz).

MS (m/z): 518 (M+H)⁺.

[Step 2]

4-Amino-5-(2,4-dichlorobenzyl)-6-methylpyrimidine-2-carboxylic acid trifluoroacetate To a solution of the compound (125 mg) obtained in step 1 above in 1,4-dioxane (1.2 ml), a 4 M solution of hydrochloric acid in 1,4-dioxane (1.2 ml) was added, and the mixed solution was stirred at 50° C. for 24 hours. The reaction solution was concentrated under reduced pressure, and the residue obtained was dissolved in dichloromethane (1.2 ml). Trifluoroacetic acid (1.2 ml) was added to the solution, and the mixture was stirred at room temperature for 40 hours. The reaction solution was concentrated under reduced pressure, and ethyl acetate was added to the residue obtained. The precipitate was collected by filtration, washed with ethyl acetate, and then dried under reduced pressure to obtain the title compound (40.2 mg).

¹H-NMR (DMSO-d₆) δ: 2.21 (3H, s), 3.92 (2H, s), 6.02 (1H, s), 6.55 (1H, s), 6.79 (1H, d, J=8.3 Hz), 7.31 (1H, dd, J=8.3, 2.2 Hz), 7.67 (1H, d, J=2.2 Hz).

MS (m/z): 314 (M+H)⁺.

Example 8

4-((Carboxymethyl)amino)-5-(2,4-dichlorobenzyl)-6-methylpyrimidine-2-carboxylic acid hydrochloride

[Formula 13]

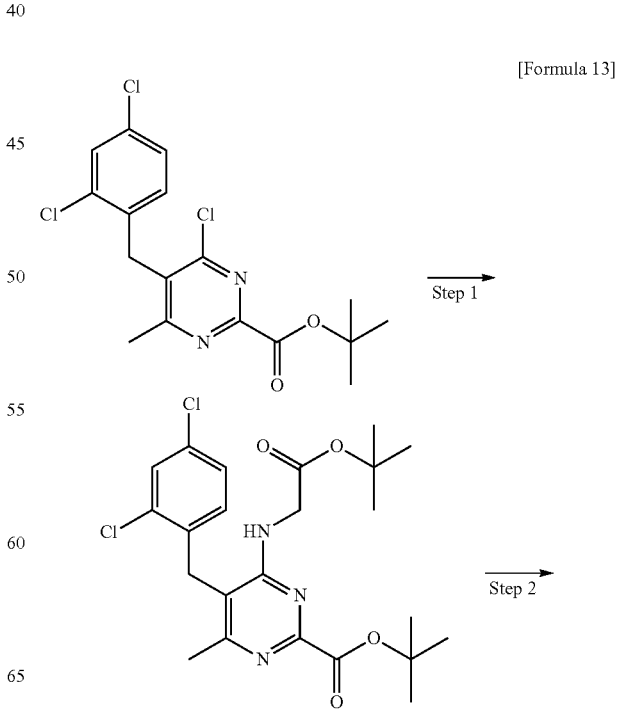

-continued

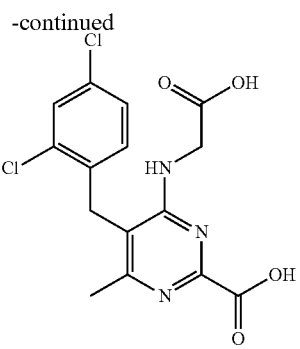

HCl

[Step 1]

tert-Butyl 4-((2-(tert-butoxy)-2-oxoethyl)amino)-5-(2,4-dichlorobenzyl)-6-methylpyrimidine-2-carboxylate To a solution of the compound (47 mg) obtained in step 6 of Example 1 and glycine tert-butyl ester hydrochloride (102 mg) in 2-propanol (0.6 ml), triethylamine (0.17 ml) was added, and the mixture was stirred at 100° C. for 3 hours under microwave irradiation. After cooling, the reaction solution was diluted with water, followed by extraction with ethyl acetate. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (42.1 mg).
$^1$H-NMR (CDCl$_3$) δ: 1.44 (9H, s), 1.64 (9H, s), 2.43 (3H, s), 3.94 (2H, s), 4.14 (2H, d, J=4.9 Hz), 5.09 (1H, t, J=4.9 Hz), 6.69 (1H, d, J=8.4 Hz), 7.10 (1H, dd, J=8.4, 2.1 Hz), 7.46 (1H, d, J=2.1 Hz).
MS (m/z): 482 (M+H)$^+$.

[Step 2]

4-((Carboxymethyl)amino)-5-(2,4-dichlorobenzyl)-6-methylpyrimidine-2-carboxylic acid hydrochloride To the compound (42 mg) obtained in step 1 above, a 4 M solution of hydrochloric acid in 1,4-dioxane (0.9 ml) was added, and the mixture was stirred at room temperature for 16 hours. The reaction solution was concentrated under reduced pressure, and the residue obtained was dissolved in methanol. Diethyl ether was added to the solution, and the resulting precipitate was collected by filtration to obtain the title compound (24.3 mg).
$^1$H-NMR (DMSO-d$_6$) δ: 2.27 (3H, s), 3.99 (2H, s), 4.13 (2H, d, J=5.8 Hz), 6.84 (1H, d, J=8.4 Hz), 7.28 (1H, dd, J=8.4, 2.1 Hz), 7.69 (1H, d, J=2.1 Hz), 8.34 (1H, br s).
MS (m/z): 370 (M+H)$^+$.

Example 9

5-(2,4-Dichlorobenzyl)-4-(ethylamino)-6-isopropylpyrimidine-2-carboxylic acid

[Formula 14]

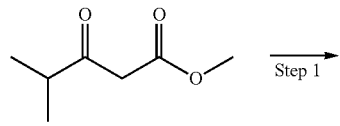
Step 1

-continued

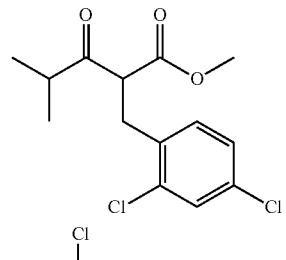
Step 2

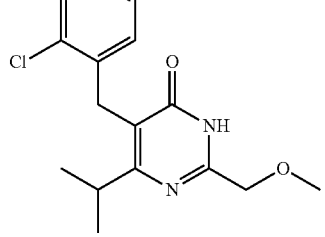
Step 3

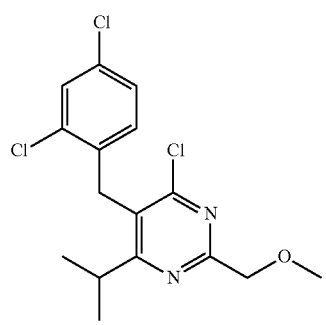
Step 4

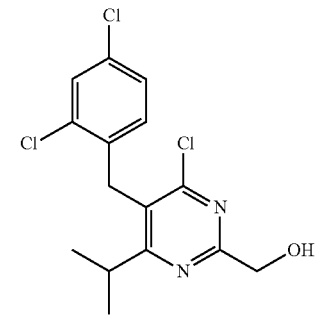
Step 5

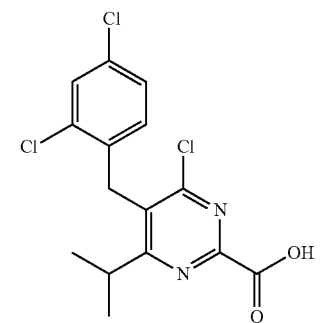
Step 6

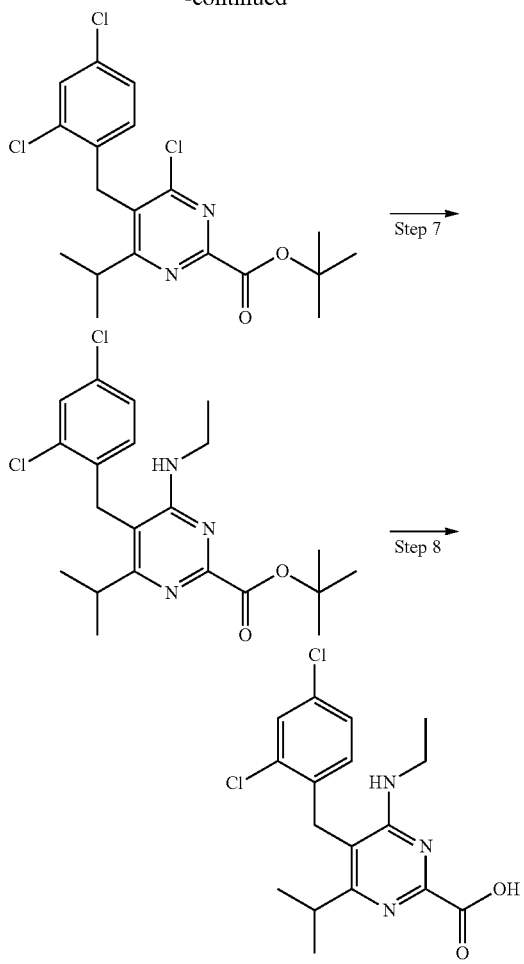

[Step 1]

Methyl 2-(2,4-dichlorobenzyl)-4-methyl-3-oxopentanoate

To a suspension of potassium tert-butoxide (867 mg) in tetrahydrofuran (20 ml), methyl 4-methyl-3-oxopentanoate (1.00 ml) and tert-butyl alcohol (67 µl) were added under ice cooling, and the mixture was stirred for 20 minutes under ice cooling. 2,4-Dichlorobenzyl chloride (0.97 ml) was added to the reaction solution, and then, the mixture was stirred at 70° C. for 3.5 hours. After cooling, a saturated aqueous solution of ammonium chloride was added to the reaction solution, followed by extraction with ethyl acetate. The extract was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (941 mg).

$^1$H-NMR (CDCl$_3$) δ: 0.91 (3H, d, J=7.0 Hz), 1.07 (3H, d, J=6.8 Hz), 2.70 (1H, spt, J=6.9 Hz), 3.17-3.28 (2H, m), 3.69 (3H, s), 4.12 (1H, t, J=7.5 Hz), 7.11-7.19 (2H, m), 7.36 (1H, d, J=1.9 Hz).

[Step 2]

5-(2,4-Dichlorobenzyl)-6-isopropyl-2-(methoxymethyl)pyrimidin-4(3H)-one

A solution of the compound (938 mg) obtained in step 1 above, the compound (578 mg) obtained in step 1 of Reference Example 1, and 1,8-diazabicyclo[5.4.0]undec-7-ene (1.40 ml) in N,N-dimethylformamide (8 ml) were stirred at 120° C. for 1 hour under microwave irradiation. After cooling, the reaction solution was stirred again at 120° C. for 1 hour under microwave irradiation. After cooling, water and a saturated aqueous solution of ammonium chloride were added to the reaction solution, followed by extraction with chloroform. The extract was washed with water and saturated saline in this order and then dried over anhydrous sodium sulfate. The solvent was distilled off under reduced pressure, and the residue obtained was purified by silica gel column chromatography (chloroform/methanol) to obtain the title compound (637 mg). 1H-NMR (CDCl$_3$) δ: 1.06 (6H, d, J=6.7 Hz), 2.90 (1H, spt, J=6.7 Hz), 3.52 (3H, s), 3.96 (2H, s), 4.41 (2H, s), 6.89 (1H, d, J=8.3 Hz), 7.09 (1H, dd, J=8.4, 2.1 Hz), 7.38 (1H, d, J=2.1 Hz), 9.80 (1H, br s).

MS (m/z): 341 (M+H)$^+$.

[Step 3]

4-Chloro-5-(2,4-dichlorobenzyl)-6-isopropyl-2-(methoxymethyl)pyrimidine

To a solution of the compound (625 mg) obtained in step 2 above in chloroform (10 ml), phosphoryl chloride (0.85 ml) was added, and the mixture was heated to reflux for 4 hours. After cooling, the reaction solution was poured into ice, and the mixture was rendered alkaline by the addition of a 2 M aqueous sodium hydroxide solution, followed by extraction with chloroform. The extract was washed with water and saturated saline in this order and then dried over anhydrous sodium sulfate. The solvent was distilled off under reduced pressure, and the residue obtained was purified by silica gel column chromatography (hexane/ethyl acetate) to obtain the title compound (443 mg).

$^1$H-NMR (CDCl$_3$) δ: 1.18 (6H, d, J=6.8 Hz), 3.02 (1H, spt, J=6.7 Hz), 3.58 (3H, s), 4.21 (2H, s), 4.66 (2H, s), 6.54 (1H, d, J=8.4 Hz), 7.11 (1H, dd, J=8.3, 2.2 Hz), 7.46 (1H, d, J=2.1 Hz).

MS (m/z): 359, 361 (M+H)$^+$.

[Step 4]

(4-Chloro-5-(2,4-dichlorobenzyl)-6-isopropylpyrimidin-2-yl)methanol

The title compound (392 mg) was obtained by the same method as step 4 of Example 1 using the compound (438 mg) obtained in step 3 above.

$^1$H-NMR (CDCl$_3$) δ: 1.19 (6H, d, J=6.7 Hz), 3.06 (1H, spt, J=6.7 Hz), 3.55 (1H, t, J=5.0 Hz), 4.23 (2H, s), 4.81 (2H, d, J=5.0 Hz), 6.55 (1H, d, J=8.3 Hz), 7.12 (1H, dd, J=8.4, 2.1 Hz), 7.47 (1H, d, J=2.1 Hz).

MS (m/z): 345, 347 (M+H)$^+$.

[Step 5]

4-Chloro-5-(2,4-dichlorobenzyl)-6-isopropylpyrimidine-2-carboxylic acid

To a solution of the compound (380 mg) obtained in step 4 above in acetonitrile (5 ml), (2,2,6,6-tetramethylpiperidin-1-yl)oxyl (12 mg) and a sodium phosphate buffer solution (0.67 M, pH 6.7, 4 ml) were added, and the mixture was warmed to 35° C. Then, an aqueous sodium chlorite solution (2.0 M, 1.10 ml) and an aqueous sodium hypochlorite solution (0.26%, 1.26 ml) were added dropwise thereto over 30 minutes. The mixture was stirred at 35° C. for 17 hours and then diluted with water under ice cooling, and a 2 M aqueous sodium hydroxide solution was added to the aqueous solution. The mixed solution obtained was rendered acidic by the addition of a 2 M aqueous hydrochloric acid solution, and the precipitate was collected by filtration, washed with water, and then dried to obtain the title compound (382 mg).

$^1$H-NMR (CDCl$_3$) δ: 1.24 (6H, d, J=6.7 Hz), 3.16 (1H, spt, J=6.7 Hz), 4.32 (2H, s), 6.50 (1H, d, J=8.3 Hz), 7.13 (1H, dd, J=8.3, 2.1 Hz), 7.49 (1H, d, J=2.1 Hz).

MS (m/z): 359, 361 (M+H)$^+$.

[Step 6]

tert-Butyl 4-chloro-5-(2,4-dichlorobenzyl)-6-isopropylpyrimidine-2-carboxylate To the compound (376 mg) obtained in step 5 above, a solution of 2-tert-butyl-1,3-diisopropylisourea (419 mg) in dichloromethane (5 ml) was added, and the mixture was stirred at room temperature for 45 minutes. 2-Tert-butyl-1,3-diisopropylisourea (209 mg) was further added to the reaction solution, and the mixture was stirred at room temperature for 18.5 hours. Insoluble matter precipitated in the reaction solution was removed by filtration. Then, the filtrate was concentrated under reduced pressure, and the residue obtained was purified by silica gel column chromatography (n-hexane/ethyl acetate) to obtain the title compound (347 mg).

$^1$H-NMR (CDCl$_3$) δ: 1.22 (6H, d, J=6.7 Hz), 1.66 (9H, s), 3.07 (1H, spt, J=6.7 Hz), 4.26 (2H, s), 6.50 (1H, d, J=8.4 Hz), 7.10 (1H, dd, J=8.3, 2.2 Hz), 7.47 (1H, d, J=2.1 Hz).

[Step 7]

Tert-butyl 5-(2,4-dichlorobenzyl)-4-(ethylamino)-6-isopropylpyrimidine-2-carboxylate To a solution of the compound (339 mg) obtained in step 6 above in 2-propanol (8 ml), an aqueous ethylamine solution (33%, 1.22 ml) was added, and the mixture was stirred at 90° C. for 7.5 hours. After cooling, the reaction solution was concentrated under reduced pressure, and the residue obtained was purified by silica gel chromatography (n-hexane/ethyl acetate) to obtain the title compound (290 mg).

$^1$H-NMR (CDCl$_3$) δ: 1.12 (3H, t, J=7.2 Hz), 1.23 (6H, d, J=6.8 Hz), 1.63 (9H, s), 3.05 (1H, spt, J=6.7 Hz), 3.50 (2H, qd, J=7.2, 5.4 Hz), 3.88 (2H, s), 4.34 (1H, t, J=5.0 Hz), 6.66 (1H, d, J=8.4 Hz), 7.10 (1H, dd, J=8.4, 2.1 Hz), 7.46 (1H, d, J=2.1 Hz) MS (m/z): 424 (M+H)$^+$.

[Step 8]

5-(2,4-Dichlorobenzyl)-4-(ethylamino)-6-isopropylpyrimidine-2-carboxylic acid To the compound (284 mg) obtained in step 7 above, a 4 M solution of hydrochloric acid in 1,4-dioxane (4 ml) was added, and the mixture was stirred at 50° C. for 2 hours. After cooling, the solvent in the reaction solution was distilled off under reduced pressure, and the residue obtained was diluted with chloroform (3 ml). Triethylamine (0.14 ml) was added to the solution, followed by purification by silica gel chromatography (chloroform/methanol) to obtain the title compound (189 mg).

$^1$H-NMR (CDCl$_3$) δ: 1.14 (3H, t, J=7.2 Hz), 1.24 (6H, d, J=6.8 Hz), 3.13 (1H, spt, J=6.7 Hz), 3.57 (2H, qd, J=7.2, 5.5 Hz), 3.93 (2H, s), 4.66 (1H, br s), 6.65 (1H, d, J=8.4 Hz), 7.15 (1H, dd, J=8.4, 2.1 Hz), 7.49 (1H, d, J=2.1 Hz).

MS (m/z): 368 (M+H)$^+$.

The following compounds were obtained by the same method as Example 9.

TABLE 2

| Example | Name and structure | Instrumental data |
|---|---|---|
| 10 | 4-Cyclopropyl-5-(2,4-dichlorobenzyl)-6-(ethylamino)pyrimidine-2-carboxylic acid | $^1$H-NMR (CDCl$_3$) δ: 0.98-1.07 (2H, m), 1.16 (3H, t, J = 7.2 Hz), 1.19-1.24 (2H, m), 1.93-2.03 (1H, m), 3.55 (2H, qd, J = 6.7 Hz), 4.04 (2H, s), 4.69 (1H, br s), 6.80 (1H, d, J = 8.3 Hz), 7.12-7.20 (1H, m), 7.48 (1H, d, J = 1.5 Hz). MS (m/z): 366 (M + H)$^+$. |
| 11 | 5-(2-Chlorobenzyl)-4-ethyl-6-(methylamino)pyrimidine-2-carboxylic acid | $^1$H-NMR (CDCl$_3$) δ: 1.26 (3H, t, J = 7.5 Hz), 2.77 (2H, q, J = 7.6 Hz), 3.05 (3H, d, J = 4.9 Hz), 3.98 (2H, s), 4.83 (1H, br s), 6.69-6.75 (1H, m), 7.16 (1H, td, J = 7.6, 1.3 Hz), 7.21-7.27 (1H, m), 7.47 (1H, dd, J = 8.0, 1.3 Hz). MS (m/z): 306 (M + H)$^+$. |

TABLE 2-continued

| Example | Name and structure | Instrumental data |
|---|---|---|
| 12 | 5-(2-Chlorobenzyl)-4-ethyl-6-(ethylamino)pyrimidine-2-carboxylic acid | $^1$H-NMR (CDCl$_3$) δ: 1.12 (3H, t, J = 7.2 Hz), 1.26 (3H, t, J = 7.6 Hz), 2.79 (2H, q, J = 7.5 Hz), 3.53 (2H, qd, J = 7.2, 5.4 Hz), 3.99 (2H, s), 4.73 (1H, br s), 6.74-6.79 (1H, m), 7.16 (1H, td, J = 7.5, 1.3 Hz), 7.20-7.30 (1H, m), 7.46 (1H, dd, J = 7.9, 1.3 Hz). MS (m/z): 320 (M + H)$^+$. |
| 13 | 5-(2-Chlorobenzyl)-4-isopropyl-6-(methylamino)pyrimidine-2-carboxylic acid | $^1$H-NMR (CDCl$_3$) δ: 1.25 (6H, d, J = 6.7 Hz), 3.06 (3H, d, J = 4.8 Hz), 3.16 (1H, spt, J = 6.7 Hz), 3.98 (2H, s), 4.78 (1H, br s), 6.66-6.73 (1H, m), 7.16 (1H, td, J = 7.6, 1.3 Hz), 7.20-7.30 (1H, m), 7.47 (1H, dd, J = 7.9, 1.3 Hz). MS (m/z): 320 (M + H)$^+$. |
| 14 | 5-(2-Chlorobenzyl)-4-(ethylamino)-6-isopropylpyrimidine-2-carboxylic acid | $^1$H-NMR (CDCl$_3$) δ: 1.12 (3H, t, J = 7.2 Hz), 1.26 (6H, d, J = 6.8 Hz), 3.19 (1H, spt, J = 6.7 Hz), 3.56 (2H, qd, J = 7.2, 5.4 Hz), 3.99 (2H, s), 4.71 (1H, br s), 6.69-6.77 (1H, m), 7.16 (1H, td, J = 7.6, 1.3 Hz), 7.21-7.28 (1H, m), 7.47 (1H, dd, J = 8.0, 1.3 Hz). MS (m/z): 334 (M + H)$^+$. |

Example 15

5-(2,4-Dichlorobenzyl)-4-ethyl-6-(ethylamino)pyrimidine-2-carboxylic acid

[Formula 15]

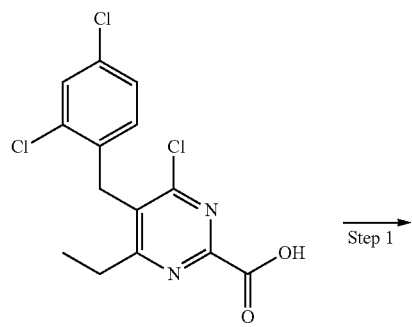

Step 1

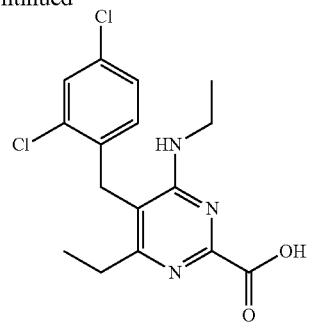

5-(2,4-Dichlorobenzyl)-4-ethyl-6-(ethylamino)pyrimidine-2-carboxylic acid

To a solution of 4-chloro-5-(2,4-dichlorobenzyl)-6-ethylpyrimidine-2-carboxylic acid (0.22 g) obtained by the same method as steps 1 to 5 of Example 9 in 2-propanol (6 ml), an aqueous ethylamine solution (6.7 M, 1 ml) was added, and the mixture was stirred at 90° C. for 24 hours. After cooling, the reaction solution was concentrated under reduced pressure, and the residue obtained was purified by silica gel column chromatography (chloroform/methanol). The eluted fraction was concentrated under reduced pressure, and water and a 1 M aqueous sodium hydroxide solution were added to the crude product obtained, followed by washing with diethyl ether. The aqueous layer was neutralized with 1 M hydrochloric acid, followed by extraction with chloroform. The extract was washed with saturated saline and then dried over anhydrous sodium sulfate. The solvent was distilled off under reduced pressure. Ethyl acetate was added to the residue obtained, and the resulting solid was collected by filtration to obtain the title compound (76 mg).

$^1$H NMR (CD$_3$OD) δ1.12 (3H, t, J=7.6 Hz), 1.18 (3H, t, J=7.2 Hz), 2.70 (2H, q, J=7.6 Hz), 3.72 (2H, q, J=7.2 Hz), 4.02 (2H, s), 6.83 (1H, d, J=8.3 Hz), 7.24 (1H, dd, J=8.4, 2.1 Hz), 7.56 (1H, d, J=2.1 Hz).

MS (m/z): 354 (M+H)$^+$.

Example 16

5-(2,4-Dichlorobenzyl)-4-(ethylamino)-6-(methoxymethyl)pyrimidine-2-carboxylic acid

[Formula 16]

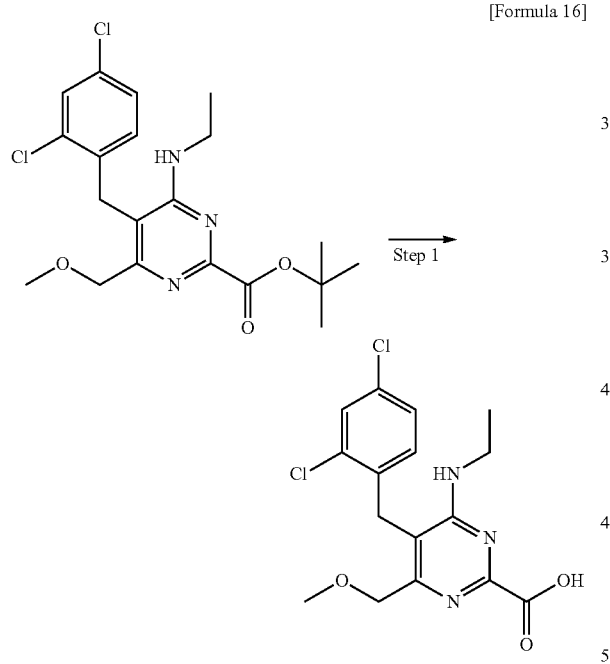

[Step 1]

5-(2,4-Dichlorobenzyl)-4-(ethylamino)-6-(methoxymethyl)pyrimidine-2-carboxylic acid To tert-butyl 5-(2,4-dichlorobenzyl)-4-(ethylamino)-6-ethoxymethyl)pyrimidine-2-carboxylate (363 mg) obtained by the same method as steps 1 to 7 of Example 1, a 4 M solution of hydrochloric acid in 1,4-dioxane (6 ml) was added, and the mixture was stirred overnight at room temperature. A 4 M solution of hydrochloric acid in 1,4-dioxane (2 ml) was further added to the reaction solution, and the mixture was stirred at 40° C. for 6 hours. The reaction solution was concentrated under reduced pressure, and the residue obtained was diluted with water. The pH of the aqueous solution was adjusted to approximately 5 by the gradual addition of a 1 M aqueous sodium hydroxide solution, followed by extraction with chloroform. The extract was dried over anhydrous sodium sulfate. The solvent was distilled off under reduced pressure, and the residue obtained was purified by column chromatography (chloroform/methanol) using diol-modified silica gel to obtain the title compound (278 mg).

$^1$H NMR (CDCl$_3$) δ:1.14 (3H, t, J=7.4 Hz), 3.39 (3H, s), 3.49-3.56 (2H, m), 4.05 (2H, s), 4.56 (2H, s), 4.81 (1H, br s), 6.83 (1H, d, J=8.0 Hz), 7.15 (1H, d, J=8.0 Hz), 7.48 (1H, s).

MS (m/z): 373 (M+H)$^+$.

Example 17

5-(2,4-Dichlorophenoxy)-4-methyl-6-(methylamino)pyrimidine-2-carboxylic acid

[Formula 17]

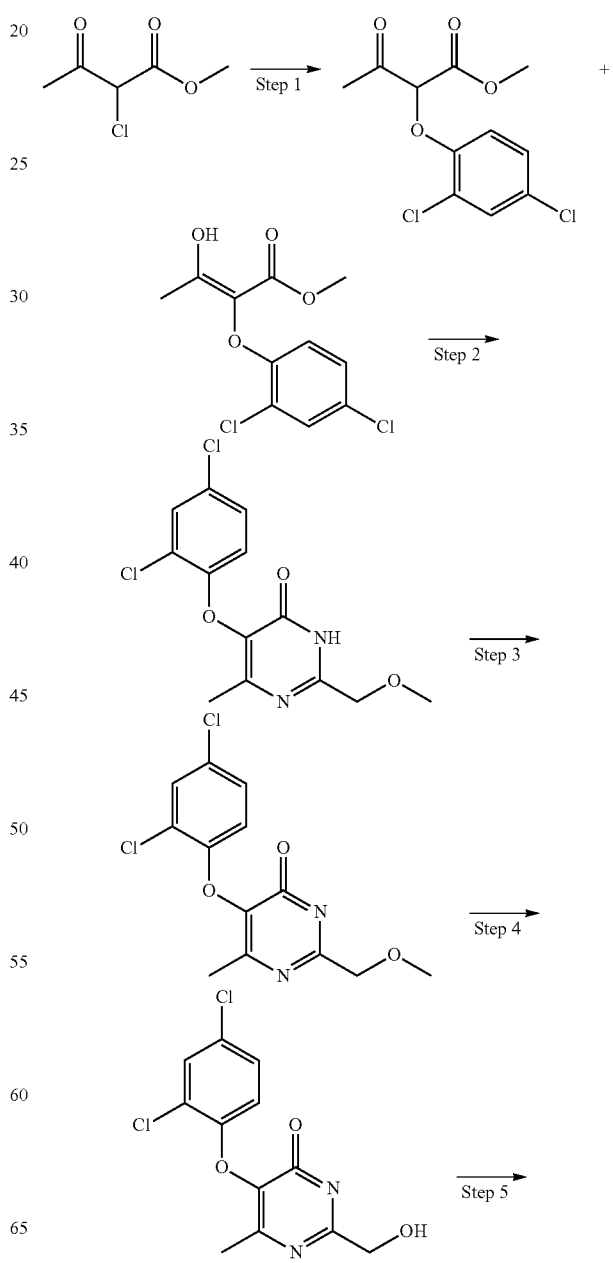

-continued

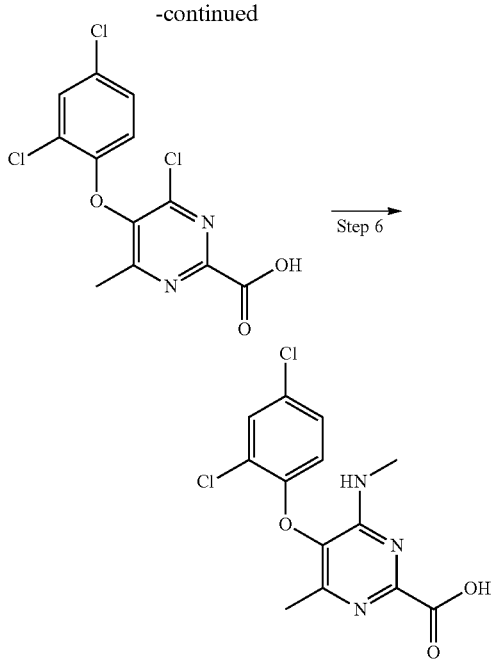

[Step 1]

Methyl 2-(2,4-dichlorophenoxy)-3-oxobutanoate, and methyl 2-(2,4-dichlorophenoxy)-3-hydroxy-2-butenoate To a suspension of 2,4-dichlorophenol (3.0 g) and cesium carbonate (6.0 g) in acetone (20 ml), methyl 2-chloro-3-oxobutanoate (2.2 ml) was added, and the mixture was heated to reflux for 2 hours. After cooling, the reaction solution was concentrated under reduced pressure, and the residue obtained was diluted with water. The aqueous solution was rendered acidic with 6 M hydrochloric acid, followed by extraction with ethyl acetate. The extract was washed with saturated saline and then dried over anhydrous sodium sulfate. The solvent was distilled off under reduced pressure, and the residue obtained was purified by silica gel column chromatography (n-hexane/chloroform) to obtain the title compounds (4.54 g) as a tautomeric mixture.

$^1$H-NMR (CDCl$_3$) δ: 1.99 (3H, s), 2.47 (1.5H, s), 3.74 (3H, s), 3.83 (1.5H, s), 5.02 (0.5H, s), 6.70 (1H, d, J=8.8 Hz), 6.78 (0.5H, d, J=8.9 Hz), 7.13 (1H, dd, J=8.8, 2.4 Hz), 7.15-7.20 (0.5H, m), 7.41 (1H, d, J=2.4 Hz), 7.43 (0.5H, d, J=2.5 Hz), 11.29 (1H, s).

[Step 2]

5-(2,4-Dichlorophenoxy)-2-(methoxymethyl)-6-methylpyrimidin-4(3H)-one

To a solution of the compound (1.66 g) obtained in step 1 above and the compound (0.746 g) obtained in step 1 of Reference Example 1 in N,N-dimethylformamide (3 ml), 1,8-diazabicyclo[5.4.0]undec-7-ene (1.8 ml) was added, and the mixture was stirred at 70° C. for 16 hours. After cooling, the reaction solution was diluted with water, and 2 M hydrochloric acid (3.3 ml) was added to the aqueous solution, followed by extraction with ethyl acetate. The extract was washed with saturated saline and then dried over anhydrous sodium sulfate. The solvent was distilled off under reduced pressure, and the residue obtained was purified by silica gel column chromatography (chloroform/methanol) to obtain the title compound (1.69 g).

$^1$H-NMR (CDCl$_3$) δ: 2.28 (3H, s), 3.52 (3H, s), 4.40 (2H, s), 6.62 (1H, d, J=8.8 Hz), 7.09 (1H, dd, J=8.8, 2.5 Hz), 7.43 (1H, d, J=2.5 Hz), 10.03 (1H, br s).

MS (m/z): 315 (M+H)$^+$.

[Step 3]

4-Chloro-5-(2,4-dichlorophenoxy)-2-(methoxymethyl)-6-methylpyrimidine

To a suspension of the compound (1.69 g) obtained in step 2 above in chloroform (12 ml), phosphoryl chloride (2.5 ml) was added, and the mixture was stirred at 100° C. for 30 minutes under microwave irradiation. After cooling, the reaction solution was poured into ice water, and the mixture was rendered basic by the addition of a 2 M aqueous sodium hydroxide solution, followed by extraction with chloroform. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (1.08 g).

$^1$H-NMR (CDCl$_3$) δ: 2.48 (3H, s), 3.57 (3H, s), 4.66 (2H, s), 6.37 (1H, d, J=8.8 Hz), 7.12 (1H, dd, J=8.8, 2.5 Hz), 7.50 (1H, d, J=2.5 Hz).

MS (m/z): 333 (M+H)$^+$.

[Step 4]

(4-Chloro-5-(2,4-dichlorophenoxy)-6-methylpyrimidin-2-yl)methanol

To a solution of the compound (1.08 g) obtained in step 3 above in dichloromethane (16 ml), boron tribromide (1.0 M solution in dichloromethane, 3.24 ml) was added at −78° C. under a nitrogen atmosphere, and the mixed solution was stirred at 0° C. for 4 hours. Methanol (1.3 ml) was added to the reaction solution, and then, the mixture was diluted with water, followed by extraction with chloroform. The extract was dried over anhydrous sodium sulfate. The solvent was distilled off under reduced pressure, and the residue obtained was purified by silica gel column chromatography (n-hexane/ethyl acetate) to obtain the title compound (927 mg).

$^1$H-NMR (CDCl$_3$) δ: 2.47 (3H, s), 3.27 (1H, t, J=5.3 Hz), 4.81 (2H, d, J=5.3 Hz), 6.38 (1H, d, J=8.8 Hz), 7.13 (1H, dd, J=8.8, 2.5 Hz), 7.51 (1H, d, J=2.5 Hz).

MS (m/z): 319 (M+H)$^+$.

[Step 5]

4-Chloro-5-(2,4-dichlorophenoxy)-6-methylpyrimidine-2-carboxylic acid

The title compound (918 mg) was obtained by the same method as step 5 of Example 1 using the compound (926 mg) obtained in step 4 above.

$^1$H-NMR (CDCl$_3$) δ: 2.60 (3H, s), 6.43 (1H, d, J=8.8 Hz), 7.17 (1H, dd, J=8.8, 2.5 Hz), 7.54 (1H, d, J=2.5 Hz).

MS (m/z): 333 (M+H)$^+$.

[Step 6]

5-(2,4-Dichlorophenoxy)-4-methyl-6-(methylamino)pyrimidine-2-carboxylic acid

To a solution of the compound (20 mg) obtained in step 5 above in 2-propanol (0.6 ml), an aqueous methylamine solution (12 M, 50 μl) was added, and the mixture was stirred at 70° C. for 4 hours in a sealed container. The reaction solution was concentrated under reduced pressure, and the residue obtained was diluted with water. The pH of the aqueous solution was adjusted to approximately 4 by the addition of 1 M hydrochloric acid, followed by extraction with chloroform. The extract was dried over anhydrous sodium sulfate. The solvent was distilled off under reduced pressure, and the residue obtained was dissolved in ethyl acetate. n-Hexane was added to the solution. The resulting precipitate was collected by filtration, then washed with n-hexane, and dried under reduced pressure to obtain the title compound (14.1 mg).

¹H-NMR (CDCl₃) δ: 2.26 (3H, s), 3.12 (3H, d, J=5.0 Hz), 5.30-5.43 (1H, br m), 6.46 (1H, d, J=8.8 Hz), 7.14 (1H, dd, J=8.8, 2.5 Hz), 7.51 (1H, d, J=2.5 Hz).

MS (m/z): 328 (M+H)⁺.

Example 18

5-((2-Chlorophenyl)thio)-4-(ethylamino)-6-methylpyrimidine-2-carboxylic acid

[Formula 18]

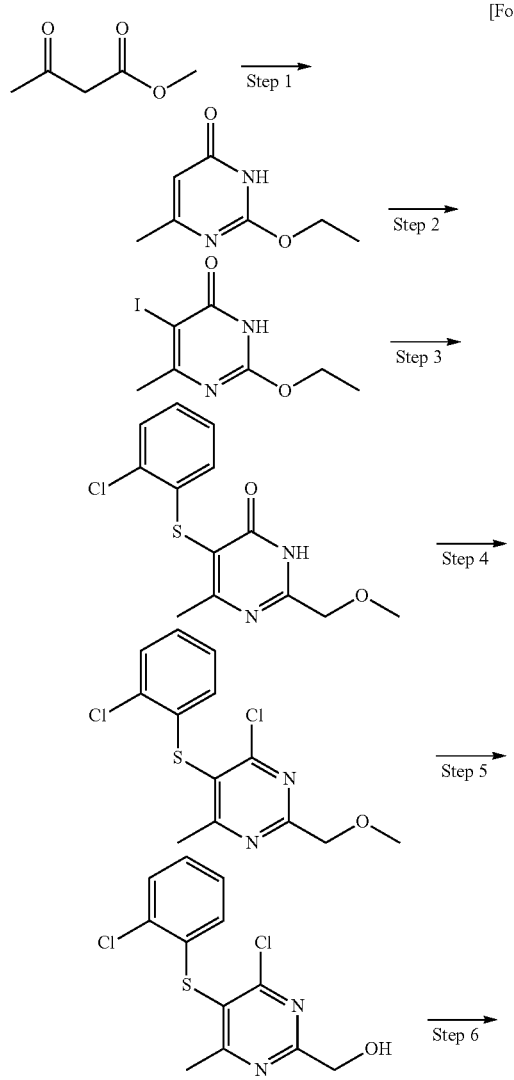

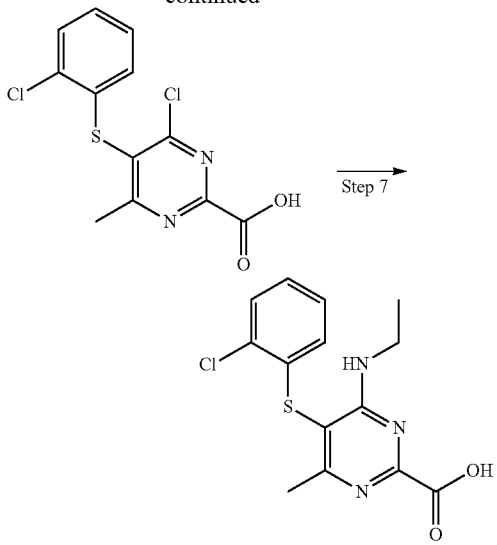

[Step 1]

2-(Methoxymethyl)-6-methylpyrimidin-4(3H)-one

To a suspension of sodium ethoxide (11.3 g) in ethanol (25.0 ml), methyl 3-oxobutanoate (7.41 ml) and the compound (8.58 g) obtained in step 1 of Reference Example 1 were added at room temperature, and the mixture was heated to reflux for 3 days. After cooling, the reaction solution was concentrated under reduced pressure, and the residue obtained was dissolved in water. The pH of the aqueous solution was adjusted to 5.5 by the addition of 6 M hydrochloric acid, followed by extraction with dichloromethane and ethyl acetate. The extract was washed with saturated saline and then dried over anhydrous sodium sulfate. The solvent was distilled off under reduced pressure, and the residue obtained was purified by silica gel column chromatography (chloroform/methanol) to obtain the title compound (7.38 g).

¹H-NMR (CDCl₃) δ: 2.28 (3H, s), 3.51 (3H, s), 4.38 (2H, s), 6.17 (1H, s).

MS (m/z): 155 (M+H)⁺.

[Step 2]

5-Iodo-2-(methoxymethyl)-6-methylpyrimidin-4(3H)-one

To the compound (5.33 g) obtained in step 1 above in a 1 M aqueous sodium hydroxide solution (57 ml), iodine (9.04 g) was added at room temperature, and the mixture was heated to reflux for 18 hours. The reaction solution was left standing at 0° C. for 1 hour, and then, water was added thereto, followed by extraction with chloroform. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (5.14 g).

¹H-NMR (CDCl₃) δ: 2.57 (3H, s), 3.52 (3H, s), 4.36 (2H, s), 9.75 (1H, br s).
MS (m/z): 281 (M+H)⁺.

[Step 3]

5-((2-Chlorophenyl)thio)-2-(methoxymethyl)-6-methylpyrimidin-4(3H)-one

To a solution of the compound (1.00 g) obtained in step 2 above in toluene (17.9 ml), 2-chlorothiophenol (608 μl), copper iodide (136 mg), Neocuproine (149 mg), and potassium carbonate (1.48 g) were added at room temperature, and the mixture was stirred overnight at 80° C. After cooling, water was added to the reaction solution, followed by extraction with chloroform. The extract was dried over anhydrous sodium sulfate. The solvent was distilled off under reduced pressure, and the residue obtained was purified by silica gel column chromatography (chloroform/methanol) to obtain the title compound (971 mg).
¹H-NMR (CDCl₃) δ: 2.52 (3H, s), 3.53 (3H, s), 4.42 (2H, s), 6.88 (1H, ddd, J=7.7, 1.9, 1.0 Hz), 7.04-7.13 (2H, m), 7.35 (1H, ddd, J=7.7, 3.0, 1.8 Hz), 9.93 (1H, br s).
MS (m/z): 297 (M+H)⁺.

[Step 4]

4-Chloro-5-((2-chlorophenyl)thio)-2-(methoxymethyl)-6-methylpyrimidine

The title compound (1.72 g) was obtained by the same method as step 3 of Example 17 using the compound (2.01 g) obtained in step 3 above.
¹H-NMR (CDCl₃) δ: 2.72 (3H, s), 3.61 (3H, s), 4.70 (2H, s), 6.68 (1H, dd, J=7.7, 1.7 Hz), 7.11-7.21 (2H, m), 7.43 (1H, dd, J=7.8, 1.6 Hz).
MS (m/z): 315 (M+H)⁺.

[Step 5]

(4-Chloro-5-((2-chlorophenyl)thio)-6-methylpyrimidin-2-yl)methanol

The title compound (2.12 g) was obtained by the same method as step 4 of Example 17 using the compound (2.57 g) obtained in step 4 above.
¹H-NMR (CDCl₃) δ: 2.72 (3H, s), 3.38 (1H, t, J=5.2 Hz), 4.85 (2H, d, J=5.4 Hz), 6.69 (1H, ddd, J=7.5, 2.3, 1.6 Hz), 7.13-7.23 (2H, m), 7.44 (1H, ddd, J=7.2, 2.0, 1.0 Hz).
MS (m/z): 301 (M+H)⁺.

[Step 6]

4-Chloro-5-((2-chlorophenyl)thio)-6-methylpyrimidine-2-carboxylic acid

The title compound (1.72 g) was obtained by the same method as step 5 of Example 1 using the compound (2.12 g) obtained in step 5 above.
¹H-NMR (CD₃OD) δ: 2.78 (3H, s), 6.94 (1H, dd, J=7.8, 1.6 Hz), 7.18-7.30 (2H, m), 7.47 (1H, dd, J=7.8, 1.4 Hz).
MS (m/z): 315 (M+H)⁺.

[Step 7]

5-((2-Chlorophenyl)thio)-4-(ethylamino)-6-methylpyrimidine-2-carboxylic acid

To a suspension of the compound (2.5 g) obtained in step 6 above in 2-propanol (80 ml), an aqueous ethylamine solution (33%, 5.8 ml) was added, and the mixture was stirred at 95° C. for 2 hours. After cooling, the reaction solution was concentrated under reduced pressure, and water and a saturated aqueous solution of potassium bisulfate were added to the residue obtained, followed by extraction with ethyl acetate. The extract was washed with water and saturated saline in this order and then dried over anhydrous sodium sulfate. The solvent was distilled off under reduced pressure, and ethyl acetate/n-hexane was added to the residue obtained. The precipitate was collected by filtration to obtain the title compound (0.97 g).
¹H-NMR (CDCl₃) δ: 1.19 (3H, t, J=7.3 Hz), 2.59 (3H, s), 3.54-3.61 (2H, m), 6.22 (1H, br s), 6.59 (1H, dd, J=7.5, 2.3 Hz), 7.09-7.19 (2H, m), 7.42 (1H, dd, J=7.5, 1.5 Hz).
MS (m/z): 324 (M+H)⁺.

The following compounds were obtained by the same method as Example 18.

TABLE 3

| Example | Name and Structure | Instrumental data |
|---|---|---|
| 19 | 5-((2-Chlorophenyl)thio)-4-(ethylamino)-6-isopropylpyrimidine-2-carboxylic acid | ¹H-NMR (CD₃OD) δ: 1.09 (3H, t, J = 7.2 Hz), 1.15 (6H, d, J = 6.8 Hz), 3.51 (2H, q, J = 7.2 Hz), 3.62 (1H, spt, J = 6.8 Hz), 6.58-6.66 (1H, m), 7.07-7.17 (2H, m), 7.36-7.44 (1H, m). MS (m/z): 352 (M + H)⁺. |
| 20 | 5-((2-Chlorophenyl)thio)-4-ethyl-6-(ethylamino)pyrimidine-2-carboxylic acid | ¹H-NMR (CD₃OD) δ: 1.14 (3H, t, J = 7.2 Hz), 1.18 (3H, t, J = 6.8 Hz), 2.96 (2H, q, J = 7.5 Hz), 3.67 (2H, q, J = 7.1 Hz), 6.73-6.80 (1H, m), 7.17-7.24 (2H, m), 7.43-7.49 (1H, m). MS (m/z): 338 (M + H)⁺. |
| 21 | 5-((2,4-Dichlorophenyl)thio)-4-ethyl-6-(ethylamino)pyrimidine-2-carboxylic acid | ¹H-NMR (CD₃OD) δ: 1.09 (6H, t, J = 6.4 Hz), 2.92 (2H, br s), 3.48-3.71 (2H, m), 6.58 (1H, d, J = 6.7 Hz), 7.15 (1H, d, J = 5.7 Hz), 7.50 (1H, s). MS (m/z): 372 (M + H)⁺. |

Example 22

5-((2-Chlorophenyl)thio)-4-(ethylamino)-6-methylpyrimidine-2-carboxylic acid hydrochloride

[Formula 19]

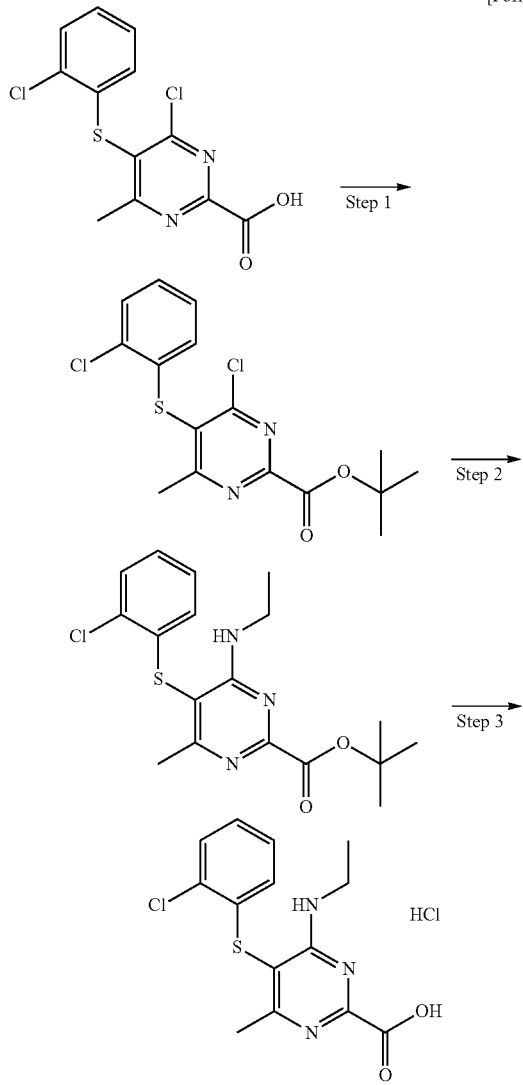

[Step 1]

tert-Butyl 4-chloro-5-((2-chlorophenyl)thio)-6-methylpyrimidine-2-carboxylate To a solution of the compound (200 mg) obtained in step 6 of Example 18 in N,N-dimethylacetamide (2.0 ml), tert-butyl alcohol (300 µl) and N-methylimidazole (250 µl) were added at room temperature, and the mixture was stirred at 40° C. p-Toluenesulfonyl chloride (242 mg) was added to the reaction solution, and the mixture was stirred at 40° C. for 20 minutes. Water was added to the reaction solution, followed by extraction with ethyl acetate. The extract was washed with a saturated aqueous solution of sodium bicarbonate and then dried over anhydrous sodium sulfate. The solvent was distilled off under reduced pressure, and the residue obtained was purified by silica gel column chromatography (n-hexane/ethyl acetate) to obtain the title compound (156 mg).

$^1$H-NMR (CDCl$_3$) δ: 1.66 (9H, s), 2.72 (3H, s), 6.75 (1H, dd, J=7.8, 1.7 Hz), 7.09-7.22 (2H, m), 7.42 (1H, dd, J=7.8, 1.4 Hz).

[Step 2]

tert-Butyl 5-((2-chlorophenyl)thio)-4-(ethylamino)-6-methylpyrimidine-2-carboxylate To a solution of the compound (1.63 g) obtained in step 1 above in 2-propanol (53.0 ml), an aqueous ethylamine solution (33%, 3.66 ml) was added at room temperature, and the mixture was stirred at 95° C. for 2 hours. After cooling, the reaction solution was concentrated under reduced pressure, and the residue obtained was diluted with water. 2 M hydrochloric acid was added to the aqueous solution, followed by extraction with chloroform. The extract was dried over anhydrous sodium sulfate. The solvent was distilled off under reduced pressure, and the residue obtained was purified by silica gel column chromatography (n-hexane/ethyl acetate) to obtain the title compound (1.84 g).

$^1$H-NMR (CDCl$_3$) δ: 1.16 (3H, t, J=7.3 Hz), 1.65 (9H, s), 2.56 (3H, s), 3.55 (2H, qd, J=7.7, 5.7 Hz), 5.99 (1H, t, J=4.9 Hz), 6.58 (1H, dd, J=7.7, 1.7 Hz), 7.03-7.15 (2H, m), 7.39 (1H, dd, J=7.7, 1.6 Hz).

MS (m/z): 380 (M+H)$^+$.

[Step 3]

5-((2-Chlorophenyl)thio)-4-(ethylamino)-6-methylpyrimidine-2-carboxylic acid hydrochloride To the compound (1.83 g) obtained in step 2 above, a 4 M solution of hydrochloric acid in 1,4-dioxane (24.1 ml) was added at room temperature, and the mixture was stirred at room temperature for 17 hours. The reaction solution was concentrated under reduced pressure, and the residue obtained was dissolved in methanol. Diethyl ether was added to the solution, and the resulting precipitate was collected by filtration to obtain the title compound (1.53 g).

$^1$H-NMR (CD$_3$OD) δ: 1.19 (3H, t, J=7.2 Hz), 2.63 (3H, s), 3.71 (2H, q, J=7.2 Hz), 6.86-6.92 (1H, m), 7.20-7.29 (2H, m), 7.50 (1H, ddd, J=7.9, 2.3, 1.4 Hz).

MS (m/z): 324 (M+H)$^+$.

The following compounds were obtained by the same method as Example 22.

TABLE 4

| Example | Name and Structure | Instrumental data |
| --- | --- | --- |
| 23 | 4-Methyl-6-(methylamino)-5-(phenylthio)pyrimidine-2-carboxylic acid hydrochloride | $^1$H-NMR (CD$_3$OD) δ: 2.67 (3H, s), 3.17 (3H, s), 7.20-7.29 (3H, m), 7.30-7.37 (2H, m). MS (m/z): 276 (M + H)$^+$. |

TABLE 4-continued

| Example | Name and Structure | Instrumental data |
|---|---|---|
| 24 | 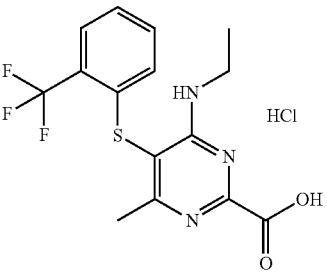<br>4-(Ethylamino)-6-methyl-5-((2-(trifluoromethyl)phenyl)thio)pyrimidine-2-carboxylic acid hydrochloride | $^1$H-NMR (CD$_3$OD) δ: 1.24 (3H, t, J = 7.2 Hz), 2.59 (3H, s), 3.75 (2H, q, J = 7.2 Hz), 7.07 (1H, d, J = 7.9 Hz), 7.39-7.47 (1H, m), 7.47-7.55 (1H, m), 7.75-7.85 (1H, m). MS (m/z): 358 (M + H)$^+$. |
| 25 | 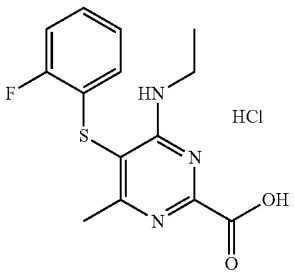<br>4-(Ethylamino)-5-((2-fluorophenyl)thio)-6-methylpyrimidine-2-carboxylic acid hydrochloride | $^1$H-NMR (CD$_3$OD) δ: 1.15 (3H, t, J = 7.2 Hz), 2.58 (3, s), 3.68 (2H, q, J = 7.0 Hz), 6.99-7.22 (3H, m), 7.22-7.34 (1H, m). MS (m/z): 308 (M + H)$^+$. |
| 26 | 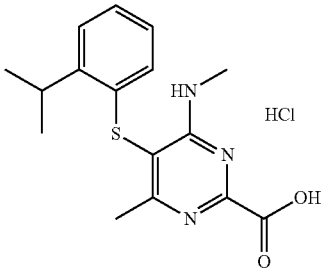<br>5-((2-Isopropylphenyl)thio)-4-methyl-6-(methylamino)pyrimidine-2-carboxylic acid hydrochloride | $^1$H-NMR (CD$_3$OD) δ: 1.34 (6H, d, J = 6.8 Hz), 2.56 (3H, s), 3.19 (3H, s), 3.47 (1H, spt, J = 6.7 Hz), 6.75 (1H, dd, J = 7.7, 1.5 Hz), 7.08 (1H, ddd, J = 7.7, 7.7, 1.5 Hz), 7.23 (1H, ddd, J = 7.0, 7.0, 1.0 Hz), 7.39 (1H, dd, J = 7.9, 1.0 Hz). MS (m/z): 318 (M + H)$^+$. |
| 27 | 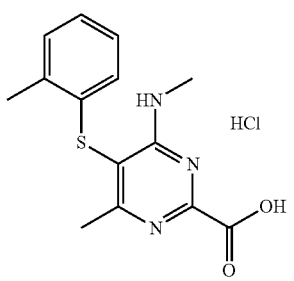<br>4-Methyl-6-(methylamino)-5-(o-tolylthio)pyrimidine-2-carboxylic acid hydrochloride | $^1$H-NMR (CD$_3$OD) δ: 2.46 (3H, s), 2.59 (3H, s), 3.17 (3H, s), 6.75 (1H, dd, J = 7.7, 1.3 Hz), 7.06-7.18 (2H, m), 7.26 (1H, d, J = 7.2 Hz). MS (m/z): 290 (M + H)$^+$. |
| 28 | 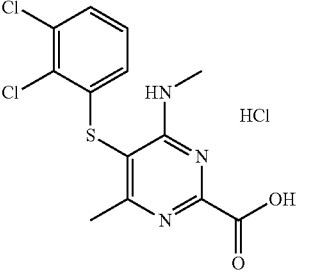<br>5-((2,3-Dichlorophenyl)thio)-4-methyl-6-(methylamino)pyrimidine-2-carboxylic acid hydrochloride | $^1$H-NMR (CD$_3$OD) δ: 2.64 (3H, s), 3.14 (3H, s), 6.78 (1H, d, J = 6.7 Hz), 7.16-7.22 (1H, m), 7.42 (1H, d, J = 8.2 Hz). MS (m/z): 344 (M + H)$^+$. |
| 29 | 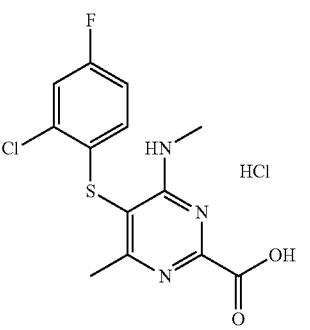<br>5-((2-Chloro-4-fluorophenyl)thio)-4-methyl-6-(methylamino)pyrimidine-2-carboxylic acid hydrochloride | $^1$H-NMR (CD$_3$OD) δ: 2.62 (3H, s), 3.17 (3H, s), 6.88-6.97 (1H, m), 7.00-7.07 (1H, m), 7.35-7.41 (1H, m). MS (m/z): 328 (M + H)$^+$. |
| 30 | 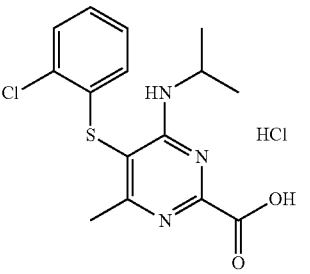<br>5-((2-Chlorophenyl)thio)-4-(isopropylamino)-6-methylpyrimidine-2-carboxylic acid hydrochloride | $^1$H-NMR (CD$_3$OD) δ: 1.23 (6H, d, J = 6.5 Hz), 2.63 (3H, s), 4.74 (1H, spt, J = 6.6 Hz), 6.94 (1H, ddd, J = 7.0, 3.4, 1.8 Hz), 7.21-7.30 (2H, m), 7.50 (1H, ddd, J = 7.5, 2.3, 1.5 Hz). MS (m/z): 338 (M + H)$^+$. |
| 31 | 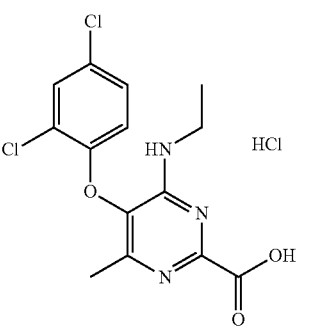<br>5-(2,4-Dichlorophenoxy)-4-(ethylamino)-6-methylpyrimidine-2-carboxylic acid hydrochloride | $^1$H-NMR (DMSO-d$_6$) δ: 1.10 (3H, t, J = 7.2 Hz), 2.04 (3H, s), 3.37-3.47 (2H, m), 6.67 (1H, d, J = 8.9 Hz), 7.30 (1H, dd, J = 8.9, 2.5 Hz), 7.70-7.79 (2H, m). MS (m/z): 342 (M + H)$^+$. |

Example 32

5-(2,4-Dichlorobenzyl)-4-methoxy-6-methylpyrimidine-2-carboxylic acid

[Formula 20]

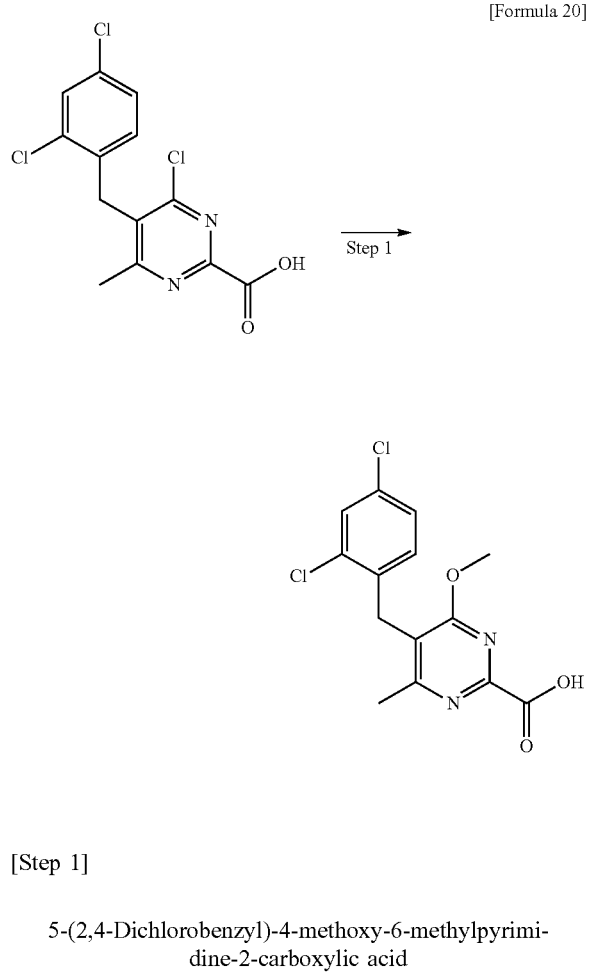

[Step 1]

5-(2,4-Dichlorobenzyl)-4-methoxy-6-methylpyrimidine-2-carboxylic acid

A suspension of the compound (21 mg) obtained in step 5 of Example 1 and cesium carbonate (42 mg) in methanol (0.6 ml) was stirred at room temperature for 15 hours. The reaction solution was concentrated under reduced pressure, and the residue obtained was diluted with water and then rendered acidic with 2 M hydrochloric acid. The precipitate was collected by filtration, washed with water, and then dried under reduced pressure to obtain the title compound (18.4 mg).

$^1$H-NMR (CDCl$_3$) δ: 2.47 (3H, s), 4.07-4.12 (5H, m), 6.62 (1H, d, J=8.3 Hz), 7.11 (1H, dd, J=8.3, 2.3 Hz), 7.44 (1H, d, J=2.3 Hz).

MS (m/z): 327 (M+H)$^+$.

The following compounds were obtained by the same method as Example 32.

TABLE 5

| Example | Name and Structure | Instrumental data |
|---|---|---|
| 33 | 5-(2,4-Dichlorobenzyl)-4-ethoxy-6-methylpyrimidine-2-carboxylic acid | $^1$H-NMR (CDCl$_3$) δ: 1.34 (3H, t, J = 7.1 Hz), 2.48 (3H, s), 4.08 (2H, s), 4.54 (2H, q, J = 7.1 Hz), 6.68 (1H, d, J = 8.4 Hz), 7.11 (1H, dd, J = 8.4, 2.1 Hz), 7.43 (1H, d, J = 2.1 Hz). MS (m/z): 341 (M + H)$^+$. |
| 34 | 5-(2,4-Dichlorophenoxy)-4-methoxy-6-methylpyrimidine-2-carboxylic acid | $^1$H-NMR (CDCl$_3$) δ: 2.51 (3H, s), 4.06 (3H, s), 6.44 (1H, d, J = 8.8 Hz), 7.12 (1H, dd, J = 8.8, 2.5 Hz), 7.48 (1H, d, J = 2.5 Hz). MS (m/z): 329 (M + H)$^+$. |
| 35 | 5-(2,4-Dichlorophenoxy)-4-ethoxy-6-methylpyrimidine-2-carboxylic acid | $^1$H-NMR (DMSO-d$_6$) δ: 1.14 (3H, t, J = 7.0 Hz), 2.36 (3H, s), 4.39 (2H, d, J = 7.0 Hz), 6.86 (1H, d, J = 8.8 Hz), 7.28 (1H, dd, J = 8.8, 2.5 Hz), 7.75 (1H, d, J = 2.5 Hz). MS (m/z): 343 (M + H)$^+$. |
| 36 | 5-((2,4-Dichlorophenyl)thio)-4-methoxy-6-methylpyrimidine-2-carboxylic acid | $^1$H-NMR (CD$_3$OD) δ: 2.66 (3H, s), 4.00 (3H, s), 6.84 (1H, d, J = 8.7 Hz), 7.20 (1H, dd, J = 8.5, 2.3 Hz), 7.51 (1H, d, J = 2.3 Hz). MS (m/z): 345 (M + H)$^+$. |

65

TABLE 5-continued

| Example | Name and Structure | Instrumental data |
|---------|--------------------|-------------------|
| 37 | 5-((2,4-Dichlorophenyl)thio)-4-ethyl-6-methoxypyrimidine-2-carboxylic acid | $^1$H-NMR (CD$_3$OD) δ: 1.21 (3H, t, J = 7.2 Hz), 2.99 (2H, q, J = 7.2 Hz), 3.98 (3H, s), 6.68 (1H, d, J = 8.5 Hz), 7.16 (1H, dd, J = 8.6, 2.2 Hz), 7.47 (1H, d, J = 2.3 Hz). MS (m/z): 359 (M + H)$^+$. |

Example 38

5-(2-Chlorobenzyl)-4-methoxy-6-methylpyrimidine-2-carboxylic acid

[Formula 21]

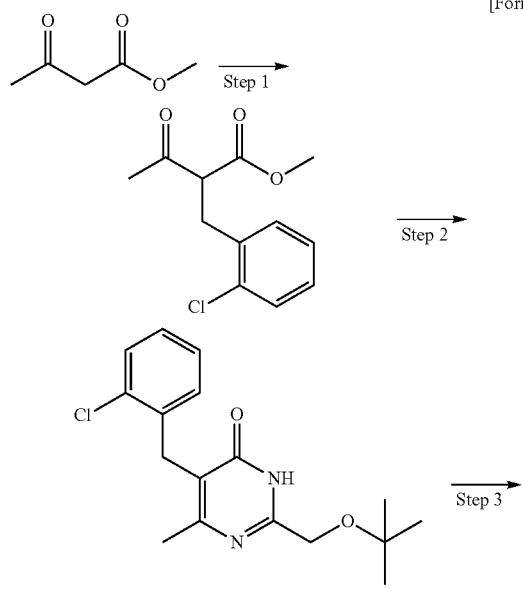

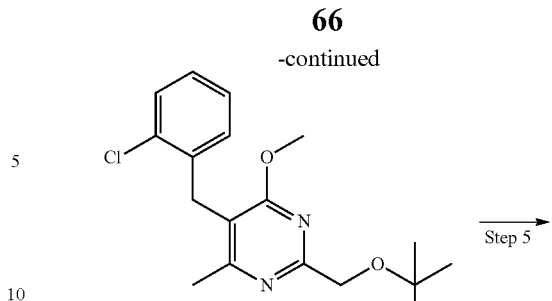

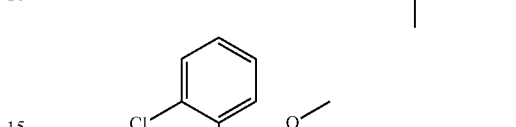

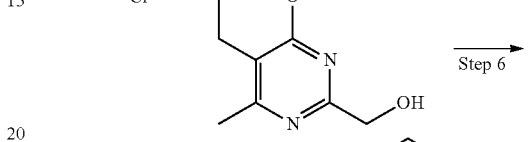

66

-continued

[Step 1]

Methyl 2-(2-chlorobenzyl)-3-oxobutanoate

To a suspension of sodium hydride (60% oil, 0.68 g) in tetrahydrofuran (25 ml), a solution of methyl 3-oxobutanoate (3.0 g) in tetrahydrofuran (5 ml) was added under ice cooling, and the mixture was stirred at room temperature for 30 minutes. A solution of 2-chlorobenzyl bromide (5.3 g) in tetrahydrofuran (5 ml) was added to the reaction solution, and the mixture was stirred at room temperature for 2 days. Ice water and 1 M hydrochloric acid were added to the reaction solution, followed by extraction with ethyl acetate. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (5.6 g).

$^1$H-NMR (CDCl$_3$) δ: 2.22 (3H, s), 3.24 (1H, dd, J=14.1, 8.0 Hz), 3.30 (1H, dd, J=14.1, 6.8 Hz), 3.69 (3H, s), 3.97 (1H, dd, J=8.2, 6.7 Hz), 7.14-7.19 (2H, m), 7.22-7.25 (1H, m), 7.33-7.36 (1H, m).

[Step 2]

2-(tert-Butoxymethyl)-5-(2-chlorobenzyl)-6-methylpyrimidin-4(3H)-one

To a solution of the compound (5.6 g) obtained in step 1 above in N,N-dimethylformamide (30 ml), the compound (5.8 g) obtained in step 1 of Reference Example 2 above and 1,8-diazabicyclo[5.4.0]undec-7-ene (10.5 ml) were added, and the mixture was stirred at 75° C. for 26 hours. After cooling, a saturated aqueous solution of sodium bicarbonate was added to the reaction solution, followed by extraction with ethyl acetate. The extract was washed with water and saturated saline in this order and then dried over anhydrous sodium sulfate. The solvent was distilled off under reduced pressure. Diethyl ether was added to the residue obtained, and the resulting precipitate was collected by filtration to obtain the title compound (2.8 g).

$^1$H-NMR (CDCl$_3$) δ: 1.29 (9H, s), 2.20 (3H, s), 4.01 (2H, s), 4.40 (2H, s), 6.98-7.02 (1H, m), 7.09-7.14 (2H, m), 7.34-7.38 (1H, m).

[Step 3]

2-(tert-Butoxymethyl)-4-chloro-5-(2-chlorobenzyl)-6-methylpyrimidine

To a suspension of the compound (2.8 g) obtained in step 2 above in toluene (10 ml), triphenylphosphine (6.9 g) and trichloroacetonitrile (0.88 ml) were added, and the mixture was stirred at 120° C. for 1 hour. After cooling, a saturated aqueous solution of sodium bicarbonate was added to the reaction solution, followed by extraction with chloroform. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (2.7 g).

$^1$H-NMR (CDCl$_3$) δ: 1.33 (9H, s), 2.44 (3H, s), 4.24 (2H, s), 4.63 (2H, s), 6.65 (1H, dd, J=7.5, 1.8 Hz), 7.12 (1H, td, J=7.5, 1.4 Hz), 7.19 (1H, td, J=7.7, 1.7 Hz), 7.43 (1H, dd, J=7.9, 1.4 Hz).

[Step 4]

2-(tert-Butoxymethyl)-5-(2-chlorobenzyl)-4-methoxy-6-methylpyrimidine

To a solution of the compound (1.5 g) obtained in step 3 above in methanol (4 ml), cesium carbonate (1.44 g) was added, and the mixture was stirred at room temperature for 2 days. Water was added to the reaction solution, followed by extraction with ethyl acetate. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (1.15 g).

$^1$H-NMR (CDCl$_3$) δ: 1.33 (9H, s), 2.34 (3H, s), 3.95 (3H, s), 4.03 (2H, s), 4.55 (2H, s), 6.68-6.71 (1H, m), 7.07 (1H, td, J=7.5, 1.4 Hz), 7.14 (1H, td, J=7.7, 1.8 Hz), 7.38 (1H, dd, J=7.9, 1.4 Hz).

[Step 5]

(5-(2-Chlorobenzyl)-4-methoxy-6-methylpyrimidin-2-yl)methanol

To the compound (1.15 g) obtained in step 4 above, trifluoroacetic acid (2 ml) was added, and the mixture was stirred at room temperature for 24.5 hours. Water was added to the reaction solution, followed by extraction with ethyl acetate. The extract was washed with a saturated aqueous solution of sodium bicarbonate and saturated saline in this order and then dried over anhydrous sodium sulfate. The solvent was distilled off under reduced pressure, and the residue obtained was purified by silica gel column chromatography (n-hexane/ethyl acetate) to obtain the title compound (0.81 g).

$^1$H-NMR (CDCl$_3$) δ: 2.36 (3H, s), 3.76 (1H, t, J=4.9 Hz), 3.95 (3H, s), 4.05 (2H, s), 4.69 (2H, d, J=4.8 Hz), 6.70 (1H, dd, J=7.3, 1.5 Hz), 7.10 (1H, td, J=7.5, 1.4 Hz), 7.15 (1H, td, J=7.5, 1.8 Hz), 7.40 (1H, dd, J=7.8, 1.5 Hz).

[Step 6]

5-(2-Chlorobenzyl)-4-methoxy-6-methylpyrimidine-2-carboxylic acid

To a solution of the compound (0.8 g) obtained in step 5 above in acetonitrile (6 ml), a sodium phosphate buffer solution (0.67 M, pH 6.7, 4 ml) and (2,2,6,6-tetramethylpiperidin-1-yl)oxyl (31 mg) were added, and the mixture was stirred at 35° C. An aqueous sodium chlorite solution (2.0 M, 3.3 ml) and an aqueous sodium hypochlorite solution (0.26%, 2.9 ml) were added dropwise at the same time to the mixture, and the resulting mixture was stirred at 35° C. for 23.5 hours. After cooling, the reaction solution was diluted with a 2 M aqueous sodium hydroxide solution (4 ml). A 10% aqueous sodium thiosulfate solution (6 ml) was added to the solution under ice cooling, and the mixture was stirred at the same temperature as above for 30 minutes. Ethyl acetate was added to the reaction solution to separate two layers. Then, 2 M hydrochloric acid (10 ml) was added to the aqueous layer, followed by extraction with ethyl acetate. The extract was washed with water and saturated saline in this order and then dried over anhydrous sodium sulfate. The solvent was distilled off under reduced pressure. n-Hexane/ethyl acetate was added to the residue obtained, and the resulting precipitate was collected by filtration to obtain the title compound (0.71 g).

$^1$H-NMR (CDCl$_3$) δ: 2.45 (3H, s), 4.08 (3H, s), 4.13 (2H, s), 6.67 (1H, dd, J=7.3, 2.0 Hz), 7.11 (1H, td, J=7.5, 1.3 Hz), 7.18 (1H, td, J=7.7, 1.7 Hz), 7.41 (1H, dd, J=7.9, 1.4 Hz).

MS (m/z): 293 (M+H)$^+$.

The following compounds were obtained by the same method as Example 38.

TABLE 6

| Example | Name and Structure | Instrumental data |
|---|---|---|
| 39 | 5-(2-Chlorobenzyl)-4-ethyl-6-methoxypyrimidine-2-carboxylic acid | $^1$H-NMR (CDCl$_3$) δ: 1.21 (3H, t, J = 7.5 Hz), 2.74 (2H, q, J = 7.5 Hz), 4.09 (3H, s), 4.15 (2H, s), 6.65 (1H, dd, J = 7.6, 1.5 Hz), 7.11 (1H, td, J = 7.6, 1.3 Hz), 7.18 (1H, td, J = 7.7, 1.8 Hz), 7.42 (1H, dd, J = 8.0, 1.3 Hz). MS (m/z): 307 (M + H)$^+$. |
| 40 | 5-(2-Chloro-4-fluorobenzyl)-4-ethyl-6-methoxypyrimidine-2-carboxylic acid | $^1$H-NMR (CDCl$_3$) δ: 1.22 (3H, t, J = 7.5 Hz), 2.75 (2H, q, J = 7.5 Hz), 4.09 (5H, s), 6.63 (1H, dd, J = 8.8, 6.0 Hz), 6.84 (1H, td, J = 8.3, 2.8 Hz), 7.18 (1H, dd, J = 8.4, 2.6 Hz). MS (m/z): 325 (M + H)$^+$. |

TABLE 6-continued

| Example | Name and Structure | Instrumental data |
|---|---|---|
| 41 | 5-(2,3-Dichlorobenzyl)-4-ethyl-6-methoxypyrimidine-2-carboxylic acid | $^1$H-NMR (CDCl$_3$) δ: 1.23 (3H, t, J = 7.5 Hz), 2.73 (2H, q, J = 7.5 Hz), 4.09 (3H, s), 4.17 (2H, s), 6.52 (1H, dd, J = 7.8, 1.3 Hz), 7.05 (1H, t, J = 7.9 Hz), 7.36 (1H, dd, J = 7.9, 1.3 Hz). MS (m/z): 341 (M + H)$^+$. |
| 42 | 5-(4-Chloro-2-fluorobenzyl)-4-ethyl-6-methoxypyrimidine-2-carboxylic acid | $^1$H-NMR (CDCl$_3$) δ: 1.24 (3H, t, J = 7.5 Hz), 2.82 (2H, q, J = 7.5 Hz), 4.02 (2H, s), 4.11 (3H, s), 6.83 (1H, t, J = 8.2 Hz), 7.02 (1H, dd, J = 8.3, 2.5 Hz), 7.09 (1H, dd, J = 9.8, 2.0 Hz). MS (m/z): 325 (M + H)$^+$. |
| 43 | 4-Ethyl-5-(2-fluorobenzyl)-6-methoxypyrimidine-2-carboxylic acid | $^1$H-NMR (CDCl$_3$) δ: 1.23 (3H, t, J = 7.5 Hz), 2.82 (2H, q, J = 7.5 Hz), 4.07 (2H, s), 4.11 (3H, s), 6.87 (1H, td, J = 7.7, 1.8 Hz), 6.98-7.08 (2H, m), 7.17-7.24 (1H, m). MS (m/z): 291 (M + H)$^+$. |
| 44 | 5-(2-Chloro-3-fluorobenzyl)-4-ethyl-6-methoxypyrimidine-2-carboxylic acid | $^1$H-NMR (CDCl$_3$) δ: 1.23 (3H, t, J = 7.5 Hz), 2.74 (2H, q, J = 7.5 Hz), 4.09 (3H, s), 4.16 (2H, s), 6.42-6.45 (1H, m), 7.02-7.12 (2H, m). MS (m/z): 325 (M + H)$^+$. |

Example 45

5-(2-Dichlorobenzyl)-4-methoxy-6-(n-propyl)pyrimidine-2-carboxylic acid hydrochloride

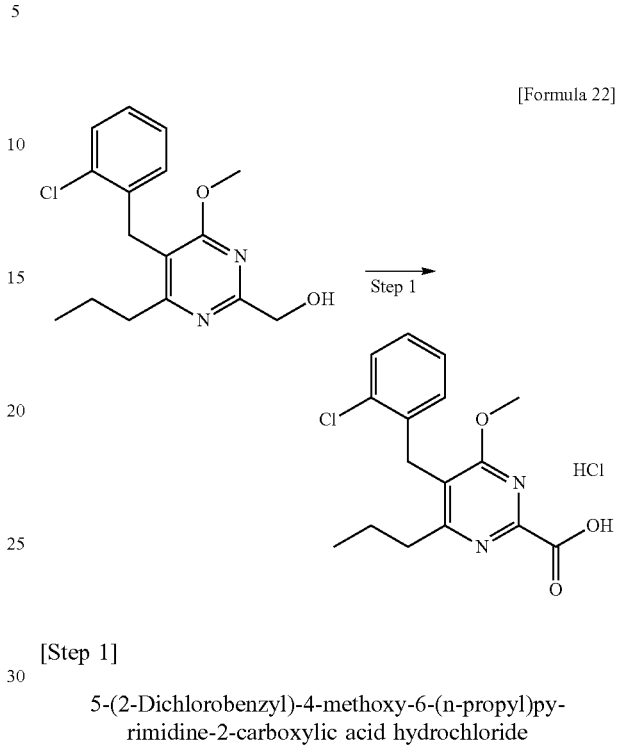

[Formula 22]

[Step 1]

5-(2-Dichlorobenzyl)-4-methoxy-6-(n-propyl)pyrimidine-2-carboxylic acid hydrochloride To a solution of (5-(2-chlorobenzyl)-4-methoxy-6-(n-propyl)pyrimidin-2-yl)methanol (0.32 g) obtained by the same method as steps 1 to 5 of Example 38 in acetonitrile (3 ml), a sodium phosphate buffer solution (0.67 M, pH 6.7, 2 ml) and (2,2,6,6-tetramethylpiperidin-1-yl)oxyl (11 mg) were added, and the mixture was stirred at 35° C. An aqueous sodium chlorite solution (2.0 M, 1.20 ml) and an aqueous sodium hypochlorite solution (0.26%, 1.04 ml) were added dropwise at the same time to the mixture, and the resulting mixture was stirred at 35° C. for 4.5 hours. After cooling, the reaction solution was diluted with a 2 M aqueous sodium hydroxide solution (2 ml). A 10% aqueous sodium thiosulfate solution (3 ml) was added to the solution under ice cooling, and the mixture was stirred at the same temperature as above for 30 minutes. Ethyl acetate was added to the reaction solution to separate two layers. Then, 2 M hydrochloric acid (5 ml) was added to the aqueous layer, followed by extraction with ethyl acetate. The extract was washed with water and saturated saline in this order and then dried over anhydrous sodium sulfate. The solvent was distilled off under reduced pressure. A 4 M solution of hydrochloric acid in ethyl acetate (2 ml) was added to the residue obtained, and the mixture was concentrated under reduced pressure. Ethyl acetate was added to the residue obtained, and the resulting precipitate was collected by filtration to obtain the title compound (295 mg).

$^1$H-NMR (DMSO-d$_6$) δ: 0.82 (3H, t, J=7.3 Hz), 1.50-1.59 (2H, m), 2.59-2.64 (2H, m), 3.93 (3H, s), 4.07 (2H, s), 6.76 (1H, dd, J=7.7, 1.6 Hz), 7.20 (1H, td, J=7.3, 1.8 Hz), 7.26 (1H, td, J=7.5, 1.8 Hz), 7.49 (1H, dd, J=7.8, 1.3 Hz).

MS (m/z): 321 (M+H)$^+$.

The following compounds were obtained by the same method as Example 45.

TABLE 7

| Example | Name and Structure | Instrumental data |
|---|---|---|
| 46 | 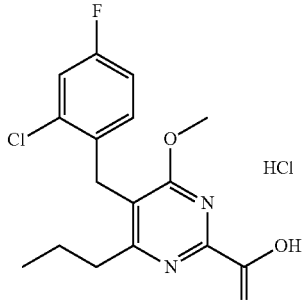<br>5-(2-Chloro-4-fluorobenzyl)-4-methoxy-6-(n-propyl)pyrimidine-2-carboxylic acid hydrochloride | $^1$H-NMR (DMSO-$d_6$) δ: 0.83 (3H, t, J = 7.4 Hz), 1.50-1.61 (2H, m), 2.59-2.65 (2H, m), 3.92 (3H, s), 4.03 (2H, s), 6.83 (1H, dd, J = 8.7, 6.1 Hz), 7.08 (1H, td, J = 8.5, 2.8 Hz), 7.48 (1H, dd, J = 8.8, 2.8 Hz). MS (m/z): 339 (M + H)$^+$. |
| 47 | 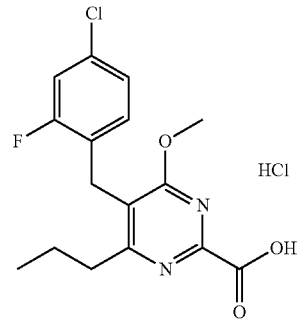<br>5-(4-Chloro-2-fluorobenzyl)-4-methoxy-6-(n-propyl)pyrimidine-2-carboxylic acid hydrochloride | $^1$H-NMR (DMSO-$d_6$) δ: 0.85 (3H, t, J = 7.3 Hz), 1.52-1.62 (2H, m), 2.66-2.72 (2H, m), 3.93 (3H, s), 3.99 (2H, s), 6.98 (1H, t, J = 8.4 Hz), 7.17 (1H, dd, J = 8.2, 2.1 Hz), 7.41 (1H, dd, J = 10.0, 2.3 Hz). MS (m/z): 339 (M + H)$^+$. |

Example 48

5-(2,3-Dichlorobenzyl)-4-ethoxy-6-ethylpyrimidine-2-carboxylic acid

[Formula 23]

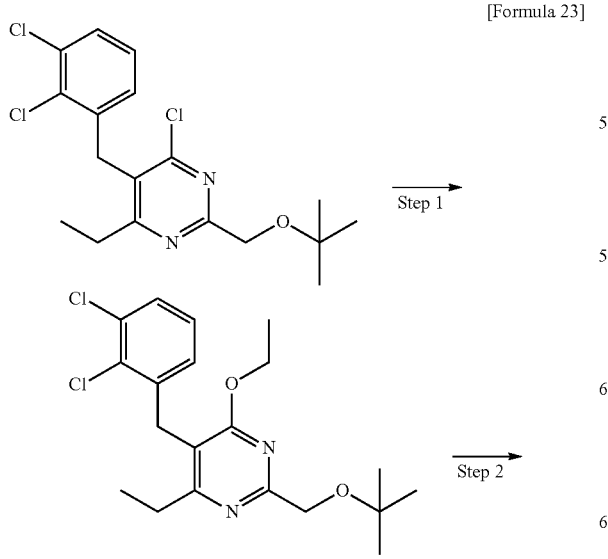

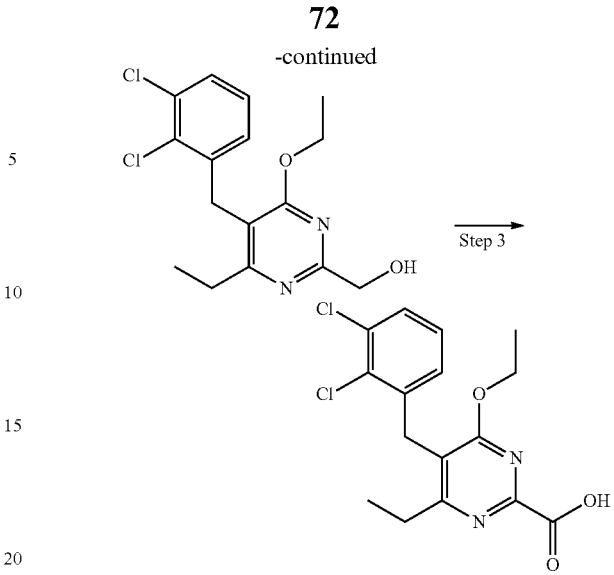

[Step 1]

2-(tert-Butoxymethyl)-5-(2,3-dichlorobenzyl)-4-ethoxy-6-ethylpyrimidine

To a solution of 2-(tert-butoxymethyl)-4-chloro-5-(2,3-dichlorobenzyl)-6-ethylpyrimidine (0.5 g) obtained by the same method as steps 1 to 3 of Example 38 in ethanol (2 ml), cesium carbonate (0.42 g) was added, and the mixture was stirred at room temperature for 2 days. Water was added to the reaction solution, followed by extraction with ethyl acetate. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (0.51 g).

$^1$H-NMR (CDCl$_3$) δ: 1.15 (3H, t, J=7.5 Hz), 1.26 (3H, t, J=7.0 Hz), 1.31 (9H, s), 2.62 (2H, q, J=7.5 Hz), 4.05 (2H, s), 4.41 (2H, q, J=7.1 Hz), 4.54 (2H, s), 6.61 (1H, dd, J=7.8, 1.5 Hz), 7.01 (1H, t, J=8.0 Hz), 7.31 (1H, dd, J=8.0, 1.5 Hz).

[Step 2]

(5-(2,3-Dichlorobenzyl)-4-ethoxy-6-ethylpyrimidin-2-yl)methanol

The title compound (0.43 g) was obtained by the same method as step 5 of Example 38 using the compound (0.51 g) obtained in step 1 above.

$^1$H-NMR (CDCl$_3$) δ: 1.18 (3H, t, J=7.8 Hz), 1.27 (3H, t, J=7.5 Hz), 2.64 (2H, q, J=7.5 Hz), 3.86 (1H, t, J=4.6 Hz), 4.08 (2H, s), 4.39 (2H, q, J=7.3 Hz), 4.68 (2H, d, J=4.5 Hz), 6.61 (1H, dd, J=7.8, 2.0 Hz), 7.03 (1H, t, J=7.9 Hz), 7.33 (1H, dd, J=8.0, 1.8 Hz).

[Step 3]

5-(2,3-Dichlorobenzyl)-4-ethoxy-6-ethylpyrimidine-2-carboxylic acid

The title compound (74 mg) was obtained by the same method as step 6 of Example 38 using the compound (0.43 g) obtained in step 2 above.

¹H-NMR (CDCl₃) δ: 1.23 (3H, t, J=7.5 Hz), 1.32 (3H, t, J=7.0 Hz), 2.75 (2H, q, J=7.5 Hz), 4.17 (2H, s), 4.55 (2H, q, J=7.1 Hz), 6.56-6.59 (1H, m), 7.05 (1H, t, J=7.9 Hz), 7.36 (1H, dd, J=8.0, 1.5 Hz).

MS (m/z): 355 (M+H)⁺.

The following compounds were obtained by the same method as Example 48.

TABLE 8

| Example | Name and Structure | Instrumental data |
|---|---|---|
| 49 | 5-(2-Chloro-4-fluorobenzyl)-4-ethoxy-6-methylpyrimidine-2-carboxylic acid | ¹H-NMR (CDCl₃) δ: 1.34 (3H, t, J = 7.5 Hz), 2.49 (3H, s), 4.08 (2H, s), 4.54 (2H, q, J = 7.1 Hz), 6.73 (1H, dd, J = 8.7, 5.9 Hz), 6.86 (1H, td, J = 8.2, 2.7 Hz), 7.17 (1H, dd, J = 8.4, 2.6 Hz). MS (m/z): 325 (M + H)⁺. |
| 50 | 5-(2,3-Dichlorobenzyl)-4-ethoxy-6-methylpyrimidine-2-carboxylic acid | ¹H-NMR (CDCl₃) δ: 1.33 (3H, t, J = 7.0 Hz), 2.48 (3H, s), 4.16 (2H, s), 4.54 (2H, q, J = 7.1 Hz), 6.62 (1H, dd, J = 7.8, 1.5 Hz), 7.06 (1H, t, J = 7.9 Hz), 7.37 (1H, dd, J = 8.0, 1.5 Hz). MS (m/z): 341 (M + H)⁺. |
| 51 | 5-(4-Chloro-2-fluorobenzyl)-4-ethoxy-6-ethylpyrimidine-2-carboxylic acid | ¹H-NMR (CDCl₃) δ: 1.25 (3H, t, J = 7.5 Hz), 1.36 (3H, t, J = 7.0 Hz), 2.84 (2H, q, J = 7.5 Hz), 4.01 (2H, s), 4.55 (2H, q, J = 7.1 Hz), 6.88 (1H, t, J = 8.3 Hz), 7.02 (1H, dd, J = 8.3, 1.8 Hz), 7.09 (1H, dd, J = 9.8, 2.0 Hz). MS (m/z): 339 (M + H)⁺. |

Example 52

5-(2-Chlorobenzyl)-4-ethoxy-6-methylpyrimidine-2-carboxylic acid hydrochloride

[Formula 24]

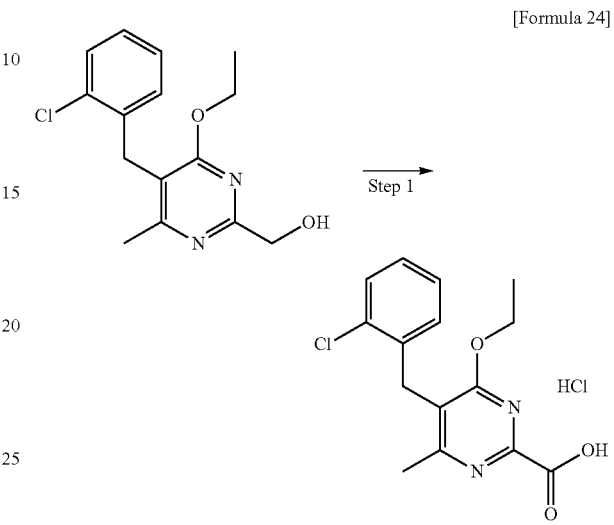

[Step 1]

5-(2-Chlorobenzyl)-4-ethoxy-6-methylpyrimidine-2-carboxylic acid hydrochloride

The title compound (315 mg) was obtained by the same method as step 1 of Example 45 using (5-(2-chlorobenzyl)-4-ethoxy-6-methylpyrimidin-2-yl)methanol (0.27 g) obtained by the same method as steps 1 and 2 of Example 48.

¹H-NMR (DMSO-d₆) δ: 1.20 (3H, t, J=7.3 Hz), 2.39 (3H, s), 4.06 (2H, s), 4.38 (2H, q, J=7.0 Hz), 6.84 (1H, dd, J=7.3, 1.8 Hz), 7.21 (1H, td, J=7.3, 1.5 Hz), 7.26 (1H, td, J=7.5, 1.8 Hz), 7.47 (1H, dd, J=7.7, 1.4 Hz).

MS (m/z): 307 (M+H)⁺.

The following compounds were obtained by the same method as Example 52.

TABLE 9

| Example | Name and Structure | Instrumental data |
|---|---|---|
| 53 | 5-(2-Chlorobenzyl)-4-methyl-6-(n-propoxy)pyrimidine-2-carboxylic acid hydrochloride | ¹H-NMR (DMSO-d₆) δ: 0.77 (3H, t, J = 7.4 Hz), 1.55-1.65 (2H, m), 2.41 (3H, s), 4.07 (2H, s), 4.27 (2H, t, J = 6.4 Hz), 6.83 (1H, dd, J = 7.7, 1.6 Hz), 7.20 (1H, td, J = 7.3, 1.5 Hz), 7.25 (1H, td, J = 7.5, 2.0 Hz), 7.47 (1H, dd, J = 7.8, 1.5 Hz). MS (m/z): 321 (M + H)⁺. |

TABLE 9-continued

| Example | Name and Structure | Instrumental data |
|---|---|---|
| 54 | 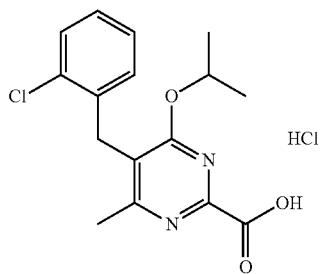<br>5-(2-Chlorobenzyl)-4-ethyl-6-isopropoxypyrimidine-2-carboxylic acid hydrochloride | $^1$H-NMR (DMSO-$d_6$) δ: 1.10 (3H, t, J = 7.3 Hz), 1.16 (6H, d, J = 6.3 Hz), 2.70 (2H, q, J = 8.0 Hz), 4.05 (2H, s), 5.30-5.37 (1H, m), 6.83 (1H, dd, J = 7.4, 1.9 Hz), 7.18-7.27 (2H, m), 7.47 (1H, dd, J = 7.7, 1.6 Hz). MS (m/z): 336 (M + H)$^+$. |
| 55 | 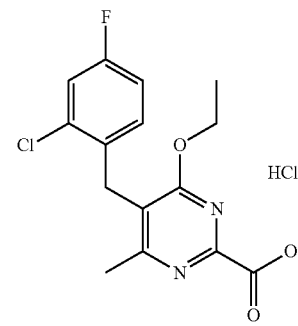<br>5-(2-Chloro-4-fluorobenzyl)-4-ethoxy-6-ethylpyrimidine-2-carboxylic acid hydrochloride | $^1$H-NMR (DMSO-$d_6$) δ: 1.10 (3H, t, J = 7.5 Hz), 1.20 (3H, t, J = 7.0 Hz), 2.70 (2H, q, J = 8.3 Hz), 4.03 (2H, s), 4.38 (2H, q, J = 7.0 Hz), 6.87 (1H, dd, J = 8.8, 6.3 Hz), 7.09 (1H, td, J = 8.5, 2.7 Hz), 7.46 (1H, dd, J = 8.8, 2.8 Hz). MS (m/z): 339 (M + H)$^+$. |
| 56 | 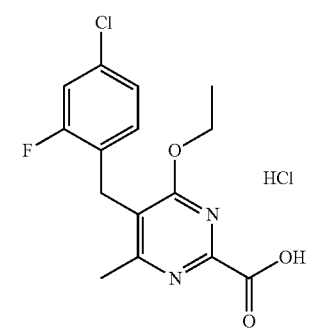<br>5-(4-Chloro-2-fluorobenzyl)-4-ethoxy-6-methylpyrimidine-2-carboxylic acid hydrochloride | $^1$H-NMR (DMSO-$d_6$) δ: 1.24 (3H, t, J = 7.0 Hz), 2.46 (3H, s), 3.96 (2H, s), 4.38 (2H, q, J = 7.0 Hz), 7.08 (1H, t, J = 8.3 Hz), 7.18 (1H, dd, J = 8.3, 2.0 Hz), 7.40 (1H, dd, J = 10.2, 2.1 Hz). MS (m/z): 325 (M + H)$^+$. |
| 57 | 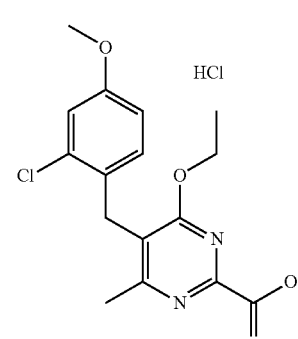<br>5-(2-Chloro-4-methoxybenzyl)-4-ethoxy-6-methylpyrimidine-2-carboxylic acid hydrochloride | $^1$H-NMR (DMSO-$d_6$) δ: 1.23 (3H, t, J = 7.0 Hz), 2.38 (3H, s), 3.74 (3H, s), 3.97 (2H, s), 4.39 (2H, q, J = 7.0 Hz), 6.76 (1H, d, J = 8.5 Hz), 6.80 (1H, dd, J = 8.8, 2.5 Hz), 7.06 (1H, d, J = 2.3 Hz). MS (m/z): 337 (M + H)$^+$. |
| 58 | 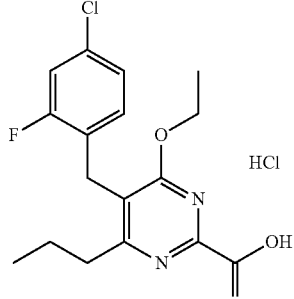<br>5-(4-Chloro-2-fluorobenzyl)-4-ethoxy-6-(n-propyl)pyrimidine-2-carboxylic acid hydrochloride | $^1$H-NMR (DMSO-$d_6$) δ: 0.87 (3H, t, J = 7.4 Hz), 1.23 (3H, t, J = 7.0 Hz), 1.53-1.63 (2H, m), 2.69-2.74 (2H, m), 3.98 (2H, s), 4.38 (2H, q, J = 7.0 Hz), 7.04 (1H, t, J = 8.4 Hz), 7.18 (1H, dd, J = 8.3, 2.0 Hz), 7.40 (1H, dd, J = 10.2, 2.1 Hz). MS (m/z): 353 (M + H)$^+$. |
| 59 | 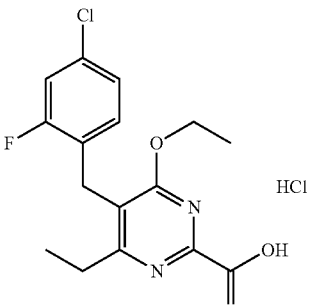<br>4-Ethoxy-6-ethyl-5-(2-fluorobenzyl)pyrimidine-2-carboxylic acid hydrochloride | $^1$H-NMR (DMSO-$d_6$) δ: 1.11 (3H, t, J = 7.5 Hz), 1.23 (3H, t, J = 7.3 Hz), 2.76 (2H, q, J = 7.5 Hz), 4.01 (2H, s), 4.40 (2H, q, J = 7.1 Hz), 7.00 (1H, td, J = 7.8, 1.8 Hz), 7.09 (1H, td, J = 7.4, 1.3 Hz), 7.14-7.20 (1H, m), 7.23-7.30 (1H, m). MS (m/z): 305 (M + H)$^+$. |
| 60 | 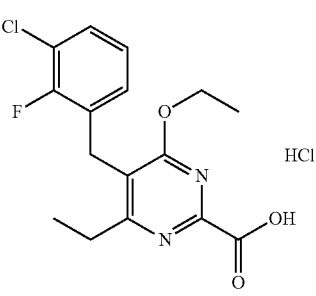<br>5-(3-Chloro-2-fluorobenzyl)-4-ethoxy-6-ethylpyrimidine-2-carboxylic acid hydrochloride | $^1$H-NMR (DMSO-$d_6$) δ: 1.13 (3H, t, J = 7.5 Hz), 1.21 (3H, t, J = 7.0 Hz), 2.78 (2H, q, J = 7.5 Hz), 4.04 (2H, s), 4.37 (2H, q, J = 7.0 Hz), 6.98 (1H, td, J = 7.5, 1.8 Hz), 7.11 (1H, td, J = 7.8, 1.0 Hz), 7.44 (1H, td, J = 7.8, 1.5 Hz). MS (m/z): 339 (M + H)$^+$. |
| 61 | 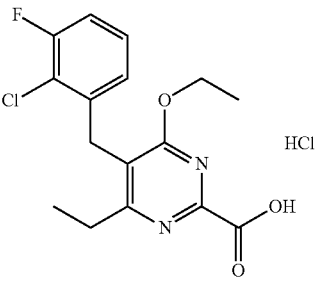<br>5-(2-Chloro-3-fluorobenzyl)-4-ethoxy-6-ethylpyrimidine-2-carboxylic acid hydrochloride | $^1$H-NMR (DMSO-$d_6$) δ: 1.11 (3H, t, J = 7.5 Hz), 1.19 (3H, t, J = 7.0 Hz), 2.70 (2H, q, J = 7.5 Hz), 4.10 (2H, s), 4.37 (2H, q, J = 7.1 Hz), 6.67 (1H, d, J = 7.3 Hz), 7.22-7.31 (2H, m). MS (m/z): 339 (M + H)$^+$. |

TABLE 9-continued

| Example | Name and Structure | Instrumental data |
|---|---|---|
| 62 | 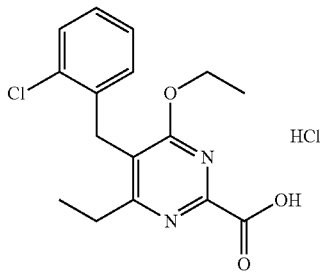<br>5-(2-Chlorobenzyl)-4-ethoxy-6-ethylpyrimidine-2-carboxylic acid hydrochloride | $^1$H-NMR (DMSO-$d_6$) δ: 1.09 (3H, t, J = 7.5 Hz), 1.20 (3H, t, J = 7.3 Hz), 2.68 (2H, q, J = 7.5 Hz), 4.07 (2H, s), 4.39 (2H, q, J = 7.1 Hz), 6.81 (1H, dd, J = 7.5, 1.8 Hz), 7.21 (1H, td, J = 7.3, 1.8 Hz), 7.25 (1H, td, J = 7.5, 2.0 Hz), 7.48 (1H, dd, J = 7.8, 1.5 Hz). MS (m/z): 321 (M + H)$^+$. |
| 63 | 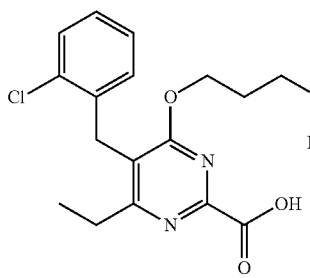<br>5-(2-Chlorobenzyl)-4-ethyl-6-(3-fluoropropoxy)pyrimidine-2-carboxylic acid hydrochloride | $^1$H-NMR (DMSO-$d_6$) δ: 1.11 (3H, t, J = 7.5 Hz), 1.90-2.05 (2H, m), 2.72 (2H, q, J = 7.5 Hz), 4.09 (2H, s), 4.33 (2H, dt, J = 46.9, 6.3 Hz), 4.41 (2H, t, J = 6.8 Hz), 6.81 (1H, dd, J = 7.5, 1.8 Hz), 7.21 (1H, td, J = 7.5, 1.5 Hz), 7.26 (1H, td, J = 7.5, 1.8 Hz), 7.48 (1H, dd, J = 7.8, 1.5 Hz). MS (m/z): 353 (M + H)$^+$. |
| 64 | 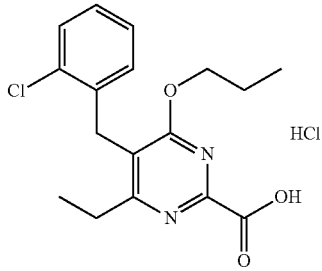<br>5-(2-Chlorobenzyl)-4-ethyl-6-(n-propoxy)pyrimidine-2-carboxylic acid hydrochloride | $^1$H-NMR (DMSO-$d_6$) δ: 0.76 (3H, t, J = 7.4 Hz), 1.11 (3H, t, J = 7.5 Hz), 1.55-1.64 (2H, m), 2.71 (2H, q, J = 7.5 Hz), 4.08 (2H, s), 4.28 (2H, t, J = 6.3 Hz), 6.79 (1H, dd, J = 7.5, 1.8 Hz), 7.20 (1H, td, J = 7.5, 1.5 Hz), 7.25 (1H, td, J = 7.5, 1.8 Hz), 7.48 (1H, dd, J = 7.9, 1.4 Hz). MS (m/z): 335 (M + H)$^+$. |

Example 65

5-(2-Chlorobenzyl)-4-methoxy-6-methylpyrimidine-2-carboxylic acid

[Formula 25]

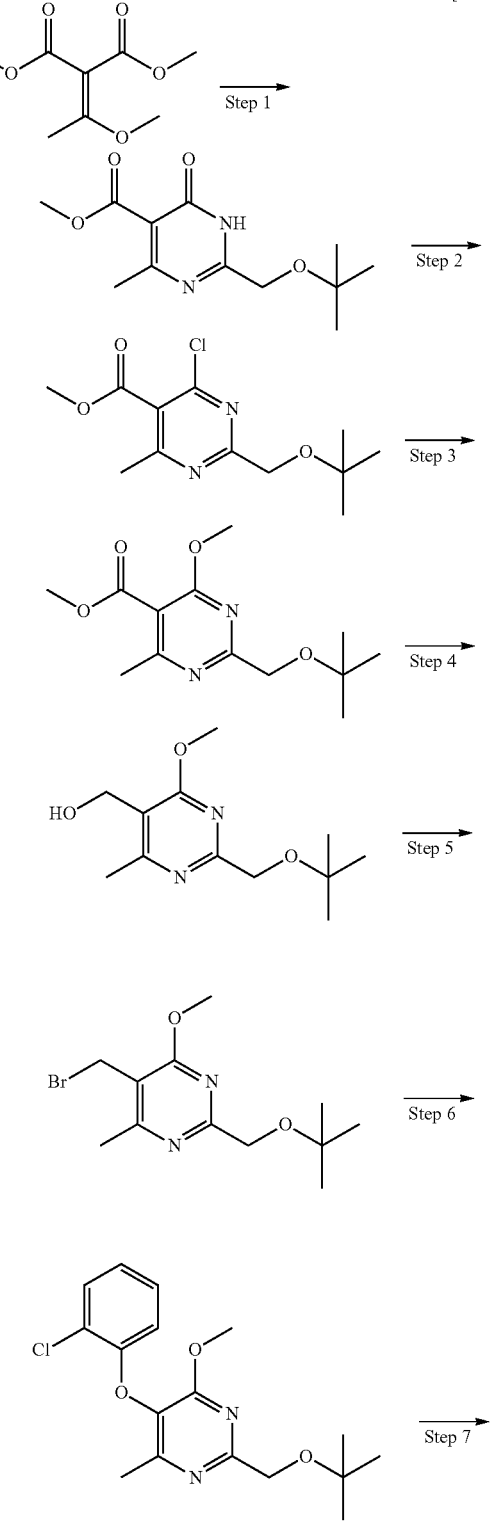

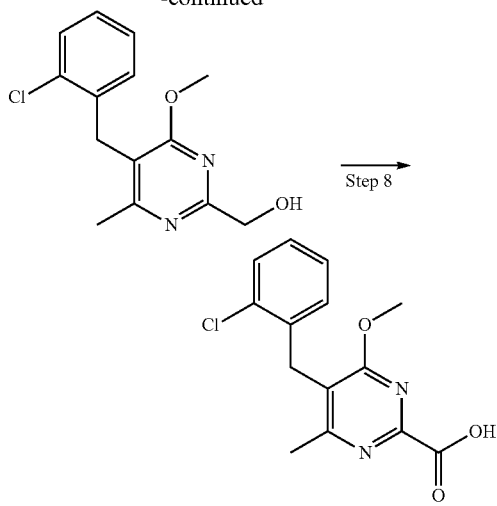

[Step 1]

Methyl 2-(tert-butoxymethyl)-4-methyl-6-oxo-1,6-dihydropyrimidine-5-carboxylate

To a solution of dimethyl 2-(1-methoxyethylidene)malonate (Angew. Chem. Int. Ed., 2013, 52, 8736-8741) (1.57 g) in acetonitrile (40 ml), the compound (1.53 g) obtained in step 1 of Reference Example 2 and triethylamine (5.81 ml) were added, and the mixture was stirred at room temperature for 20 minutes and then stirred at 60° C. for 3.5 hours. After cooling, the reaction solution was concentrated under reduced pressure, and the residue obtained was purified by silica gel column chromatography (n-hexane/ethyl acetate/methanol and n-hexane/ethyl acetate) to obtain the title compound (1.04 g).

$^1$H-NMR (CDCl$_3$) δ: 1.28 (9H, s), 2.38 (3H, s), 3.92 (3H, s), 4.39 (2H, s), 9.80 (1H, br s).
MS (m/z): 255 (M+H)$^+$.

[Step 2]

Methyl 2-(tert-butoxymethyl)-4-chloro-6-methylpyrimidine-5-carboxylate

The title compound (727 mg) was obtained by the same method as step 3 of Example 38 using the compound (1.02 g) obtained in step 1 above.

$^1$H-NMR (CDCl$_3$) δ: 1.30 (9H, s), 2.56 (3H, s), 3.98 (3H, s), 4.63 (2H, s).
MS (m/z): 273 (M+H)$^+$.

[Step 3]

Methyl 2-(tert-butoxymethyl)-4-methoxy-6-methylpyrimidine-5-carboxylate

The title compound (292 mg) was obtained by the same method as step 4 of Example 38 using the compound (406 mg) obtained in step 2 above.

$^1$H-NMR (CDCl$_3$) δ: 1.30 (9H, s), 2.49 (3H, s), 3.91 (3H, s), 4.02 (3H, s), 4.54 (2H, s).
MS (m/z): 269 (M+H)$^+$.

[Step 4]

(2-(tert-Butoxymethyl)-4-methoxy-6-methylpyrimidin-5-yl)methanol

To a solution of the compound (284 mg) obtained in step 3 above in tetrahydrofuran (10 ml), diisobutyl aluminum hydride (1.5 M solution in toluene, 2.12 ml) was added dropwise at −78° C. over 5 minutes, and the mixture was stirred for 2 hours under ice cooling. 1 M hydrochloric acid, water, and a saturated aqueous solution of Rochelle salt were added to the reaction solution, followed by extraction with ethyl acetate. The extract was washed with saturated saline and then dried over anhydrous sodium sulfate. The solvent was distilled off under reduced pressure, and the residue obtained was purified by silica gel column chromatography (ethyl acetate) to obtain the title compound (249 mg).

$^1$H-NMR (CDCl$_3$) δ: 1.30 (9H, s), 2.01 (1H, t, J=6.5 Hz), 2.53 (3H, s), 4.03 (3H, s), 4.52 (2H, s), 4.69 (2H, d, J=6.5 Hz).
MS (m/z): 241 (M+H)$^+$.

[Step 5]

5-(Bromomethyl)-2-(tert-butoxymethyl)-4-methoxy-6-methylpyrimidine

To a solution of the compound (202 mg) obtained in step 4 above in dichloromethane (4 ml), triphenylphosphine (242 mg) was added under ice cooling, and then, a solution of carbon tetrabromide (306 mg) in dichloromethane (1 ml) was added dropwise over 5 minutes. The reaction solution was stirred at room temperature for 20 hours. Then, triphenylphosphine (110 mg) and carbon tetrabromide (139 mg) were further added thereto, and the mixture was further stirred at room temperature for 8 hours. The reaction solution was concentrated under reduced pressure, and the residue obtained was purified by silica gel column chromatography (n-hexane/ethyl acetate) to obtain the title compound (175 mg).

$^1$H-NMR (CDCl$_3$) δ: 1.30 (9H, s), 2.52 (3H, s), 4.05 (3H, s), 4.49 (2H, s), 4.51 (2H, s).
MS (m/z): 303, 305 (M+H)$^+$.

[Step 6]

2-(tert-Butoxymethyl)-5-(2-chlorobenzyl)-4-methoxy-6-methylpyrimidine

To a solution of the compound (50 mg) obtained in step 5 above in dimethyl ethylene glycol (1 ml), 2-chlorophenylboronic acid (28.4 mg), cesium carbonate (107 mg), tetrakis(triphenylphosphine)palladium(0) (9.5 mg), and water (0.5 ml) were added, and the mixture was stirred at 80° C. for 45 minutes under microwave irradiation. The reaction solution was diluted with ethyl acetate, washed with water and saturated saline in this order, and then dried over anhydrous sodium sulfate. The solvent was distilled off under reduced pressure, and the residue obtained was purified by silica gel column chromatography (n-hexane/ethyl acetate) to obtain the title compound (48.3 mg).

$^1$H-NMR (CDCl$_3$) δ: 1.33 (9H, s), 2.34 (3H, s), 3.95 (3H, s), 4.03 (2H, s), 4.55 (2H, s), 6.67-6.72 (1H, m), 7.04-7.10 (1H, m), 7.10-7.16 (1H, m), 7.38 (1H, dd, J=7.8, 1.4 Hz).
MS (m/z): 335 (M+H)$^+$.

[Step 7]

(5-(2-Chlorobenzyl)-4-methoxy-6-methylpyrimidin-2-yl)methanol

To the compound (44.7 mg) obtained in step 6 above, trifluoroacetic acid (1 ml) was added, and the mixture was stirred at room temperature for 1.5 hours. The reaction solution was concentrated under reduced pressure, and ethyl acetate was added to the residue obtained. The mixture was washed with a saturated aqueous solution of sodium bicarbonate, water and saturated saline in this order and then dried over anhydrous sodium sulfate. The solvent was distilled off under reduced pressure, and the residue obtained was purified by silica gel column chromatography (n-hexane/ethyl acetate) to obtain the title compound (24.8 mg).

$^1$H-NMR (CDCl$_3$) δ: 2.36 (3H, s), 3.76 (1H, br. t, J=4.8 Hz), 3.95 (3H, s), 4.05 (2H, s), 4.69 (2H, d, J=4.6 Hz), 6.68-6.72 (1H, m), 7.07-7.12 (1H, m), 7.12-7.18 (1H, m), 7.40 (1H, dd, J=7.8, 1.4 Hz).

MS (m/z): 279 (M+H)$^+$.

[Step 8]

5-(2-Chlorobenzyl)-4-methoxy-6-methylpyrimidine-2-carboxylic acid

To a solution of the compound (21.8 mg) obtained in step 7 above in acetonitrile (0.6 ml), (2,2,6,6-tetramethylpiperidin-1-yl)oxyl (0.9 mg) and a sodium phosphate buffer solution (0.67 M, pH 6.7, 0.45 ml) were added at room temperature. The mixture was warmed to 35° C. Then, an aqueous sodium chlorite solution (2.0 M, 78 μl) and an aqueous sodium hypochlorite solution (0.26%, 90 μl) were added dropwise thereto at the same time, and the mixture was stirred at 35° C. for 17 hours. After cooling, water and a 2 M aqueous sodium hydroxide solution were added to the reaction solution, and then, an aqueous sodium thiosulfate solution (0.4 M) and diethyl ether were added under ice cooling to separate two layers. The aqueous layer was neutralized with 2 M hydrochloric acid, followed by extraction with chloroform. The extract was washed with water and saturated saline in this order and then dried over anhydrous sodium sulfate. The solvent was distilled off under reduced pressure. Diisopropyl ether was added to the residue obtained, and the resulting precipitate was collected by filtration and dried to obtain the title compound (19.3 mg).

The instrumental data was consistent with the instrumental data of the compound obtained in step 6 of Example 38.

The following compounds were obtained by the same method as Example 65.

TABLE 10

| Example | Name and Structure | Instrumental data |
|---|---|---|
| 66 | 5-(2,3-Dichlorobenzyl)-4-methoxy-6-methylpyrimidine-2-carboxylic acid | $^1$H-NMR (CDCl$_3$) δ: 2.47 (3H, s), 4.09 (3H, s), 4.16 (2H, s), 6.55 (1H, dd, J = 7.8, 1.5 Hz), 7.06 (1H, t, J = 7.9 Hz), 7.37 (1H, dd, J = 7.9, 1.5 Hz). MS (m/z): 327 (M + H)$^+$. |
| 67 | 5-(2-Chloro-4-methoxybenzyl)-4-methoxy-6-methylpyrimidine-2-carboxylic acid | $^1$H-NMR (CDCl$_3$) δ: 2.46 (3H, s), 3.77 (3H, s), 4.06 (2H, s), 4.09 (3H, s), 6.56-6.62 (1H, m), 6.64-6.70 (1H, m), 6.97 (1H, d, J = 2.5 Hz). MS (m/z): 323 (M + H)$^+$. |
| 68 | 5-(2-Chloro-4-(trifluoromethyl)benzyl)-4-methoxy-6-methylpyrimidine-2-carboxylic acid | $^1$H-NMR (CDCl$_3$) δ: 2.48 (3H, s), 4.09 (3H, s), 4.17 (2H, s), 6.81 (1H, d, J = 8.2 Hz), 7.35-7.42 (1H, m), 7.67-7.72 (1H, m). MS (m/z): 361 (M + H)$^+$. |
| 69 | 5-(2-Chloro-4-fluorobenzyl)-4-methoxy-6-methylpyrimidine-2-carboxylic acid | $^1$H-NMR (CDCl$_3$) δ: 2.47 (3H, s), 4.09 (3H, s), 4.09 (2H, s), 6.66 (1H, dd, J = 8.7, 6.0 Hz), 6.85 (1H, td, J = 8.3, 2.6 Hz), 7.18 (1H, dd, J = 8.3, 2.7 Hz). MS (m/z): 311 (M + H)$^+$. |

TABLE 10-continued

| Example | Name and Structure | Instrumental data |
|---|---|---|
| 70 | 5-(2-Chlorobenzyl)-4-isopropyl-6-methoxypyrimidine-2-carboxylic acid | $^1$H-NMR (CDCl$_3$) δ: 1.18 (6H, d, J = 6.7 Hz), 3.16 (1H, spt, J = 6.7 Hz), 4.09 (3H, s), 4.16 (2H, s), 6.58-6.65 (1H, m), 7.11 (1H, td, J = 7.5, 1.3 Hz), 7.14-7.21 (1H, m), 7.42 (1H, dd, J = 7.9, 1.3 Hz). MS (m/z): 321 (M + H)$^+$. |
| 71 | 5-(2,4-Dichlorobenzyl)-4-isopropyl-6-methoxypyrimidine-2-carboxylic acid | $^1$H-NMR (CDCl$_3$) δ: 1.20 (6H, d, J = 6.7 Hz), 3.14 (1H, spt, J = 6.7 Hz), 4.09 (3H, s), 4.10 (2H, s), 6.56 (1H, d, J = 8.4 Hz), 7.10 (1H, dd, J = 8.3, 2.1 Hz), 7.44 (1H, d, J = 2.1 Hz). MS (m/z): 355 (M + H)$^+$. |
| 72 | 5-(2-Chloro-4-(trifluoromethyl)benzyl)-4-isopropyl-6-methoxypyrimidine-2-carboxylic acid | $^1$H-NMR (CDCl$_3$) δ: 1.21 (6H, d, J = 6.8 Hz), 3.13 (1H, spt, J = 6.7 Hz), 4.09 (3H, s), 4.19 (2H, s), 6.75 (1H, d, J = 8.3 Hz), 7.34-7.40 (1H, m), 7.70 (1H, d, J = 1.1 Hz). MS (m/z): 389 (M + H)$^+$. |
| 73 | 5-(2-Isopropylbenzyl)-4-methoxy-6-methylpyrimidine-2-carboxylic acid | $^1$H-NMR (CDCl$_3$) δ: 1.31 (6H, d, J = 6.8 Hz), 2.45 (3H, s), 3.30 (1H, spt, J = 6.9 Hz), 4.06 (3H, s), 4.08 (2H, s), 6.45-6.52 (1H, m), 7.01 (1H, td, J = 7.5, 1.3 Hz), 7.18-7.24 (1H, m), 7.33 (1H, dd, J = 7.8, 1.1 Hz). MS (m/z): 301 (M + H)$^+$. |

Example 74

5-(2-Chlorobenzyl)-4-isopropoxy-6-methylpyrimidine-2-carboxylic acid

[Formula 26]

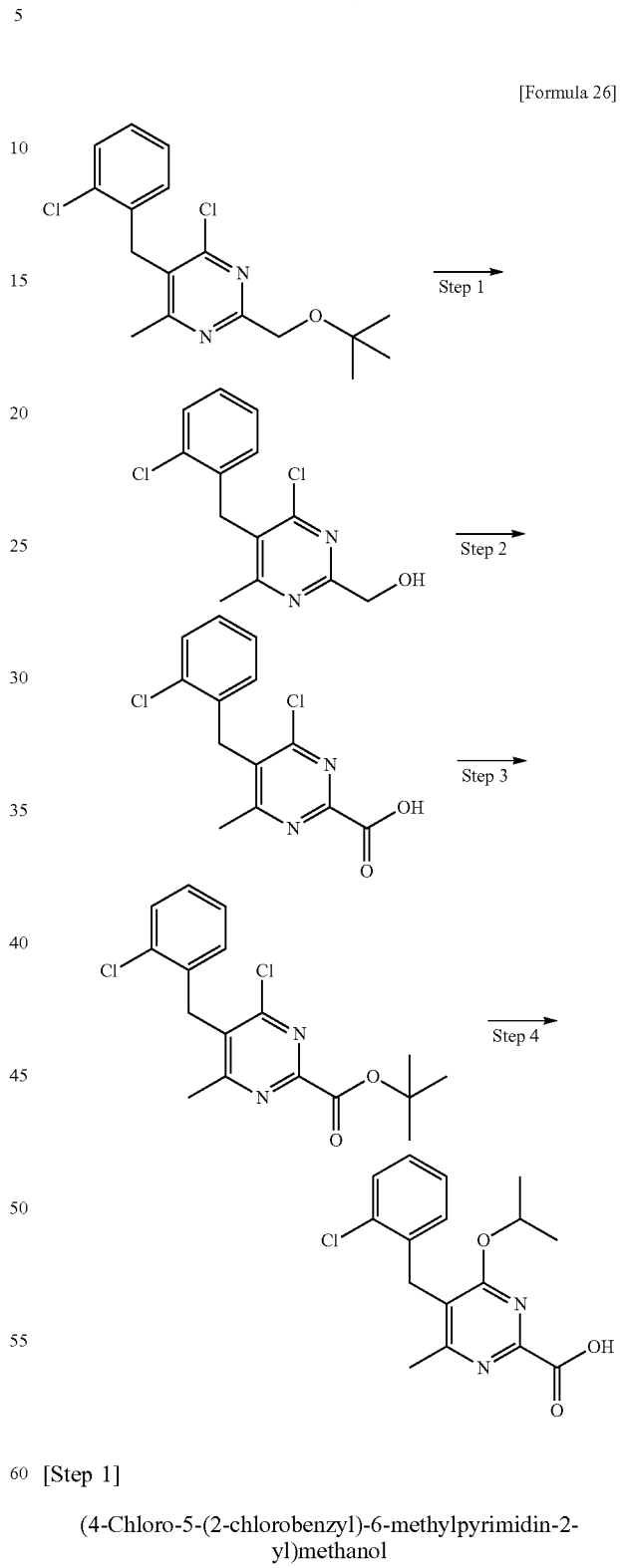

[Step 1]

(4-Chloro-5-(2-chlorobenzyl)-6-methylpyrimidin-2-yl)methanol

The compound (47.49 g) obtained in step 3 of Example 38 was dissolved in trifluoroacetic acid (100 ml), and the mixture was stirred overnight at room temperature. The reaction solution was washed with n-hexane, and toluene (280 ml) was added thereto. A saturated aqueous solution of sodium carbonate (100 ml) was added dropwise to the solution obtained, and the mixture was stirred to separate two layers. The organic layer was washed with a saturated aqueous solution of sodium carbonate and water in this order and then dried over anhydrous sodium sulfate. The solvent was distilled off under reduced pressure. Ethyl acetate (50 ml) was added to the residue obtained, and the mixture was stirred at 60° C. until dissolution. The solution obtained was cooled to room temperature. Then, n-hexane (200 ml) was added dropwise thereto with stirring, and the mixture was stirred overnight at room temperature. The reaction mixture was further stirred for 1.5 hours under ice cooling, and then, the precipitate was collected by filtration, washed with a n-hexane/ethyl acetate mixed solvent (6:1), and then dried under reduced pressure to obtain the title compound (17.81 g). Also, the filtrate was concentrated under reduced pressure, and the residue obtained was purified by silica gel column chromatography (n-hexane/ethyl acetate) and then recrystallized with ethyl acetate/n-hexane to further obtain the title compound (4.31 g).

$^1$H-NMR (CDCl$_3$) δ: 2.46 (3H, s), 3.45 (1H, br s), 4.27 (2H, s), 4.80 (2H, s), 6.62-6.68 (1H, m), 7.09-7.17 (1H, m), 7.17-7.24 (1H, m), 7.44 (1H, dd, J=7.9, 1.4 Hz).

MS (m/z): 283 (M+H)$^+$.

[Step 2]

4-Chloro-5-(2-chlorobenzyl)-6-methylpyrimidine-2-carboxylic acid

The compound (22.05 g) obtained in step 1 above was suspended in acetonitrile (400 ml), and a sodium phosphate buffer solution (0.67 M, pH 6.7, 300 ml) was added to the suspension. (2,2,6,6-Tetramethylpiperidin-1-yl)oxyl (853 mg) was added to the obtained mixed solution, and the mixture was warmed to 35° C. Then, an aqueous sodium chlorite solution (2.0 M, 80 ml) and an aqueous sodium hypochlorite solution (0.26%, 20 ml) were added dropwise thereto over 30 minutes. After stirring at 35° C. for 1 hour, (2,2,6,6-tetramethylpiperidin-1-yl)oxyl (853 mg) was further added thereto, and the mixture was stirred for 1 hour. (2,2,6,6-Tetramethylpiperidin-1-yl)oxyl (853 mg) was further added thereto, and the mixture was stirred for 1 hour. After cooling to room temperature, ice (390 g) was added to the reaction solution, a 2 M aqueous sodium hydroxide solution (176 ml) was gradually added, then sodium thiosulfate (30.0 g) was added, and the mixture was stirred and then concentrated under reduced pressure. Toluene (200 ml) was added to the residue, and the mixture was stirred. After separation of two layers, the aqueous layer was filtered through celite. The aqueous solution obtained was rendered acidic (pH 3) by the dropwise addition of 6 M hydrochloric acid at room temperature, and the mixture was stirred overnight at room temperature. The precipitate was collected by filtration, washed with water, and then dried under reduced pressure to obtain the title compound (21.24 g).

$^1$H-NMR (CDCl$_3$) δ: 4.28 (2H, s), 6.78 (1H, dd, J=7.7, 1.4 Hz), 7.17-7.27 (1H, m), 7.27-7.35 (1H, m), 7.54 (1H, dd, J=7.9, 1.3 Hz), 13.89 (1H, br s).

MS (m/z): 297 (M+H)$^+$.

[Step 3]

tert-Butyl 4-chloro-5-(2-chlorobenzyl)-6-methylpyrimidine-2-carboxylate

To a solution of the compound (18.24 g) obtained in step 2 above in N,N-dimethylacetamide (155 ml), N-methylimidazole (24.5 ml) and tert-butyl alcohol (29.3 ml) were added, and the mixture was warmed to 40° C. p-Toluenesulfonyl chloride (23.4 g) was added in small portions to the reaction solution, and the mixture was stirred at 40° C. for 30 minutes. After cooling, ethyl acetate, n-hexane, and water were added to the reaction solution, and the mixture was stirred to separate two layers. The organic layer was washed with water and a saturated aqueous solution of sodium bicarbonate in this order and then dried over anhydrous magnesium sulfate. The solvent was distilled off under reduced pressure, and the residue obtained was purified by silica gel column chromatography (n-hexane/ethyl acetate) to obtain the title compound (15.95 g).

$^1$H-NMR (CDCl$_3$) δ: 1.67 (9H, s), 2.53 (3H, s), 4.31 (2H, s), 6.56-6.63 (1H, m), 7.07-7.15 (1H, m), 7.17-7.24 (1H, m), 7.44 (1H, dd, J=8.0, 1.3 Hz).

MS (m/z): 353 (M+H)$^+$.

[Step 4]

5-(2-Chlorobenzyl)-4-isopropoxy-6-methylpyrimidine-2-carboxylic acid

A suspension of the compound (70 mg) obtained in step 3 above and cesium carbonate (194 mg) in 2-propanol (2 ml) was heated to reflux for 16 hours. After cooling, the reaction solution was diluted with water, and the pH of the aqueous solution was adjusted to approximately 4 by the addition of 1 M hydrochloric acid. A saturated amount of common salt was added to the mixed solution obtained, followed by extraction with ethyl acetate. The extract was dried over magnesium sulfate. The solvent was distilled off under reduced pressure to obtain the title compound (53.4 mg).

$^1$H-NMR (DMSO-d$_6$) δ: 1.16 (6H, d, J=6.1 Hz), 2.38 (3H, s), 4.00 (2H, s), 5.21-5.49 (1H, br m), 6.48-6.93 (1H, br m), 6.96-7.33 (2H, br m), 7.35-7.52 (1H, m).

MS (m/z): 321 (M+H)$^+$.

Example 75

5-(2,4-Dichlorobenzyl)-4-methyl-6-(methylthio)pyrimidine-2-carboxylic acid

[Formula 27]

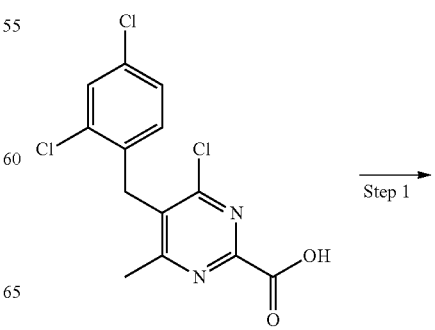

Step 1

87

-continued

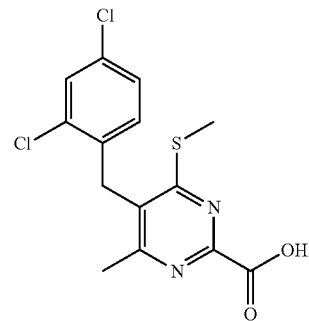

[Step 1]

5-(2,4-Dichlorobenzyl)-4-methyl-6-(methylthio)pyrimidine-2-carboxylic acid

A solution of the compound (25 mg) obtained in step 5 of Example 1 and sodium methanethiolate (50% by weight, 32 mg) in N,N-dimethylformamide (0.4 ml) was stirred at room temperature for 17 hours. The reaction solution was diluted with water and then neutralized with 1 M hydrochloric acid, and the precipitate was collected by filtration and washed with water. The crude product obtained was purified by silica gel column chromatography (chloroform/methanol). The eluted fraction was concentrated under reduced pressure, and the residue obtained was suspended in ethanol. The suspension was diluted with water and cooled under ice cooling, and then, the resulting precipitate was collected by filtration, washed with water, and then dried under reduced pressure to obtain the title compound (8.6 mg).

$^1$H-NMR (CDCl$_3$) δ: 1.16 (6H, d, J=6.1 Hz), 2.38 (3H, s), 4.00 (2H, s), 5.19-5.53 (1H, br m), 6.52-6.96 (1H, br m), 6.99-7.30 (2H, m), 7.34-7.56 (1H, m).

MS (m/z): 343 (M+H)$^+$.

The following compounds were obtained by the same method as Example 75.

TABLE 11

| Example | Name and Structure | Instrumental data |
|---|---|---|
| 76 | 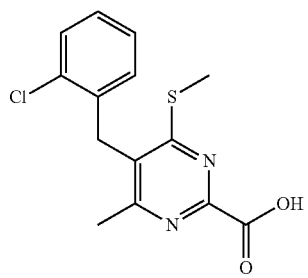<br>5-(2-Chlorobenzyl)-4-methyl-6-(methylthio)pyrimidine-2-carboxylic acid | $^1$H-NMR (CDCl$_3$) δ: 2.46 (3H, s), 2.65 (3H, s), 4.21 (2H, s), 6.57-6.64 (1H, m), 7.11 (1H, td, J = 7.5, 1.3 Hz), 7.17-7.24 (1H, m), 7.45 (1H, dd, J = 8.0, 1.2 Hz). MS (m/z): 309 (M + H)$^+$. |

88

TABLE 11-continued

| Example | Name and Structure | Instrumental data |
|---|---|---|
| 77 | 5-((2,4-Dichlorophenyl)thio)-4-ethyl-6-(methylthio)pyrimidine-2-carboxylic acid | $^1$H-NMR (CD$_3$OD) δ: 1.17 (3H, t, J = 7.0 Hz), 2.54 (3H, s), 3.60 (2H, q, J = 7.0 Hz), 6.57 (1H, d, J = 8.5 Hz), 7.15 (1H, dd, J = 8.5, 2.1 Hz), 7.50 (1H, d, J = 2.1 Hz). MS (m/z): 375 (M + H)$^+$. |
| 78 | 5-(2-Chlorobenzyl)-4-ethyl-6-(methylthio)pyrimidine-2-carboxylic acid | $^1$H-NMR (CDCl$_3$) δ: 1.23 (3H, t, J = 7.5 Hz), 2.65 (3H, s), 2.73 (2H, q, J = 7.5 Hz), 4.22 (2H, s), 6.57-6.63 (1H, m), 7.11 (1H, td, J = 7.5, 1.3 Hz), 7.17-7.24 (1H, m), 7.45 (1H, dd, J = 8.0, 1.2 Hz). MS (m/z): 323 (M + H)$^+$. |

Example 79

5-(2,4-Dichlorobenzyl)-4-(ethylthio)-6-methylpyrimidine-2-carboxylic acid

[Formula 28]

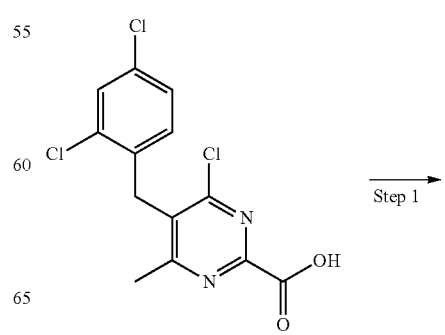

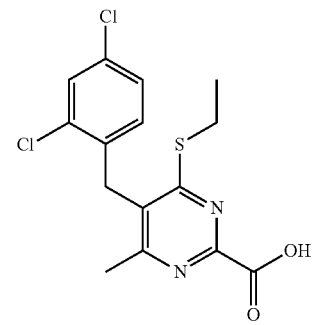

[Step 1]

5-(2,4-Dichlorobenzyl)-4-(ethylthio)-6-methylpyrimidine-2-carboxylic acid

To a solution of the compound (20 mg) obtained in step 5 of Example 1 in N,N-dimethylformamide (0.3 ml), ethanethiol (22 μl) and cesium carbonate (40 mg) were added, and the mixture was stirred at room temperature for 2 hours. The reaction solution was diluted with water and then neutralized with 1 M hydrochloric acid, and the resulting precipitate was collected by filtration, washed with water, and dried under reduced pressure to obtain the title compound (16.4 mg).

$^1$H-NMR (CDCl$_3$) δ: 1.40 (3H, t, J=7.4 Hz), 2.45 (3H, s), 3.30 (2H, q, J=7.4 Hz), 4.13 (2H, s), 6.54 (1H, d, J=8.3 Hz), 7.10 (1H, dd, J=8.3, 2.3 Hz), 7.47 (1H, d, J=2.3 Hz).

MS (m/z): 357 (M+H)$^+$.

The following compounds were obtained by the same method as Example 79.

TABLE 12

| Example | Name and Structure | Instrumental data |
|---|---|---|
| 80 | 5-(2,4-Dichlorophenoxy)-4-(ethylthio)-6-methylpyrimidine-2-carboxylic acid | $^1$H-NMR (CDCl$_3$) δ: 1.39 (3H, t, J = 7.3 Hz), 2.40 (3H, s), 3.27 (2H, q, J = 7.3 Hz), 6.38 (1H, d, J = 8.8 Hz), 7.07-7.16 (1H, m), 7.52 (1H, d, J = 2.4 Hz). MS (m/z): 359 (M + H)$^+$. |
| 81 | 5-(2-Chloro-4-cyanobenzyl)-4-(ethylthio)-6-methylpyrimidine-2-carboxylic acid | $^1$H-NMR (CD$_3$OD) δ: 1.34 (3H, t, J = 7.3 Hz), 2.42 (3H, br s), 3.26-3.34 (2H, m), 4.27 (2H, br s), 6.87 (1H, d, J = 8.0 Hz), 7.54 (1H, d, J = 8.0, 1.4 Hz), 7.90 (1H, d, J = 1.5 Hz). MS (m/z): 348 (M + H)$^+$. |
| 82 | 5-((2,4-Dichlorophenyl)thio)-4-((2-hydroxyethyl)thio)-6-methylpyrimidine-2-carboxylic acid | $^1$H-NMR (CD$_3$OD) δ: 2.55 (3H, br s), 3.39 (2H, t, J = 6.0 Hz), 3.72 (2H, t, J = 6.5 Hz), 4.55 (1H, s), 6.61 (1H, d, J = 8.5 Hz), 7.17 (1H, dd, J = 8.6, 2.2 Hz), 7.51 (1H, d, J = 2.3 Hz). MS (m/z): 391 (M + H)$^+$. |

Example 83

5-((2-Chlorophenyl)thio)-4-(isopropylthio)-6-methylpyrimidine-2-carboxylic acid hydrochloride

[Formula 29]

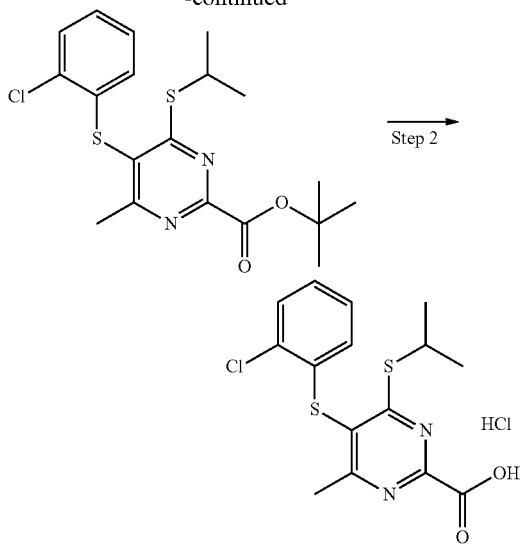

[Step 1]

tert-Butyl 5-((2-chlorophenyl)thio)-4-(isopropyl-
thio)-6-methylpyrimidine-2-carboxylate To a solution of the compound (600 mg) obtained in step 1 of Example 22 in tetrahydrofuran (12.0 ml), sodium 2-propanethiolate (349 mg) was added at 0° C., and the mixture was stirred at the same temperature as above for 2 hours. Water and 1 M hydrochloric acid were added in this order to the reaction solution, followed by extraction with chloroform. The extract was dried over anhydrous sodium sulfate. The solvent was distilled off under reduced pressure, and the residue obtained was purified by silica gel column chromatography (n-hexane/ethyl acetate and n-hexane/acetone) to obtain the title compound (302 mg).

$^1$H-NMR (CDCl$_3$) δ: 1.41 (6H, d, J=6.9 Hz), 1.65 (9H, s), 2.58 (3H, s), 4.02 (1H, spt, J=6.9 Hz), 6.53 (1H, dd, J=7.9, 2.3 Hz), 7.02-7.14 (2H, m), 7.39 (1H, dd, J=8.0, 3.4 Hz).

MS (m/z): 411 (M+H)$^+$.

[Step 2]

5-((2-Chlorophenyl)thio)-4-(isopropylthio)-6-methylpyrimidine-2-carboxylic acid hydrochloride To the compound (195.8 mg) obtained in step 1 above, a 4 M solution of hydrochloric acid in 1,4-dioxane (2.0 ml) was added at room temperature, and the mixture was stirred at room temperature for 21 hours. The reaction solution was concentrated under reduced pressure, and the residue obtained was dissolved in methanol. n-Hexane was added to the solution, and the resulting precipitate was collected by filtration to obtain the title compound (115 mg).

$^1$H-NMR (CD$_3$OD) δ: 1.37 (6H, d, J=6.9 Hz), 2.55 (3H, s), 4.13 (1H, spt, J=6.8 Hz), 6.64 (1H, dd, J=7.5, 2.1 Hz), 7.12-7.23 (2H, m), 7.44 (1H, dd, J=7.3, 1.7 Hz).

MS (m/z): 355 (M+H)$^+$.

The following compound was obtained by the same method as Example 83.

TABLE 13

| Example | Name and Structure | Instrumental data |
|---------|--------------------|--------------------|
| 84 | 5-(2-Chlorobenzyl)-4-(isopropylthio)-6-methylpyrimidine-2-carboxylic acid hydrochloride | $^1$H-NMR (CD$_3$OD) δ: 1.39 (6H, d, J = 6.9 Hz), 2.39 (3H, s), 4.18 (2H, s), 4.21-4.31 (1H, m), 6.61-6.68 (1H, m), 7.11-7.19 (1H, m), 7.19-7.27 (1H, m), 7.46 (1H, dd, J = 7.9, 1.3 Hz). MS (m/z): 337 (M + H)$^+$. |

Example 85

5-((2-Chlorophenyl)amino)-4-methyl-6-(methylthio)pyrimidine-2-carboxylic acid hydrochloride

[Formula 30]

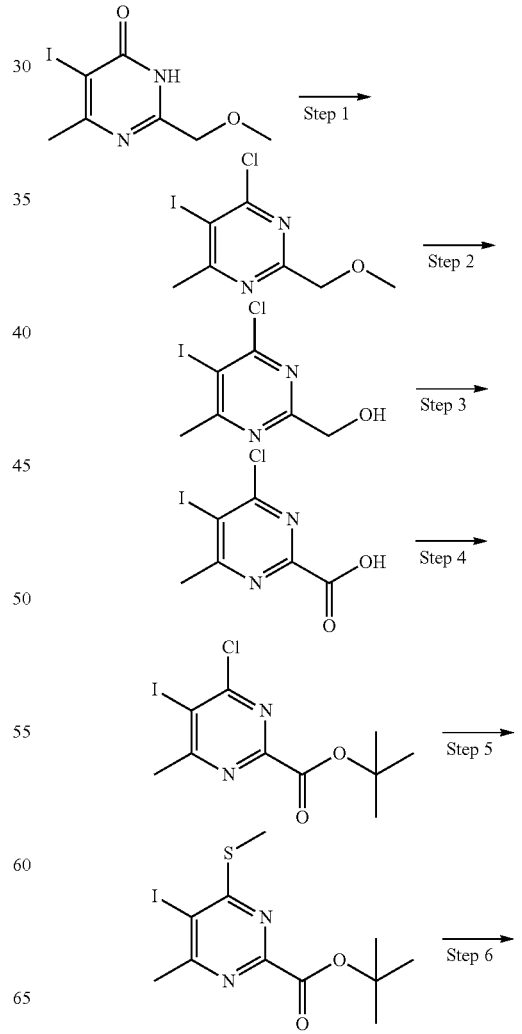

-continued

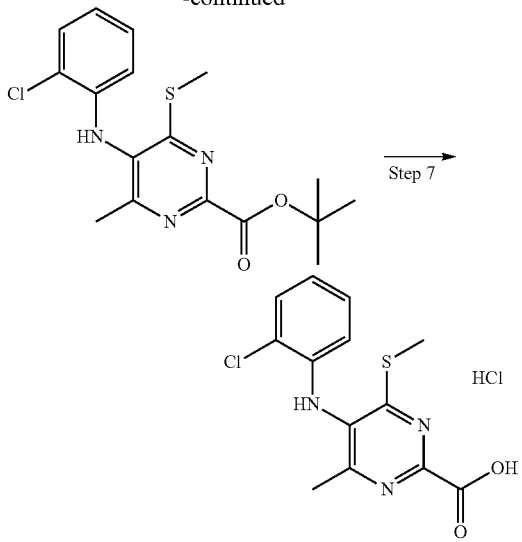

[Step 1]

4-Chloro-5-iodo-2-(methoxymethyl)-6-methylpyrimidine

To a solution of the compound (533 mg) obtained in step 2 of Example 18 in chloroform (11.0 ml), phosphoryl chloride (532 µl) was added at room temperature, and the mixture was stirred at 100° C. for 80 minutes under microwave irradiation. After cooling, the reaction solution was poured into ice water, and the mixture was vigorously stirred. The pH of the reaction solution was adjusted to 10 by the addition of a 2 M aqueous sodium hydroxide solution, followed by separation of two layers. The organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (189 mg).

$^1$H-NMR (CDCl$_3$) δ: 2.81 (3H, s), 3.53 (3H, s), 4.58 (2H, s).

MS (m/z): 299 (M+H)$^+$.

[Step 2]

(4-Chloro-5-iodo-6-methylpyrimidin-2-yl)methanol

The title compound (492 mg) was obtained by the same method as step 4 of Example 17 using the compound (601 mg) obtained in step 1 above.

$^1$H-NMR (CDCl$_3$) δ: 2.83 (3H, s), 3.28 (1H, t, J=5.3 Hz), 4.76 (2H, d, J=5.3 Hz).

MS (m/z): 284 (M+H)$^+$.

[Step 3]

4-Chloro-5-iodo-6-methylpyrimidine-2-carboxylic acid

The title compound (433 mg) was obtained by the same method as step 5 of Example 1 using the compound (492 mg) obtained in step 2 above.

$^1$H-NMR (CDCl$_3$) δ: 2.93 (3H, s).

MS (m/z): 433 (M+H)$^+$.

[Step 4]

tert-Butyl 4-chloro-5-iodo-6-methylpyrimidine-2-carboxylate

The title compound (2.39 g) was obtained by the same method as step 1 of Example 22 using the compound (2.36 g) obtained in step 3 above.

$^1$H-NMR (CDCl$_3$) δ: 1.64 (9H, s), 2.87 (3H, s).

[Step 5]

tert-Butyl 5-iodo-4-methyl-6-(methylthio)pyrimidine-2-carboxylate

To a solution of the compound (93.4 mg) obtained in step 4 above in tetrahydrofuran (2.90 ml), sodium thiomethoxide (40.6 mg) was added at 0° C., and the mixture was stirred at the same temperature as above for 2 hours. Water and 1 M hydrochloric acid were added in this order to the reaction solution, followed by extraction with chloroform. The extract was dried over anhydrous sodium sulfate. The solvent was distilled off under reduced pressure, and the residue obtained was purified by silica gel column chromatography (n-hexane/ethyl acetate) to obtain the title compound (67.5 mg).

$^1$H-NMR (CDCl$_3$) δ: 1.63 (9H, s), 2.60 (3H, s), 2.74 (3H, s).

[Step 6]

tert-Butyl 5-((2-chlorophenyl)amino)-4-methyl-6-(methylthio)pyrimidine-2-carboxylate To a solution of the compound (28.2 mg) obtained in step 5 above in 1,4-dioxane (540 µl), 2-chloroaniline (8.1 µl), tris(dibenzylideneacetone)dipalladium(0) (7.1 mg), 4,5-bis(diphenylphosphino)-9,9-dimethylxanthene (13.4 mg), and cesium carbonate (75.0 mg) were added at room temperature, and the mixture was stirred at 95° C. for 7 hours. Water was added to the reaction solution, followed by extraction with chloroform. The extract was dried over anhydrous sodium sulfate. The solvent was distilled off under reduced pressure, and the residue obtained was purified by silica gel column chromatography (n-hexane/ethyl acetate) to obtain the title compound (22.6 mg).

$^1$H-NMR (CDCl$_3$) δ: 1.59 (9H, s), 2.33 (3H, s), 2.52 (3H, s), 5.59 (1H, s), 6.13 (1H, dd, J=8.4, 1.4 Hz), 6.74 (1H, ddd, J=7.7, 7.7, 1.5 Hz), 6.95-7.01 (1H, m), 7.31 (1H, dd, J=8.0, 1.4 Hz).

MS (m/z): 366 (M+H)$^+$.

[Step 7]

5-((2-Chlorophenyl)amino)-4-methyl-6-(methylthio)pyrimidine-2-carboxylic acid hydrochloride The title compound (11.5 mg) was obtained by the same method as step 3 of Example 22 using the compound (22.6 mg) obtained in step 6 above.

¹H-NMR (CD₃OD) δ: 2.35 (3H, s), 2.57 (3H, s), 6.20 (1H, dd, J=8.2, 1.4 Hz), 6.78 (1H, t, J=7.7 Hz), 6.93 (1H, s), 7.02-7.08 (1H, m), 7.35 (1H, dd, J=8.0, 1.4 Hz).

MS (m/z): 310 (M+H)⁺.

Example 86

5-((2-Chlorophenyl)amino)-4-(ethylamino)-6-methylpyrimidine-2-carboxylic acid hydrochloride

[Formula 31]

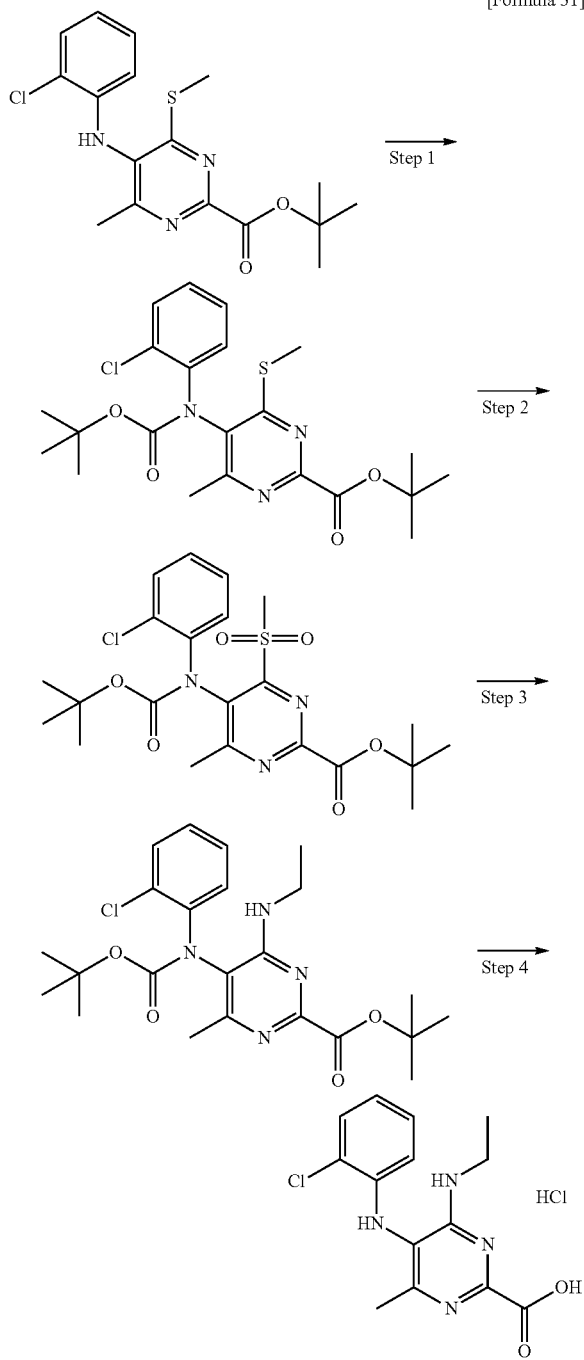

[Step 1]

tert-Butyl 5-((tert-butoxycarbonyl)(2-chlorophenyl)amino)-4-methyl-6-(methylthio)pyrimidine-2-carboxylate To a solution of the compound (171 mg) obtained in step 6 of Example 85 in acetonitrile (2.50 ml), di-tert-butyl dicarbonate (306 mg) was added at room temperature, and the mixture was heated to reflux for 27 hours. After cooling, water was added to the reaction solution, followed by extraction with ethyl acetate. The extract was dried over anhydrous sodium sulfate. The solvent was distilled off under reduced pressure, and the residue obtained was purified by silica gel column chromatography (n-hexane/ethyl acetate) to obtain the title compound (150 mg).

¹H-NMR (CDCl₃) δ: 1.46 (9H, br s), 1.64 (9H, s), 2.45 (3H, s), 2.63 (3H, s), 6.98-7.22 (3H, m), 7.45 (1H, dd, J=7.5, 1.6 Hz).

MS (m/z): 466 (M+H)⁺.

[Step 2]

tert-Butyl 5-((tert-butoxycarbonyl)(2-chlorophenyl)amino)-4-methyl-6-(methylsulfonyl)pyrimidine-2-carboxylate To a solution of the compound (150 mg) obtained in step 1 above in 2-dichloromethane (8.00 ml), m-chloroperbenzoic acid (75%, 296 mg) was added at 0° C., and the mixture was stirred at room temperature for 2 hours. Water was added to the reaction solution, followed by extraction with chloroform. The extract was dried over anhydrous sodium sulfate. The solvent was distilled off under reduced pressure, and the residue obtained was purified by silica gel column chromatography (n-hexane/ethyl acetate) to obtain the title compound (172 mg).

¹H-NMR (CDCl₃) δ: 1.49 (9H, s), 1.64 (9H, s), 2.46 (3H, s), 3.36 (3H, s), 7.12-7.17 (1H, m), 7.19-7.24 (2H, m), 7.44-7.50 (1H, m).

[Step 3]

tert-Butyl 5-((tert-butoxycarbonyl)(2-chlorophenyl)amino)-4-(ethylamino)-6-methylpyrimidine-2-carboxylate To a solution of the compound (160 mg) obtained in step 2 above in 2-propanol (5.0 ml), an aqueous ethylamine solution (33%, 480 μl) was added at room temperature, and the mixture was stirred at 95° C. for 2 hours. After cooling, the reaction solution was concentrated under reduced pressure, and the residue obtained was purified by silica gel column chromatography (n-hexane/ethyl acetate) to obtain the title compound (123 mg).

¹H-NMR (CDCl₃) δ: 1.15 (3H, t, J=7.2 Hz), 1.44 (9H, s), 1.62 (9H, s), 2.52 (3H, s), 3.41-3.56 (2H, m), 6.98-7.04 (1H, m), 7.16-7.24 (2H, m), 7.44-7.49 (1H, m).

[Step 4]

5-((2-Chlorophenyl)amino)-4-(ethylamino)-6-methylpyrimidine-2-carboxylic acid hydrochloride The title compound (7.5 mg) was obtained by the same method as step 3 of Example 22 using the compound (33.4 mg) obtained in step 3 above.

$^1$H-NMR (CD$_3$OD) δ: 1.21 (3H, t, J=7.2 Hz), 2.28 (3H, s), 3.71 (2H, q, J=7.2 Hz), 6.40 (1H, dd, J=8.2, 1.1 Hz), 6.81 (1H, t, J=7.7 Hz), 6.93 (1H, s), 7.07-7.14 (1H, m), 7.38 (1H, dd, J=8.0, 1.4 Hz).

MS (m/z): 307 (M+H)$^+$.

Example 87

5-(2-Chlorobenzyl)-4-methyl-6-(methylamino)pyrimidine-2-carboxylic acid

[Formula 32]

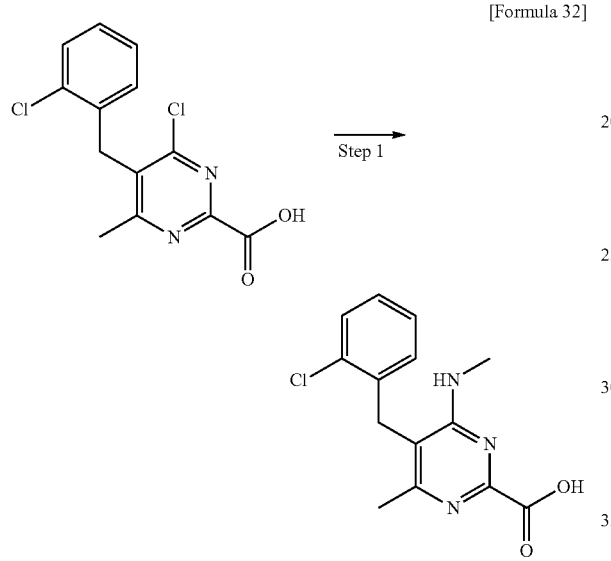

[Step 1]

5-(2-Chlorobenzyl)-4-methyl-6-(methylamino)pyrimidine-2-carboxylic acid

To a solution of the compound (50 mg) obtained in step 2 of Example 74 in 2-propanol (1.7 ml), an aqueous methylamine solution (12 M, 0.07 ml) was added, and the mixture was stirred at 90° C. for 3 hours under microwave irradiation. After cooling, an aqueous methylamine solution (12 M, 0.07 ml) was further added thereto, and the mixture was further stirred at 90° C. for 1 hour under microwave irradiation. The reaction solution was diluted with water under ice cooling and then rendered acidic with 2 M hydrochloric acid, followed by extraction with ethyl acetate. The aqueous layer was saturated with common salt and neutralized with a saturated aqueous solution of sodium bicarbonate, followed by extraction with chloroform. The organic layers were combined and dried over anhydrous sodium sulfate. The solvent was distilled off under reduced pressure to obtain the title compound (25.6 mg).

$^1$H-NMR (CD$_3$OD) δ: 2.34 (3H, s), 3.14 (3H, s), 4.05 (2H, s), 6.83 (1H, d, J=7.5 Hz), 7.11-7.24 (1H, m), 7.24-7.33 (1H, m), 7.48 (1H, dd, J=7.8, 1.4 Hz).

MS (m/z): 292 (M+H)$^+$.

Example 88

4,5-Bis(2-chlorobenzyl)-6-methylpyrimidine-2-carboxylic acid

[Formula 33]

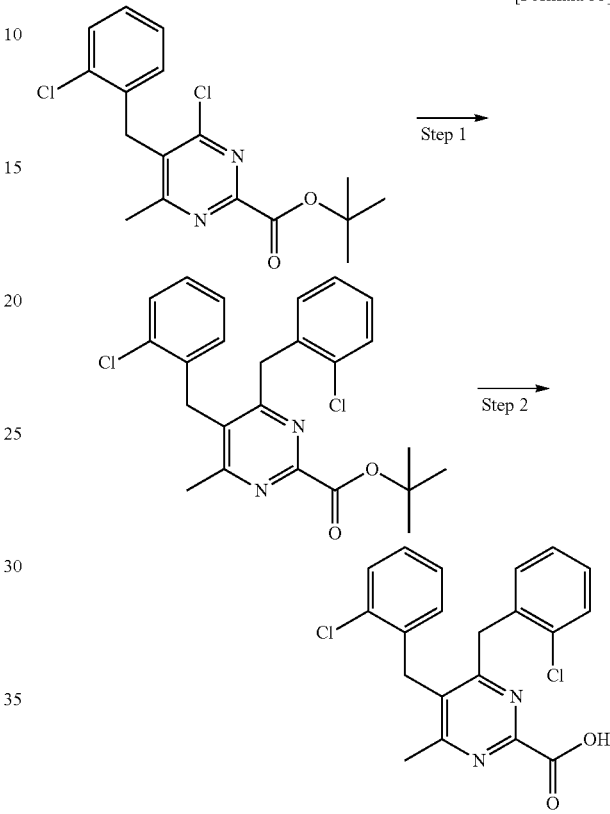

[Step 1]

tert-Butyl 4,5-bis(2-chlorobenzyl)-6-methylpyrimidine-2-carboxylate

To a suspension of the compound (50 mg) obtained in step 3 of Example 74 and tetrakis(triphenylphosphine)palladium (0) (3.4 mg) in tetrahydrofuran (0.5 ml), 2-chlorobenzylzinc chloride (0.5 M solution in tetrahydrofuran, 0.31 ml) was added under an argon atmosphere, and the mixture was stirred at 50° C. for 3 hours. The reaction solution was concentrated under reduced pressure, and the residue obtained was diluted with water, followed by extraction with ethyl acetate. The extract was washed with saturated saline and then dried over anhydrous magnesium sulfate. The solvent was distilled off under reduced pressure, and the residue obtained was purified by silica gel column chromatography (chloroform/ethyl acetate) and amine-coated silica gel column chromatography (n-hexane/ethyl acetate) to obtain the title compound (12.7 mg).

$^1$H-NMR (CDCl$_3$) δ: 1.65 (9H, s), 2.47 (3H, s), 4.11 (2H, s), 4.26 (2H, s), 6.36 (1H, d, J=7.8 Hz), 6.93-7.02 (1H, m), 7.02-7.18 (4H, m), 7.22-7.29 (1H, m), 7.38 (1H, dd, J=8.0, 1.2 Hz).

MS (m/z): 443 (M+H)$^+$.

[Step 2]

4,5-Bis(2-chlorobenzyl)-6-methylpyrimidine-2-carboxylic acid

To a solution of the compound (12.7 mg) obtained in step 1 above in 1,4-dioxane (0.3 ml), a 4 M aqueous lithium hydroxide solution (36 µl) was added, and the mixture was stirred at room temperature for 4 hours. The reaction solution was diluted with water, and 2 M hydrochloric acid (73 µl) was added to the aqueous solution. The precipitate was collected by filtration, washed with water, and then dried in air. The solid obtained was dissolved in chloroform. n-Hexane was added to the solution, and the resulting precipitate was collected by filtration, washed with n-hexane, and then dried under reduced pressure to obtain the title compound (7.6 mg).

$^1$H-NMR (CDCl$_3$) δ: 2.58 (3H, s), 4.22-4.29 (4H, m), 6.44 (1H, d, J=8.0 Hz), 7.03-7.11 (2H, m), 7.12-7.24 (3H, m), 7.30-7.36 (1H, m), 7.44 (1H, dd, J=8.0, 1.2 Hz).

MS (m/z): 387 (M+H)$^+$.

Example 89

5-(2-Chlorobenzyl)-4-((3-cyanobenzyl)oxy)-6-methylpyrimidine-2-carboxylic acid

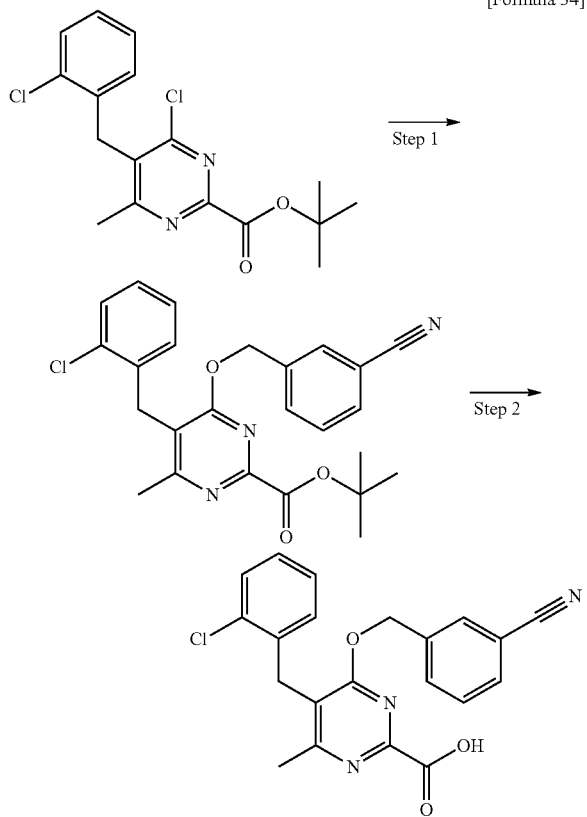

[Formula 34]

[Step 1]

tert-Butyl 5-(2-chlorobenzyl)-4-((3-cyanobenzyl)oxy)-6-methylpyrimidine-2-carboxylate A suspension of the compound (120 mg) obtained in step 3 of Example 74, 18-crown-6 ether (18 mg), potassium carbonate (95 mg) and 3-cyanobenzyl alcohol (80 µl) in dimethyl sulfoxide (1.1 ml) was stirred at 80° C. for 17 hours. After cooling, the reaction solution was diluted with water, followed by extraction with ethyl acetate. The extract was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (92.8 mg).

$^1$H-NMR (CDCl$_3$) δ: 1.67 (9H, s), 2.51 (3H, s), 4.13 (2H, s), 5.46 (2H, s), 6.62 (1H, dd, J=7.7, 1.3 Hz), 7.03-7.10 (1H, m), 7.16-7.23 (1H, m), 7.35-7.41 (1H, m), 7.42 (1H, dd, J=8.0, 1.3 Hz), 7.48-7.59 (3H, m).

MS (m/z): 450 (M+H)$^+$.

[Step 2]

5-(2-Chlorobenzyl)-4-((3-cyanobenzyl)oxy)-6-methylpyrimidine-2-carboxylic acid

To a solution of the compound (92.8 mg) obtained in step 1 above in 1,4-dioxane (2 ml), a 4 M aqueous lithium hydroxide solution (258 µl) was added, and the mixture was stirred at 40° C. for 2 hours. The reaction solution was diluted with water, and 2 M hydrochloric acid (526 µl) was added to the aqueous solution. The mixture was stirred for 30 minutes, and then, the precipitate was collected by filtration, washed with water, and then dried under reduced pressure to obtain the title compound (67 mg).

$^1$H-NMR (CD$_3$OD) δ: 2.53 (3H, s), 4.19 (2H, s), 5.53 (2H, s), 6.79 (1H, dd, J=7.7, 1.4 Hz), 7.10-7.16 (1H, m), 7.18-7.26 (1H, m), 7.39-7.49 (2H, m), 7.50-7.54 (1H, m), 7.55-7.65 (2H, m).

MS (m/z): 394 (M+H)$^+$.

The following compounds were obtained by the same method as Example 89.

TABLE 14

| Example | Name and Structure | Instrumental data |
|---|---|---|
| 90 | 4-(Benzyloxy)-5-(2-chlorobenzyl)-6-methylpyrimidine-2-carboxylic acid | $^1$H-NMR (CD$_3$OD) δ: 2.47 (3H, s), 4.17 (2H, s), 5.51 (2H, s), 6.76 (1H, dd, J = 7.7, 1.4 Hz), 7.06-7.13 (1H, m), 7.15-7.23 (1H, m), 7.24-7.32 (5H, m), 7.40 (1H, dd, J = 8.0, 1.3 Hz). MS (m/z): 369 (M + H)$^+$. |

TABLE 14-continued

| Example | Name and Structure | Instrumental data |
|---|---|---|
| 91 | 5-(2-Chlorobenzyl)-4-(trans-3-cyanocyclobutoxy)-6-methylpyrimidine-2-carboxylic acid | ¹H-NMR (CD₃OD) δ: 2.23-2.36 (2H, m), 2.49 (3H, s), 2.86-3.03 (3H, m), 4.18 (2H, s), 5.35 (1H, s), 6.90 (1H, dd, J = 7.4, 1.8 Hz), 7.15-7.28 (2H, m), 7.44 (1H, dd, J = 7.7, 1.6 Hz). MS (m/z): 358 (M + H)⁺. |
| 92 | 5-(2-Chlorobenzyl)-4-(cis-3-cyanocyclobutoxy)-6-methylpyrimidine-2-carboxylic acid | ¹H-NMR (CD₃OD) δ: 2.40-2.49 (2H, m), 2.53 (3H, s), 2.82-2.96 (2H, m), 3.01-3.11 (1H, m), 4.14 (2H, s), 5.60-5.69 (1H, m), 6.73 (1H, dd, J = 7.6, 1.4 Hz), 7.10-7.17 (1H, m), 7.17-7.24 (1H, m), 7.43 (1H, dd, J = 7.9, 1.4 Hz). MS (m/z): 358 (M + H)⁺. |
| 93 | 5-(2-Chlorobenzyl)-4-methyl-6-(pyridin-3-ylmethoxy)pyrimidine-2-carboxylic acid | ¹H-NMR (CDCl₃) δ: 2.50 (3H, s), 4.18 (2H, s), 5.56 (2H, s), 6.77 (1H, dd, J = 7.6, 1.3 Hz), 7.06-7.14 (1H, m), 7.16-7.24 (1H, m), 7.35-7.43 (2H, m), 7.75-7.82 (1H, m), 8.53 (1H, s). MS (m/z): 370 (M + H)⁺ |
| 94 | 5-(2-Chlorobenzyl)-4-methyl-6-(pyridin-4-ylmethoxy)pyrimidine-2-carboxylic acid | ¹H-NMR (CD₃OD) δ: 2.52 (3H, s), 4.24 (2H, s), 5.60 (2H, s), 6.84 (1H, dd, J = 7.7, 1.4 Hz), 7.12-7.19 (1H, m), 7.20-7.26 (1H, m), 7.27-7.32 (2H, m), 7.44 (1H, dd, J = 7.9, 1.3 Hz), 8.41-8.46 (2H, m). MS (m/z): 370 (M + H)⁺. |
| 95 | 5-(2-Chlorobenzyl)-4-methyl-6-(pyridin-2-ylmethoxy)pyrimidine-2-carboxylic acid | ¹H-NMR (CD₃OD) δ: 2.49 (3H, s), 4.22 (2H, s), 5.61 (2H, s), 6.82 (1H, dd, J = 7.7, 1.4 Hz), 7.08-7.15 (1H, m), 7.17-7.23 (1H, m), 7.29-7.37 (2H, m), 7.40 (1H, dd, J = 7.9, 1.3 Hz), 7.72-7.80 (1H, m), 8.45-8.52 (1H, m). MS (m/z): 370 (M + H)⁺. |
| 96 | 5-(2-Chlorobenzyl)-4-methyl-6-((6-methylpyridin-3-yl)methoxy)pyrimidine-2-carboxylic acid | ¹H-NMR (CD₃OD) δ: 2.48 (3H, s), 2.53 (3H, s), 4.16 (2H, s), 5.53 (2H, s), 6.75 (1H, dd, J = 7.7, 1.3 Hz), 7.06-7.14 (1H, m), 7.16-7.23 (1H, m), 7.29 (1H, d, J = 8.0 Hz), 7.39 (1H, dd, J = 8.0, 1.3 Hz), 7.72 (1H, dd, J = 8.0, 2.3 Hz), 8.45 (1H, d, J = 2.3 Hz). MS (m/z): 384 (M + H)⁺. |
| 97 | 5-(2-Chlorobenzyl)-4-((4-fluorobenzyl)oxy)-6-methylpyrimidine-2-carboxylic acid | ¹H-NMR (CD₃OD) δ: 2.47 (3H, s), 4.15 (2H, s), 5.48 (2H, s), 6.75 (1H, dd, J = 7.6, 1.4 Hz), 6.95-7.03 (2H, m), 7.07-7.14 (1H, m), 7.16-7.23 (1H, m), 7.27-7.35 (2H, m), 7.39 (1H, dd, J = 8.0, 1.3 Hz). MS (m/z): 387 (M + H)⁺. |
| 98 | 5-(2-Chlorobenzyl)-4-((3-fluorobenzyl)oxy)-6-methylpyrimidine-2-carboxylic acid | ¹H-NMR (CD₃OD) δ: 2.50 (3H, s), 4.18 (2H, s), 5.50 (2H, s), 6.78 (1H, dd, J = 7.8, 1.4 Hz), 6.93-7.03 (2H, m), 7.06-7.15 (2H, m), 7.17-7.23 (1H, m), 7.24-7.33 (1H, m), 7.41 (1H, dd, J = 8.0, 1.3 Hz). MS (m/z): 387 (M + H)⁺. |

TABLE 14-continued

| Example | Name and Structure | Instrumental data |
|---|---|---|
| 99 | 5-(2-Chlorobenzyl)-4-((2-fluorobenzyl)oxy)-6-methylpyrimidine-2-carboxylic acid | $^1$H-NMR (CD$_3$OD) δ: 2.47 (3H, s), 4.14 (2H, s), 5.57 (2H, s), 6.77 (1H, dd, J = 7.8, 1.4 Hz), 7.02-7.12 (3H, m), 7.13-7.20 (1H, m), 7.28-7.40 (3H, m), MS (m/z): 387 (M + H)$^+$. |
| 100 | 5-(2-Chlorobenzyl)-4-((2,4-difluorobenzyl)oxy)-6-methylpyrimidine-2-carboxylic acid | $^1$H-NMR (CD$_3$OD) δ: 2.48 (3H, s), 4.13 (2H, s), 5.53 (2H, s), 6.76 (1H, dd, J = 7.7, 1.4 Hz), 6.83-6.96 (2H, m), 7.04-7.11 (1H, m), 7.13-7.21 (1H, m), 7.36 (1H, dd, J = 8.0, 1.3 Hz), 7.38-7.46 (1H, m). MS (m/z): 405 (M + H)$^+$. |

Example 101

5-(2-Chlorobenzyl)-4-methyl-6-(2-(pyridin-4-yl)ethyl)pyrimidine-2-carboxylic acid

[Formula 35]

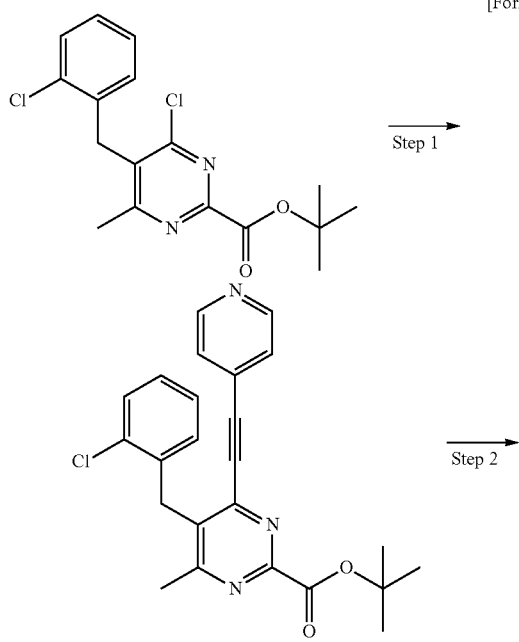

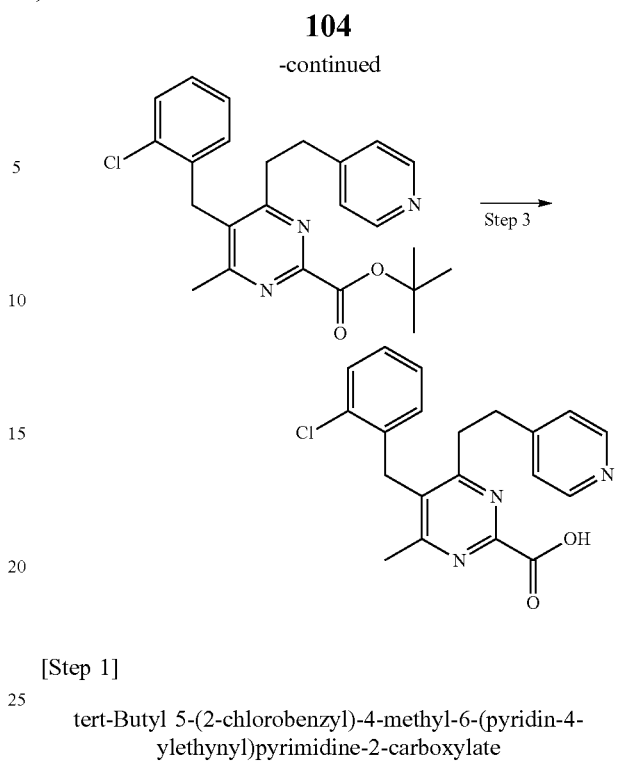

[Step 1]

tert-Butyl 5-(2-chlorobenzyl)-4-methyl-6-(pyridin-4-ylethynyl)pyrimidine-2-carboxylate A suspension of the compound (150 mg) obtained in step 3 of Example 74, bis(triphenylphosphine)palladium(II) chloride (30 mg), copper(I) iodide (5 mg), 4-ethynylpyridine (88 mg), and triethylamine (0.6 ml) in toluene (2 ml) was stirred at 100° C. for 2 hours under an argon atmosphere. After cooling, the reaction solution was filtered, and the filtrate was concentrated under reduced pressure. The residue obtained was purified by silica gel column chromatography (n-hexane/ethyl acetate) to obtain the title compound (93.2 mg).

$^1$H-NMR (CDCl$_3$) δ: 1.69 (9H, s), 2.55 (3H, s), 4.42 (2H, s), 6.66 (1H, dd, J=7.8, 1.4 Hz), 7.08-7.15 (1H, m), 7.17-7.23 (1H, m), 7.28-7.33 (2H, m), 7.45 (1H, dd, J=7.9, 1.3 Hz), 8.60-8.64 (2H, m).
MS (m/z): 420 (M+H)$^+$.

[Step 2]

tert-Butyl 5-(2-chlorobenzyl)-4-methyl-6-(2-(pyridin-4-yl)ethyl)pyrimidine-2-carboxylate To a solution of the compound (93.2 mg) obtained in step 1 above in ethanol (2.2 ml), 5% palladium carbon (56% aqueous, 42.4 mg) was added, and the mixture was stirred at room temperature for 1.5 hours under a hydrogen atmosphere. The reaction solution was filtered, and the filtrate was concentrated under reduced pressure to obtain the title compound (87.7 mg).

$^1$H-NMR (CDCl$_3$) δ: 1.66-1.72 (9H, m), 2.50 (3H, s), 3.00-3.13 (4H, m), 4.09 (2H, s), 6.34 (1H, dd, J=7.5, 1.0 Hz), 7.00-7.07 (1H, m), 7.11 (2H, d, J=5.8 Hz), 7.16-7.23 (1H, m), 7.44 (1H, dd, J=8.0, 1.2 Hz), 8.43 (2H, d, J=5.8 Hz).
MS (m/z): 424 (M+H)$^+$.

[Step 3]

5-(2-Chlorobenzyl)-4-methyl-6-(2-(pyridin-4-yl)ethyl)pyrimidine-2-carboxylic acid To a solution of the compound (87.7 mg) obtained in step 2 above in 1,4-dioxane (2 ml), a 4 M aqueous lithium hydroxide solution (259 μl) was added, and the mixture was stirred at 40° C. for 2.5 hours. The reaction solution was diluted with water, and 2 M hydrochloric acid (528 μl) was added to the aqueous solution. Then, the mixture was saturated with common salt, followed by extraction with chloroform three times. The extract was dried over anhydrous sodium sulfate. The solvent was distilled off under reduced pressure, and the residue obtained was dissolved in ethanol (2 ml). Diethyl ether (4 ml) and n-hexane (20 ml) were added to the solution, and the mixture was stirred for 1 hour. The precipitate was collected by filtration, washed with n-hexane, and then dried under reduced pressure to obtain the title compound (64 mg).

$^1$H-NMR (DMSO-$d_6$) δ: 2.40 (3H, s), 2.97-3.07 (4H, m), 4.16 (2H, s), 6.57 (1H, dd, J=7.8, 1.4 Hz), 7.12-7.19 (1H, m), 7.25-7.30 (3H, m), 7.52 (1H, dd, J=8.0, 1.2 Hz), 8.45 (2H, d, J=5.9 Hz).

MS (m/z): 368 (M+H)$^+$.

The following compound was obtained by the same method as Example 101.

TABLE 15

| Example | Name and Structure | Instrumental data |
|---|---|---|
| 102 | 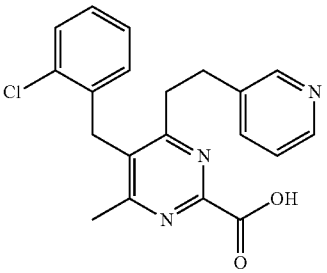<br>5-(2-Chlorobenzyl)-4-methyl-6-(2-(pyridin-3-yl)ethyl)pyrimidine-2-carboxylic acid | $^1$H-NMR (CD$_3$OD) δ: 2.49 (3H, s), 3.01-3.12 (4H, m), 4.20 (2H, s), 6.52 (1H, d, J = 7.8 Hz), 7.07-7.17 (1H, m), 7.19-7.30 (1H, m), 7.36 (1H, dd, J = 7.6, 5.1 Hz), 7.48 (1H, dd, J = 8.0, 1.1 Hz), 7.67-7.75 (1H, m), 8.30-8.40 (2H, m).<br>MS (m/z): 368 (M + H)$^+$. |

Example 103

5-(2-Chlorobenzyl)-4,6-dimethylpyrimidine-2-carboxylic acid

[Formula 36]

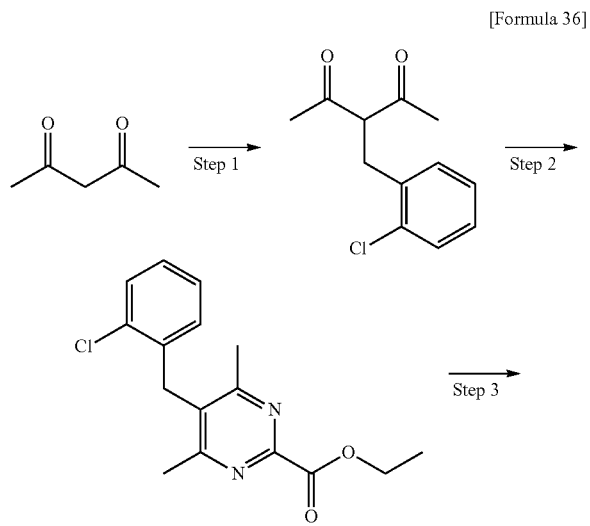

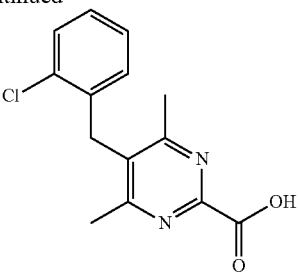

[Step 1]

3-(2-Chlorobenzyl)pentane-2,4-dione

To a solution of pentane-2,4-dione (4.62 g) in ethanol (20 ml), sodium ethoxide (5.23 g) was added, and the mixture was stirred at room temperature for 1 hour. 2-Chlorobenzyl bromide (3.16 g) was added to the reaction solution, and the mixture was stirred at 80° C. for 2 hours. Water and dichloromethane were added to the reaction solution to separate two layers. The organic layer was dried over anhydrous sodium sulfate. The solvent was distilled off under reduced pressure, and the residue obtained was purified by silica gel column chromatography (n-hexane/ethyl acetate) to obtain the title compound (2.77 g).

$^1$H-NMR (CDCl$_3$) δ: 2.03 (3H, s), 2.16 (3H, s), 3.25 (2H, d, J=7.3 Hz), 4.14 (1H, t, J=7.3 Hz), 7.04-7.24 (3H, m), 7.33-7.41 (1H, m).

[Step 2]

Ethyl 5-(2-chlorobenzyl)-4,6-dimethylpyrimidine-2-carboxylate

To a solution of the compound (500 mg) obtained in step 1 above in methanol (2.5 ml), ammonium acetate (172 mg) was added, and the mixture was stirred at room temperature for 4 hours. The reaction solution was concentrated under reduced pressure. Then, ethyl cyanoformate (218 μl) and a 4 M solution of hydrochloric acid in 1,4-dioxane (2.5 ml) were added to the residue obtained, and the mixture was stirred at room temperature for 21 hours. The reaction solution was concentrated under reduced pressure, and water, a saturated aqueous solution of sodium bicarbonate and dichloromethane were added to the residue obtained to separate two layers. The organic layer was dried over anhydrous sodium sulfate. The solvent was distilled off under reduced pressure, and the residue obtained was purified by silica gel column chromatography (n-hexane/ethyl acetate) to obtain the title compound (109 mg).

$^1$H-NMR (CDCl$_3$) δ: 1.47 (3H, t, J=7.2 Hz), 2.52 (6H, s), 4.18 (2H, s), 4.55 (2H, q, J=7.2 Hz), 6.48-6.53 (1H, m), 7.05-7.24 (2H, m), 7.43-7.48 (1H, m).

[Step 3]

5-(2-Chlorobenzyl)-4,6-dimethylpyrimidine-2-carboxylic acid

To a solution of the compound (109 mg) obtained in step 2 above in methanol (2 ml), a 1 M aqueous sodium hydroxide solution (0.537 ml) was added, and the mixture was stirred at room temperature for 1 hour. 1 M hydrochloric acid (5 ml) and chloroform were added to the reaction solution to separate two layers. The organic layer was dried over anhydrous sodium sulfate. The solvent was distilled off under reduced pressure, and the residue obtained was purified by silica gel column chromatography (chloroform/methanol) to obtain the title compound (44.5 mg).

$^{1}$H-NMR (CDCl$_{3}$) δ: 2.55 (6H, s), 4.21 (2H, s), 6.50 (1H, d, J=8.0 Hz), 7.13 (1H, dd, J=8.0, 8.0 Hz), 7.23 (1H, dd, J=8.0, 8.0 Hz), 7.47 (1H, d, J=8.0 Hz).

MS (m/z): 277 (M+H)$^{+}$.

The following compound was obtained by the same method as Example 103.

TABLE 16

| Example | Name and Structure | Instrumental data |
|---|---|---|
| 104 | Cl-C6H3-CH2-[pyrimidine with two methyl groups and COOH]<br>5-(2,4-Dichlorobenzyl)-4,6-dimethylpyrimidine-2-carboxylic acid | $^{1}$H-NMR (CDCl$_{3}$) δ: 2.55 (6H, s), 4.16 (2H, s), 6.43 (1H, d, J = 8.3 Hz), 7.12 (1H, dd, J = 8.3, 2.3 Hz), 7.50 (1H, d, J = 2.3 Hz). MS (m/z): 311 (M + H)$^{+}$. |

Example 105

5-(2,4-Dichlorobenzyl)-N,6-dimethyl-2-(1H-tetrazol-5-yl)pyrimidin-4-amine

[Formula 37]

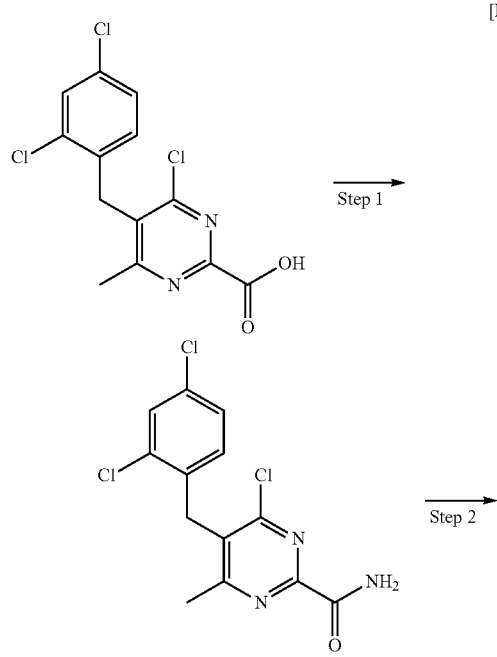

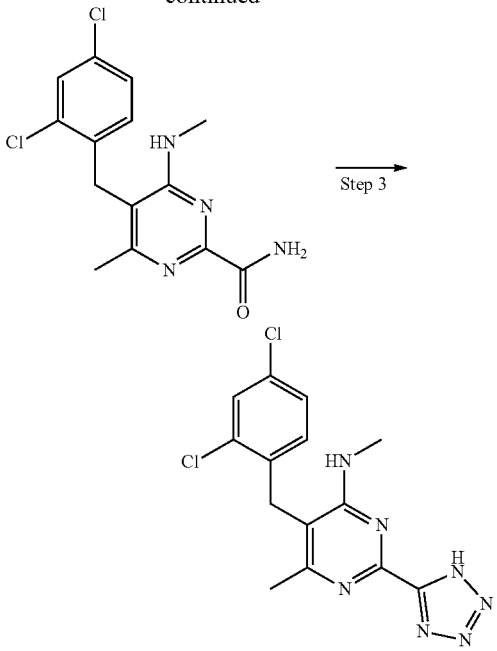

[Step 1]

4-Chloro-5-(2,4-dichlorobenzyl)-6-methylpyrimidine-2-carboxamide

To a suspension of the compound (1 g) obtained in step 5 of Example 1 in chloroform (10 ml), thionyl chloride (0.88 ml) was added, and the mixture was stirred at 80° C. for 3 hours. After cooling, the reaction solution was concentrated under reduced pressure, and the residue obtained was dissolved in tetrahydrofuran (15 ml). This solution was cooled to −78° C. An aqueous ammonia solution (28%, 1.5 ml) was added thereto, and the mixture was stirred at the same temperature as above for 30 minutes. The temperature of the reaction solution was raised to 0° C., and 2 M hydrochloric acid (13 ml) was added thereto, followed by extraction with chloroform. The extract was washed with water and then dried over anhydrous sodium sulfate. The solvent was distilled off under reduced pressure, and the residue obtained was purified by silica gel column chromatography (chloroform/methanol) to obtain the title compound (930 mg).

MS (m/z): 330 (M+H)$^{+}$.

[Step 2]

5-(2,4-Dichlorobenzyl)-4-methyl-6-(methylamino)pyrimidine-2-carboxamide

To a solution of the compound (110 mg) obtained in step 1 above in ethanol (2.5 ml), an aqueous methylamine solution (40%, 0.23 ml) was added, and the mixture was stirred at 115° C. for 45 minutes under microwave irradiation. The reaction solution was concentrated under reduced pressure, and the residue obtained was purified by silica gel column chromatography (chloroform/methanol) to obtain the title compound (81 mg).

$^{1}$H-NMR (CDCl$_{3}$) δ: 2.46 (3H, s), 3.02 (3H, d, J=4.8 Hz), 3.90 (2H, s), 4.58 (1H, br s), 5.65 (1H, br s), 6.66 (1H, d, J=8.0 Hz), 7.13 (1H, dd, J=8.0, 2.1 Hz), 7.47 (1H, d, J=2.1 Hz), 7.80 (1H, br s).

MS (m/z): 325 (M+H)$^{+}$.

[Step 3]

5-(2,4-Dichlorobenzyl)-N,6-dimethyl-2-(1H-tetrazol-5-yl)pyrimidin-4-amine

To a solution of the compound (80 mg) obtained in step 2 above in acetonitrile (6 ml), sodium azide (160 mg) and tetrachlorosilane (0.14 ml) were added, and the mixture was stirred at 90° C. for 6 hours. After cooling, the reaction solution was diluted with ethyl acetate, washed with water and saturated saline in this order, and then dried over anhydrous sodium sulfate. The solvent was distilled off under reduced pressure, and the residue obtained was purified by column chromatography (chloroform/methanol) using diol-modified silica gel to obtain the title compound (24 mg).

$^1$H-NMR (CD$_3$OD) δ: 2.35 (3H, s), 3.13 (3H, s), 4.01 (2H, s), 6.84 (1H, d, J=8.0 Hz), 7.23 (1H, dd, J=8.0, 2.1 Hz), 7.55 (1H, d, J=2.1 Hz).

MS (m/z): 350 (M+H)$^+$.

The following compound was obtained by the same method as Example 105.

TABLE 17

| Example | Name and Structure | Instrumental data |
|---|---|---|
| 106 | 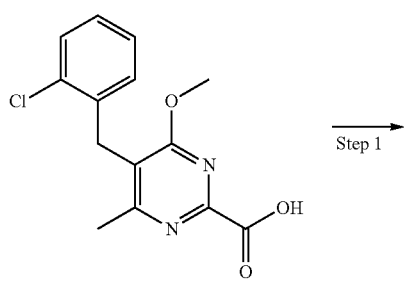<br>5-((2,4-Dichlorophenyl)thio)-N,6-dimethyl-2-(1H-tetrazol-5-yl)pyrimidin-4-amine | $^1$H-NMR (CD$_3$OD) δ: 1.99-2.46 (3H, m), 2.91-3.09 (3H, m), 6.66 (1H, d, J = 8.8 Hz), 7.22 (1H, br s), 7.46 (1H, d, J = 1.8 Hz).<br>MS (m/z): 368 (M + H)$^+$. |

Example 107

5-(2-Chlorobenzyl)-4-methoxy-6-methylpyrimidine-2-carboxylic acid ³⁄₂-hydrate

[Formula 38]

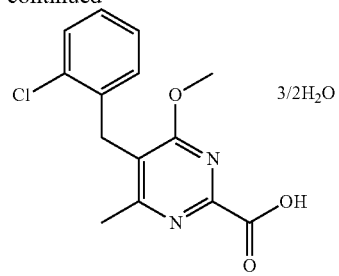

[Step 1]

5-(2-Chlorobenzyl)-4-methoxy-6-methylpyrimidine-2-carboxylic acid ³⁄₂-hydrate To the compound (200 mg) obtained in step 6 of Example 38, 2-propanol (1.8 ml) and water (0.2 ml) were added, and the mixture was stirred at 95° C. for 15 minutes. After cooling to room temperature, the mixture was stirred overnight at room temperature. The precipitate was collected by filtration, washed with water, and then dried to obtain the title compound (188 mg).

$^1$H-NMR (CDCl$_3$) δ: 2.46 (3H, s), 4.09 (3H, s), 4.14 (2H, s), 6.66-6.69 (1H, m), 7.12 (1H, td, J=7.5, 1.5 Hz), 7.19 (1H, td, J=7.7, 1.8 Hz), 7.42 (1H, dd, J=7.9, 1.4 Hz).

Anal. Calcd for $C_{14}H_{13}Cl_1N_2O_3$·3/2H$_2$O: C, 52.59; H, 5.04; Cl, 11.09; N, 8.76.

Found: C, 52.40; H, 5.07; Cl, 11.17; N, 8.70.

FIG. 6 shows the diffraction pattern of a compound obtained in the same way as above in powder X-ray diffraction (CuKα, λ=1.54 angstroms, scan rate=2°/min). Main peaks with high relative intensity in FIG. 6 are shown in Table 18.

TABLE 18

| Peak No. | 2θ | d value | Relative intensity |
|---|---|---|---|
| 1 | 6.68 | 13.22 | 10 |
| 2 | 10.54 | 8.39 | 100 |
| 3 | 16.16 | 5.48 | 23 |
| 4 | 20.16 | 4.40 | 12 |
| 5 | 21.22 | 4.18 | 60 |
| 6 | 21.58 | 4.11 | 17 |
| 7 | 24.20 | 3.67 | 16 |
| 8 | 25.16 | 3.54 | 17 |
| 9 | 33.92 | 2.64 | 9 |

REFERENCE EXAMPLE 1

2-Methoxyacetimidamide hydrochloride

[Formula 39]

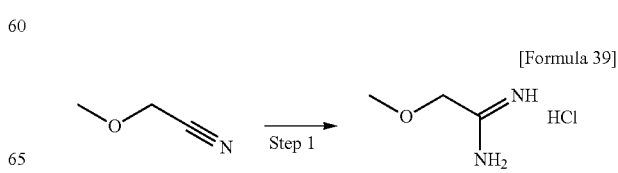

[Step 1]

2-Methoxyacetimidamide hydrochloride

To a solution of 2-methoxyacetonitrile (47.9 g) in methanol (240 ml), sodium methoxide (3.64 g) was added, and the mixture was stirred at room temperature for 3 hours. Ammonium chloride (36.1 g) was added to the reaction solution, and the mixture was stirred overnight at 40° C. The precipitate was removed by filtration, and the filtrate was concentrated under reduced pressure. The residue obtained was dissolved in 2-propanol (50 ml). Acetone (200 ml) was added to the solution, and the mixture was stirred at room temperature for 3.5 hours. The precipitate was removed by filtration, and the filtrate was concentrated under reduced pressure to obtain the title compound (73.35 g).

$^1$H-NMR (DMSO-$d_6$) δ: 3.35 (3H, s), 4.25 (2H, s), 9.06 (4H, br s).

REFERENCE EXAMPLE 2

2-(tert-Butoxy)acetimidamide hydrochloride

[Formula 40]

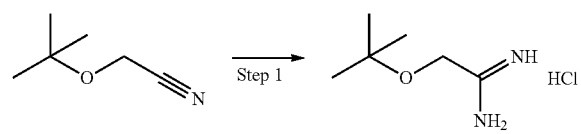

[Step 1]

2-(tert-Butoxy)acetimidamide hydrochloride

To a solution of 2-(tert-butoxy)acetonitrile (Nature Chemistry, 2010, 937-943) (69.89 g) in methanol (400 ml), sodium methoxide (3.08 g) was added, and the mixture was stirred at room temperature for 8 hours. Ammonium chloride (34.69 g) was added to the reaction solution, and the mixture was stirred overnight at 40° C. and then stirred overnight at room temperature. The precipitate was removed by filtration, and the filtrate was concentrated under reduced pressure. Ethanol (400 ml) was added to the residue obtained, and the mixture was stirred at 80° C. for 30 minutes. The precipitate was removed by filtration, and the filtrate was concentrated under reduced pressure. Ethyl acetate (300 ml) was added to the residue obtained, then n-hexane (300 ml) was added dropwise with stirring at 40° C., and the mixture was stirred overnight at room temperature. The suspension was filtered to obtain the title compound (68.57 g).

$^1$H-NMR (DMSO-$d_6$) δ: 1.19 (9H, s), 4.21 (2H, s), 8.61 (4H, br s).

REFERENCE EXAMPLE 3 trans-3-Hydroxycyclobutanecarbonitrile

[Formula 41]

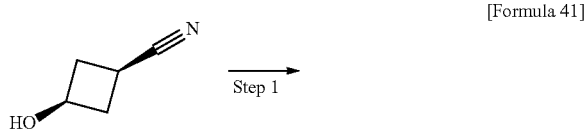

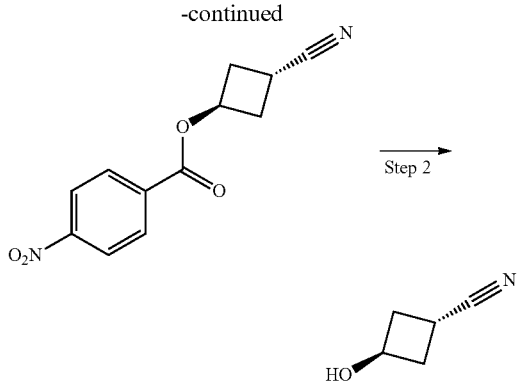

[Step 1]

trans-3-Cyanocyclobutyl 4-nitrobenzoate

To a solution of cis-3-hydroxycyclobutanecarbonitrile (WO2013/30138) (247 mg), 4-nitrobenzoic acid (850 mg) and triphenylphosphine (1.34 g) in tetrahydrofuran (13 ml), diisopropyl azodicarboxylate (0.52 ml) was added under an argon atmosphere, and the mixture was stirred at room temperature for 15 hours. The reaction solution was concentrated under reduced pressure, and the residue obtained was purified by silica gel column chromatography (chloroform/ethyl acetate) and recrystallized with ethyl acetate/n-hexane to obtain the title compound (169 mg).

$^1$H-NMR (CDCl$_3$) δ: 2.62-2.75 (2H, m), 2.88-3.01 (2H, m), 3.22-3.32 (1H, m), 5.49-5.59 (1H, m), 8.18-8.22 (2H, m), 8.28-8.32 (2H, m).

[Step 2]

trans-3-Hydroxycyclobutanecarbonitrile

To a solution of the compound (169 mg) obtained in step 1 above in tetrahydrofuran (6.8 ml), a 2 M aqueous sodium hydroxide solution (1.7 ml) was added, and the mixture was stirred at room temperature for 15 hours. The reaction solution was diluted with water, followed by extraction with ethyl acetate. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (60.7 mg).

$^1$H-NMR (CDCl$_3$) δ: 1.97 (1H, d, J=4.8 Hz), 2.28-2.42 (2H, m), 2.60-2.74 (2H, m), 3.01-3.12 (1H, m), 4.63-4.71 (1H, m).

Example 108

Magnesium bis[5-(2-chlorobenzyl)-4-methoxy-6-methylpyrimidine-2-carboxylate]

To a compound (301.89 mg) obtained in the same way as in Example 107, 2-propanol (1208 μl) and water (3302 μl) were added. To this solution, a 1.0 mol/l aqueous potassium hydroxide solution (989 μl) was added, and then, a 1.0 mol/l aqueous magnesium chloride solution (539 μl) was added. This mixed solution was stirred at 40° C. for approximately 24 hours and subsequently left at room temperature for approximately 0.5 hours. The solid was collected by filtration and dried overnight at room temperature. Then, water (6.0 ml) was added thereto, and the mixture was stirred at room temperature for approximately 2 hours. The solid was collected by filtration and dried overnight at room temperature to obtain the title compound (274.93 mg, recovery rate: 88%).

Elemental analysis values as $C_{28}H_{24}Cl_2MgN_4O_6 \cdot 3.0H_2O$
Calcd: C, 50.82; H, 4.57; N, 8.47; Cl, 10.71; Mg, 3.67.
Found: C, 50.63; H, 4.69; N, 8.41; Cl, 10.88; Mg, 3.63.

From the results mentioned above, the compound obtained was presumed to be magnesium bis[5-(2-chlorobenzyl)-4-methoxy-6-methylpyrimidine-2-carboxylate] hydrate.

FIG. 7 shows the powder X-ray diffraction pattern (CuKα, λ=1.54 angstroms, scan rate=20°/min). Main peaks with high relative intensity in FIG. 7 are shown in Table 19.

TABLE 19

| Peak No. | 2θ | d value | Relative intensity |
|---|---|---|---|
| 1 | 5.18 | 17.05 | 100 |
| 2 | 10.44 | 8.47 | 19 |
| 3 | 18.98 | 4.67 | 17 |
| 4 | 19.68 | 4.51 | 10 |
| 5 | 22.36 | 3.97 | 12 |
| 6 | 23.76 | 3.74 | 21 |
| 7 | 26.34 | 3.38 | 28 |
| 8 | 27.96 | 3.19 | 19 |

Example 109

Magnesium bis[5-(2-chlorobenzyl)-4-methoxy-6-methylpyrimidine-2-carboxylate]

To a compound (1501 mg) obtained in the same way as in Example 107, 2-propanol (6005 μl) and water (16.42 ml) were added. To this solution, a 1.0 mol/l aqueous potassium hydroxide solution (4920 μl) was added, and then, a 1.0 mol/l aqueous magnesium chloride solution (2679 μl) was added. This mixed solution was stirred at 40° C. for approximately 2 days. Then, a small amount of seed crystals obtained in the same way as the method given below was added thereto, and the mixture was further stirred at 40° C. for approximately 1 day and subsequently left at room temperature for approximately 0.5 hours. The solid was collected by filtration. Water (30.0 ml) was added thereto, and the mixture was stirred at room temperature for approximately 2 hours. The solid was collected by filtration and dried overnight at room temperature to obtain the title compound (1416 mg, recovery rate: 93%).

Method for Obtaining Seed Crystals

A compound (701.13 mg) obtained in the same way as in Example 108 was dissolved by the addition of a 1,4-dioxane/dimethyl sulfoxide (1/1) solution (30 ml). 428 μl of this solution was dispensed, and the solvent was distilled off by freeze drying. 20% aqueous 2-propanol (100 μl) was added to the freeze-dried product obtained, and the mixture was stirred at 40° C. for approximately 24 hours. Then, the solid was collected by filtration and dried overnight at room temperature to obtain seed crystals.

Elemental analysis values as $C_{28}H_{24}Cl_2MgN_4O_6 \cdot 2H_2O$
Calcd: C, 52.24; H, 4.38; N, 8.70; Cl, 11.01; Mg, 3.78.
Found: C, 51.82; H, 4.52; N, 8.64; Cl, 10.90; Mg, 3.70.
Moisture content values (Karl Fischer method) as $C_{28}H_{24}Cl_2MgN_4O_6 \cdot 2H_2O$
Calcd: 5.58%.
Found: 6.10%.
Rate of decrease in mass (thermal analysis TG-DTA) as $C_{28}H_{24}Cl_2MgN_4O_6 \cdot 2H_2O$
Calcd: 5.58%.
Found: 5.61%.

From the measurement results mentioned above, the compound obtained was presumed to be monomagnesium bis[5-(2-chlorobenzyl)-4-methoxy-6-methylpyrimidine-2-carboxylate] dihydrate.

FIG. 8 shows the powder X-ray diffraction pattern (CuKα, λ=1.54 angstroms, scan rate=20°/min). Main peaks with high relative intensity in FIG. 8 are shown in Table 20.

TABLE 20

| Peak No. | 2θ | d value | Relative intensity |
|---|---|---|---|
| 1 | 11.82 | 7.48 | 52 |
| 2 | 13.74 | 6.44 | 51 |
| 3 | 14.26 | 6.21 | 75 |
| 4 | 15.38 | 5.76 | 59 |
| 5 | 21.56 | 4.12 | 37 |
| 6 | 23.42 | 3.80 | 100 |
| 7 | 24.14 | 3.68 | 92 |
| 8 | 27.82 | 3.20 | 33 |
| 9 | 28.72 | 3.11 | 34 |
| 10 | 31.06 | 2.88 | 31 |

Example 110

Calcium bis[5-(2-chlorobenzyl)-4-methoxy-6-methylpyrimidine-2-carboxylate]

To a compound (300.93 mg) obtained in the same way as in Example 107, 2-propanol (1202 μl) and water (3284 μl) were added. To this solution, a 1.0 mol/l aqueous potassium hydroxide solution (985 μl) was added, and then, a 1.0 mol/l aqueous calcium chloride solution (538 μl) was added. This mixed solution was stirred at 40° C. for approximately 24 hours and subsequently left at room temperature for approximately 0.5 hours. The solid was collected by filtration and dried overnight at room temperature. Then, water (6.0 ml) was added thereto, and the mixture was stirred at room temperature for approximately 2 hours. The solid was collected by filtration and dried overnight at room temperature to obtain the title compound (301.22 mg, recovery rate: 92%).

Elemental analysis values as $C_{28}H_{24}Cl_2CaN_4O_6 \cdot 4.0H_2O$
Calcd: C, 48.35; H, 4.64; N, 8.05; Cl, 10.19; Ca, 5.76.
Found: C, 48.10; H, 4.74; N, 7.98; Cl, 10.26; Ca, 4.28.

From the results mentioned above, the compound obtained was presumed to be calcium bis[5-(2-chlorobenzyl)-4-methoxy-6-methylpyrimidine-2-carboxylate] hydrate.

FIG. 9 shows the powder X-ray diffraction pattern (CuKα, λ=1.54 angstroms, scan rate=20°/min). Main peaks with high relative intensity in FIG. 9 are shown in Table 21.

TABLE 21

| Peak No. | 2θ | d value | Relative intensity |
|---|---|---|---|
| 1 | 5.94 | 14.87 | 100 |
| 2 | 7.40 | 11.94 | 30 |
| 3 | 11.62 | 7.61 | 13 |
| 4 | 11.96 | 7.39 | 14 |
| 5 | 13.98 | 6.33 | 60 |
| 6 | 14.88 | 5.95 | 31 |
| 7 | 19.52 | 4.54 | 13 |
| 8 | 22.32 | 3.98 | 12 |

TABLE 21-continued

| Peak No. | 2θ | d value | Relative intensity |
|---|---|---|---|
| 9 | 23.76 | 3.74 | 13 |
| 10 | 24.80 | 3.59 | 18 |

Example 111

Zinc bis[5-(2-chlorobenzyl)-4-methoxy-6-methylpyrimidine-2-carboxylate]

To a compound (300.10 mg) obtained in the same way as in Example 107, 2-propanol (1200 μl) and water (3280 μl) were added. To this solution, a 1.0 mol/l aqueous potassium hydroxide solution (984 μl) was added, and then, a 1.0 mol/l aqueous zinc bromide solution (538 μl) was added. This mixed solution was stirred at 40° C. for approximately 24 hours and subsequently left at room temperature for approximately 0.5 hours. The solid was collected by filtration and dried overnight at room temperature. Then, water (6.0 ml) was added thereto, and the mixture was stirred at room temperature for approximately 2 hours. The solid was collected by filtration and dried overnight at room temperature to obtain the title compound (293.65 mg, recovery rate: 92%).

Elemental analysis values as $C_{28}H_{24}Cl_2ZnN_4O_6 \cdot 1.5H_2O$
Calcd: C, 49.76; H, 4.03; N, 8.29; Cl, 10.49.
Found: C, 49.94; H, 4.12; N, 8.28; Cl, 10.61.

From the results mentioned above, the compound obtained was presumed to be zinc bis[5-(2-chlorobenzyl)-4-methoxy-6-methylpyrimidine-2-carboxylate] hydrate.

FIG. 10 shows the powder X-ray diffraction pattern (CuKα, λ=1.54 angstroms, scan rate=20°/min). Main peaks with high relative intensity in FIG. 10 are shown in Table 22.

TABLE 22

| Peak No. | 2θ | d value | Relative intensity |
|---|---|---|---|
| 1 | 6.10 | 14.48 | 97 |
| 2 | 12.28 | 7.20 | 100 |
| 3 | 13.44 | 6.58 | 13 |
| 4 | 14.08 | 6.28 | 25 |
| 5 | 15.34 | 5.77 | 35 |
| 6 | 19.16 | 4.63 | 24 |
| 7 | 21.78 | 4.08 | 30 |
| 8 | 23.60 | 3.77 | 21 |
| 9 | 24.70 | 3.60 | 22 |
| 10 | 31.76 | 2.82 | 17 |

Example 112

Sodium 5-(2-Chlorobenzyl)-4-methoxy-6-methylpyrimidine-2-carboxylate

To a compound (301.24 mg) obtained in the same way as in Example 107, ethanol (5042 μl) was added, and a 1.0 mol/l solution of sodium hydroxide in ethanol (982 μl) was added. This mixed solution was stirred at 40° C. for approximately 24 hours and subsequently left at room temperature for approximately 0.5 hours. The solid was collected by filtration and dried overnight at room temperature to obtain the title compound (289.98 mg, recovery rate: 97%).

FIG. 11 shows the powder X-ray diffraction pattern (CuKα, λ=1.54 angstroms, scan rate=20°/min). Main peaks with high relative intensity in FIG. 11 are shown in Table 23.

TABLE 23

| Peak No. | 2θ | d value | Relative intensity |
|---|---|---|---|
| 1 | 5.64 | 15.66 | 51 |
| 2 | 6.00 | 14.72 | 100 |
| 3 | 9.68 | 9.13 | 44 |
| 4 | 16.40 | 5.40 | 21 |
| 5 | 18.16 | 4.88 | 29 |
| 6 | 24.30 | 3.66 | 66 |
| 7 | 25.54 | 3.48 | 17 |

Example 113

Tert-butylammonium 5-(2-Chlorobenzyl)-4-methoxy-6-methylpyrimidine-2-carboxylate To a compound (300.90 mg) obtained in the same way as in Example 107, acetone (5913 μl) was added, and tert-butylamine (105 μl) was added. This mixed solution was stirred at 40° C. for approximately 24 hours and subsequently left at room temperature for approximately 0.5 hours. The solid was collected by filtration and dried overnight at room temperature to obtain the title compound (332.74 mg, recovery rate: 97%).

Elemental analysis values as $C_{14}H_{13}C_1N_2O_3 \cdot 1.0C_4H_{11}N$
Calcd: C, 59.09; H, 6.61; N, 11.49; Cl, 9.69.
Found: C, 58.69; H, 6.53; N, 11.34; Cl, 9.74.

FIG. 12 shows the powder X-ray diffraction pattern (CuKα, λ=1.54 angstroms, scan rate=20°/min). Main peaks with high relative intensity in FIG. 12 are shown in Table 24.

TABLE 24

| Peak No. | 2θ | d value | Relative intensity |
|---|---|---|---|
| 1 | 6.84 | 12.91 | 77 |
| 2 | 9.34 | 9.46 | 69 |
| 3 | 13.66 | 6.48 | 100 |
| 4 | 15.38 | 5.76 | 38 |
| 5 | 17.92 | 4.95 | 29 |
| 6 | 18.36 | 4.83 | 42 |
| 7 | 22.04 | 4.03 | 54 |
| 8 | 22.52 | 3.94 | 30 |
| 9 | 23.12 | 3.84 | 72 |
| 10 | 30.24 | 2.95 | 32 |

Example 114

Diisopropylamine 5-(2-Chlorobenzyl)-4-methoxy-6-methylpyrimidine-2-carboxylate

To a compound (300.05 mg) obtained in the same way as in Example 107, acetone (5863 μl) was added, and diisopropylamine (138 μl) was added. This mixed solution was stirred at 40° C. for approximately 24 hours and subsequently left at room temperature for approximately 0.5 hours. The solid was collected by filtration and dried overnight at room temperature to obtain the title compound (353.95 mg, recovery rate: 96%).

Elemental analysis values as $C_{14}H_{13}C_1N_2O_3 \cdot 1.0C_6H_{15}N$
Calcd: C, 60.98; H, 7.16; N, 10.67; Cl, 9.00.
Found: C, 60.89; H, 7.17; N, 10.65; Cl, 9.05.

FIG. 13 shows the powder X-ray diffraction pattern (CuKα, λ=1.54 angstroms, scan rate=20°/min). Main peaks with high relative intensity in FIG. 13 are shown in Table 25.

TABLE 25

| Peak No. | 2θ | d value | Relative intensity |
|---|---|---|---|
| 1 | 13.00 | 6.80 | 80 |
| 2 | 13.34 | 6.63 | 42 |
| 3 | 14.06 | 6.29 | 100 |
| 4 | 17.58 | 5.04 | 90 |
| 5 | 20.44 | 4.34 | 33 |
| 6 | 20.98 | 4.23 | 44 |
| 7 | 22.80 | 3.90 | 41 |
| 8 | 23.38 | 3.80 | 79 |
| 9 | 25.60 | 3.48 | 50 |
| 10 | 26.96 | 3.30 | 72 |

FORMULATION EXAMPLE

After mixing 5 g of a compound obtained in the Examples, 90 g of lactose, 34 g of corn starch, 20 g of crystalline cellulose, and 1 g of magnesium stearate with a blender, tablets are then produced with a tabletting machine.

TEST EXAMPLE 1

Examination of Secretory Activity for Chloride Ions of Test Compounds

Measurement of the secretory activity for chloride ions was performed in accordance with a previous report (West and Molloy, 1996). CuFi-1 cells were plated on a 96 well plate in $3 \times 10^4$ cells/well and incubated for two nights. After removing the culture medium, 100 μL/well of N-(ethoxycarbonylmethyl)-6-methoxyquinolinium bromide (MQAE) (diluted with culture medium and the concentration adjusted to 5 mM) was added. After the addition of MQAE, the cells were incubated for one night so that the indicator was passively loaded. After the loading, the cells were washed two times with Assay buffer, and 100 μL/well of Assay buffer was added. The secretory capacity for chloride ions was measured using FlexStation 1 (fluorescence wavelength of Ex: 355 nm/Em: 460 nm). In order to measure the basic value, nothing was added for 34 seconds immediately after the start of the measurement. Then, at this point, 100 μL/well of the test compound and zinc (final concentration: 10 μM) diluted with Assay buffer, which is free of chloride ions, was added, and the measurement was continued for 86 seconds (total measurement time: 120 seconds). The secretory capacity for chloride ions was calculated by dividing the average of RFU values in 10 seconds between 110 seconds and 120 seconds after the start of the measurement with the average between 0 second and 34 seconds (the basic value). The secretory activity for chloride ions of the test compound ($EC_{50}$ value) was calculated by obtaining the secretory capacity for chloride ions at each concentration of the serially diluted test compound, and determining a concentration of the test compound that provides a secretory capacity of 50% from two secretory capacities and concentrations sandwiching 50% of the maximum response of each compound.

The results are described in Table 26.

TABLE 26

| Example No. | $EC_{50}$ (nM) |
|---|---|
| 1 | 9.4 |
| 2 | 24.2 |
| 3 | 53.0 |
| 4 | 19.6 |
| 5 | 30.3 |
| 6 | 50.3 |
| 7 | 41.7 |
| 8 | 50.6 |
| 9 | 5.5 |
| 10 | 7.3 |
| 11 | 11.1 |
| 12 | 6.7 |
| 13 | 5.6 |
| 14 | 5.0 |
| 15 | 10.8 |
| 16 | 52.7 |
| 17 | 15.7 |
| 18 | 4.6 |
| 19 | 13.1 |
| 20 | 5.9 |
| 21 | 18.6 |
| 22 | 7.1 |
| 23 | 86.0 |
| 24 | 12.9 |
| 25 | 14.6 |
| 26 | 14.4 |
| 27 | 14.0 |
| 28 | 2.8 |
| 29 | 6.9 |
| 30 | 9.5 |
| 31 | 34.9 |
| 32 | 17.1 |
| 33 | 18.4 |
| 34 | 80.1 |
| 35 | 29.3 |
| 36 | 80.6 |
| 37 | 30.3 |
| 38 | 10.0 |
| 39 | 5.5 |
| 40 | 8.1 |
| 41 | 16.3 |
| 42 | 7.6 |
| 43 | 66.7 |
| 44 | 9.4 |
| 45 | 14.7 |
| 46 | 15.9 |
| 47 | 8.6 |
| 48 | 9.4 |
| 49 | 24.8 |
| 50 | 10.2 |
| 51 | 8.2 |
| 52 | 15.8 |
| 53 | 15.8 |
| 54 | 15.4 |
| 55 | 7.6 |
| 56 | 16.0 |
| 57 | 20.8 |
| 58 | 13.0 |
| 59 | 24.6 |
| 60 | 12.0 |
| 61 | 11.4 |
| 62 | 4.9 |
| 63 | 4.8 |
| 64 | 14.9 |
| 65 | — |
| 66 | 17.4 |
| 67 | 15.9 |
| 68 | 4.0 |
| 69 | 26.7 |
| 70 | 59.9 |
| 71 | 30.2 |
| 72 | 2.6 |
| 73 | 35.2 |
| 74 | 33.4 |
| 75 | 3.7 |
| 76 | 15.2 |
| 77 | 14.6 |
| 78 | 4.6 |
| 79 | 6.6 |

TABLE 26-continued

| Example No. | EC$_{50}$ (nM) |
|---|---|
| 80 | 49.4 |
| 81 | 5.5 |
| 82 | 30.8 |
| 83 | 50.7 |
| 84 | 10.4 |
| 85 | 30.2 |
| 86 | 13.1 |
| 87 | 8.2 |
| 88 | 7.1 |
| 89 | 5.1 |
| 90 | 6.4 |
| 91 | 13.2 |
| 92 | 5.1 |
| 93 | 2.2 |
| 94 | 2.2 |
| 95 | 3.3 |
| 96 | 2.4 |
| 97 | 5.7 |
| 98 | 13.5 |
| 99 | 5.1 |
| 100 | 11.1 |
| 101 | 8.9 |
| 102 | 5.2 |
| 103 | 20.8 |
| 104 | 9.9 |
| 105 | 2.1 |
| 106 | 2.9 |

It is to be noted that the compounds of Example 38 and Examples 107 to 114 are an anhydride, hydrates, or different types of salts or hydrates thereof, derived from the same compound. In Test Examples 1 to 3, a compound from any of these Examples was used as a test compound.

TEST EXAMPLE 2

Effects of GPR39 Knockdown on Chloride Secretion by Test Compounds

In order to confirm that chloride ion secretion by the test compound observed in Test. Example 1 was induced via GPR39, GPR39 knockdown was conducted. CuFi-1 cells cultured in Pneumacult-EX (STEMCELL Technologies Inc.) were plated on a 96 well plate in 3×10⁴ cells/100 µL/well. Then, human GPR39 siRNA (MISSION siRNA SASI_Hs02_00332000, SASI_Hs02_00332001, Sigma-Aldrich Co. LLC) or control siRNA (Ambion Silencer Select, Thermo Fisher Scientific Inc.) was added in 1 pmol/10 µL/well using Lipofectamine RNAiMAX (Thermo Fisher Scientific Inc.), and the cells were incubated for two nights. In order for the final concentration to be 5 mM, 10 µL/well of N-(ethoxycarbonylmethyl)-6-methoxyquinolinium bromide (MQAE) diluted with culture medium was added. After the addition of MQAE, the cells were incubated for one night so that the indicator was passively loaded. Hereafter, washing and measurement of the secretory capacity for chloride ions were conducted in the same way as Test Example 1. In addition, analysis on gene expression of GPR39 was performed using RNA extracted from wells to which the same method was carried out. Total RNA was extracted from cells using RNAiso Plus (Takara Bio Inc.), and purified using RNeasy Micro Kit (Qiagen). Then, cDNA was synthesized using High Capacity cDNA Reverse Transcription Kit (Thermo Fisher Scientific Inc.), and quantitative PCR was conducted using TaqMan Gene Expression Assays (human GPR39: Hs00230762_m1, human GAPDH: Hs02758991_g1, Thermo Fisher Scientific Inc.) and THUNDERBIRD Probe qPCR Mix (TOYOBO CO., LTD.). Through the calibration curve method, a relative expression level of GPR39 compensated with GAPDH was calculated. The results are shown in FIG. 1 and FIG. 2.

With the siRNA treatment, GPR39 knockdown was confirmed (See FIG. 1. siGPR39-1: 17%, siGPR39-2: 15% versus control siRNA). In GPR39 knockdown conditions, the chloride ion secretion by the test compound (the compound of Example 107) in CuFi-1 cells was remarkably suppressed, compared to the control siRNA treated group (See FIG. 2. siGPR39-1: 17%, siGPR39-2: 37% versus control siRNA). The chloride ion secretion by UTP was not affected by the GPR39 knockdown (See FIG. 2. siGPR39-1: 111%, siGPR39-2: 89% versus control siRNA). As such, it was shown that the chloride secretion by the test compound in CuFi-1 cells was induced via GPR39.

TEST EXAMPLE 3

Effects of Test Compound in ALI Assay Using Fluid Transfer as an Indicator

MucilAir-CF™ cells were commercially obtained from Epithelix Sarl. The cells are obtained by ALI (Air-Liquid Interface) culturing primary bronchial epithelial cells from patients with cystic fibrosis having ΔF508 homozygous mutation (class II mutation), 2184ΔA+W1282X (class I mutation), and N1303K heterozygous mutation (class II mutation). After the acquisition, the resistance value, mucin production, and ciliary movement were confirmed, followed by addition of 200 µL of HBSS (+) into the upper layer and washing of mucin. Into the upper layer, a volume of 100 µL/well of culture medium was added, and into the lower layer, a volume of 500 µL/well of culture medium, in which the test compound and zinc (final concentration: 10 µM) were dissolved, was added. The weight of the culture medium in the upper layer was measured 72 hours after the addition of the test compound, and the fluid transfer activity of the test compound was determined. As control drugs, effects of single VX-809 (lumacaftor) (Selleck Chemicals), and a combination of VX-809 (lumacaftor) and VX-770 (ivacaftor) (Selleck Chemicals) were also examined. As the test compound, the compound of Example 38 was used. The results are shown in FIGS. 3, 4 and 5.

In the ALI culture with ΔF508 homozygous mutation, the compound of Example 38 induced the fluid transfer in a concentration-dependent manner. Its effects were on the same level as the single VX-809 and the combination of VX-809 and VX-770. Furthermore, in mutations other than the ΔF508 homozygous mutation (2184ΔA+W1282X (class I mutation) and N1303K heterozygous mutation), the compound of Example 38 also showed activities equivalent to that in the ΔF508 homozygous mutation, showing a possibility of being effective independent of CFTR mutation. However, the combination of VX-809 and VX-770 had weak effects in 2184ΔA+W1282X (class I mutation), and it is believed that the effects were dependent on CFTR mutation. In particular, the effects of the compound of Example 38 in 2184ΔA+W1282X (class I mutation) were significant relative to the combination of VX-809 and VX-770.

INDUSTRIAL APPLICABILITY

A compound of the present invention represented by general formula (I) or a pharmaceutically acceptable salt thereof has strong chloride ion-secretory action via GPR39 agonism and moves moisture. Therefore, a compound of the present invention or a pharmaceutically acceptable salt thereof is useful as a therapeutic agent for cystic fibrosis, non-CF bronchiectasis, primary ciliary dyskinesia, dry eye, constipation, adiposity, diabetes mellitus, ulcerative colitis, Crohn's disease, depression, COPD, and the like.

The invention claimed is:

1. A compound represented by general formula (I):

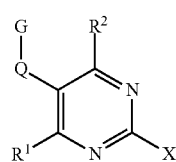

wherein,

X represents a carboxyl group or a tetrazolyl group;

Q represents a $C_1$-$C_3$ alkylene group, an oxygen atom, a sulfur atom, or $R^aN$, where $R^a$ represents a hydrogen atom or a $C_1$-$C_3$ alkyl group;

G represents a phenyl group, where the phenyl group may have 1 to 3 substituents independently selected from the group consisting of a halogen atom, a cyano group, a $C_1$-$C_6$ alkyl group, a $C_1$-$C_3$ alkoxy group, and a trihalo $C_1$-$C_6$ alkyl group;

$R^1$ represents a $C_1$-$C_6$ alkyl group, a $C_1$-$C_3$ alkoxy $C_1$-$C_6$ alkyl group, or a $C_3$-$C_6$ cycloalkyl group; and $R^2$ represents a $C_1$-$C_6$ alkyl group that may have 1 to 3 substituents independently selected from the following group A, or a group selected from the following group B, or a pharmaceutically acceptable salt thereof:

Group A: a phenyl group and a pyridyl group, wherein the phenyl group and the pyridyl group may have 1 to 3 substituents independently selected from the following group D;

Group B: —O-M, —SH, —S-M, —$NH_2$, —NH-M, and —N-$M_2$, wherein M is a $C_1$-$C_6$ alkyl group that may have 1 or 2 substituents independently selected from the following group C, or a $C_3$-$C_6$ cycloalkyl group that may have 1 or 2 substituents independently selected from the following group C;

Group C: a halogen atom, a hydroxy group, a cyano group, a carbamoyl group, a carboxyl group, a $C_1$-$C_6$ alkoxycarbonyl group, a $C_1$-$C_3$ alkoxy group, a phenyl group, and a pyridyl group, wherein the phenyl group and the pyridyl group may have 1 to 3 substituents independently selected from the following group D; and Group D: a halogen atom, a cyano group, a $C_1$-$C_6$ alkyl group, a $C_1$-$C_6$ alkoxy group, and a trihalo $C_1$-$C_6$ alkyl group.

2. A compound or a pharmaceutically acceptable salt thereof according to claim 1, wherein, in formula (I), X represents a carboxyl group.

3. A compound or a pharmaceutically acceptable salt thereof according to claim 1, wherein, in formula (I), Q represents a methylene group, an oxygen atom, or a sulfur atom.

4. A compound or a pharmaceutically acceptable salt thereof according to claim 1, wherein, in formula (I), G is a phenyl group having 1 to 3 substituents independently selected from the group consisting of a chlorine atom, a fluorine atom, a cyano group, a $C_1$-$C_3$ alkyl group, a $C_1$-$C_3$ alkoxy group and a trihalomethyl group, or an unsubstituted phenyl group.

5. A compound or a pharmaceutically acceptable salt thereof according to claim 1, wherein, in formula (I), G is a phenyl group having 1 to 2 substituents independently selected from the group consisting of a chlorine atom and a fluorine atom.

6. A compound or a pharmaceutically acceptable salt thereof according to claim 1, wherein, in formula (I), $R^1$ represents a $C_1$-$C_6$ alkyl group.

7. A compound or a pharmaceutically acceptable salt thereof according to claim 1, wherein, in formula (I), $R^2$ is a $C_1$-$C_6$ alkyl group that may be substituted with one pyridyl group, or —O-M, —S-M, —NH-M, wherein M is a $C_1$-$C_6$ alkyl group that may have 1 or 2 substituents independently selected from the following group $C^1$, or a $C_3$-$C_6$ cycloalkyl group that may have one substituent independently selected from the following group $C^1$:

Group $C^1$: a halogen atom, a cyano group, a phenyl group, and a pyridyl group, wherein the phenyl group and the pyridyl group may have 1 to 3 substituents independently selected from the following group $D^1$; and Group $D^1$: a halogen atom, a cyano group, a $C_1$-$C_6$ alkyl group.

8. A compound or a pharmaceutically acceptable salt thereof according to claim 1, wherein, in formula (I), Q represents a methylene group, an oxygen atom, or a sulfur atom;

G is a phenyl group having 1 to 2 substituents independently selected from the group consisting of a chlorine atom and a fluorine atom;

$R^1$ is a $C_1$-$C_3$ alkyl group; and $R^2$ is a $C_1$-$C_6$ alkyl group that may be substituted with one pyridyl group, or —O-M, —S-M, —NH-M, wherein M is a $C_1$-$C_6$ alkyl group that may have 1 or 2 substituents independently selected from the following group $C^1$, or a $C_3$-$C_6$ cycloalkyl group that may have one substituent independently selected from the following group $C^1$:

Group $C^1$: a halogen atom, a cyano group, a phenyl group, and a pyridyl group, wherein the phenyl group and the pyridyl group may have 1 to 3 substituents independently selected from the following group $D^1$; and Group $D^1$: a halogen atom, a cyano group, a $C_1$-$C_6$ alkyl group.

9. A compound or a pharmaceutically acceptable salt thereof according to claim 1, wherein the compound is any one selected from the following group:

5-(2,4-dichlorobenzyl)-4-(ethylamino)-6-methylpyrimidine-2-carboxylic acid;

5-((2-chlorophenyl)thio)-4-(ethylamino)-6-methylpyrimidine-2-carboxylic acid;

5-(2-chlorobenzyl)-4-methoxy-6-methylpyrimidine-2-carboxylic acid;

5-(2-chlorobenzyl)-4-ethyl-6-methoxypyrimidine-2-carboxylic acid;

5-(2-chloro-3-fluorobenzyl)-4-ethyl-6-methoxypyrimidine-2-carboxylic acid;

5-(2-chlorobenzyl)-4-ethyl-6-(3-fluoropropoxy)pyrimidine-2-carboxylic acid;

5-(2,4-dichlorobenzyl)-4-methyl-6-(methylthio)pyrimidine-2-carboxylic acid;

4-(benzyloxy)-5-(2-chlorobenzyl)-6-methylpyrimidine-2-carboxylic acid;

5-(2-chlorobenzyl)-4-methyl-6-(pyridin-4-ylmethoxy)pyrimidine-2-carboxylic acid;

5-(2-chlorobenzyl)-4-methyl-6-(2-(pyridin-4-yl)ethyl)pyrimidine-2-carboxylic acid;
5-(2,4-dichlorophenoxy)-4-methyl-6-(methylamino)pyrimidine-2-carboxylic acid;
5-(2,4-dichlorobenzyl)-4-methoxy-6-methylpyrimidine-2-carboxylic acid;
5-(2,3-dichlorobenzyl)-4-ethyl-6-methoxypyrimidine-2-carboxylic acid;
5-(2-chlorobenzyl)-4-ethoxy-6-methylpyrimidine-2-carboxylic acid;
5-(2-chloro-3-fluorobenzyl)-4-ethoxy-6-ethylpyrimidine-2-carboxylic acid;
5-(2,3-dichlorobenzyl)-4-methoxy-6-methylpyrimidine-2-carboxylic acid;
5-(2-chlorobenzyl)-4-(cis-3-cyanocyclobutoxy)-6-methylpyrimidine-2-carboxylic acid;
5-(2,4-dichlorobenzyl)-4,6-dimethylpyrimidine-2-carboxylic acid; and
5-(2,4-dichlorobenzyl)-N,6-dimethyl-2-(1H-tetrazol-5-yl)pyrimidine-4-amine.

10. A compound or a pharmaceutically acceptable salt thereof according to claim 1, wherein the compound is any one selected from the following group:
5-(2,4-dichlorobenzyl)-4-(ethylamino)-6-methylpyrimidine-2-carboxylic acid;
5-((2-chlorophenyl)thio)-4-(ethylamino)-6-methylpyrimidine-2-carboxylic acid;
5-(2-chlorobenzyl)-4-methoxy-6-methylpyrimidine-2-carboxylic acid;
5-(2-chlorobenzyl)-4-ethyl-6-methoxypyrimidine-2-carboxylic acid;
5-(2-chloro-3-fluorobenzyl)-4-ethyl-6-methoxypyrimidine-2-carboxylic acid;
5-(2-chlorobenzyl)-4-ethyl-6-(3-fluoropropoxy)pyrimidine-2-carboxylic acid;
5-(2,4-dichlorobenzyl)-4-methyl-6-(methylthio)pyrimidine-2-carboxylic acid;
4-(benzyloxy)-5-(2-chlorobenzyl)-6-methylpyrimidine-2-carboxylic acid;
5-(2-chlorobenzyl)-4-methyl-6-(pyridin-4-ylmethoxy)pyrimidine-2-carboxylic acid; and
5-(2-chlorobenzyl)-4-methyl-6-(2-(pyridin-4-yl)ethyl)pyrimidine-2-carboxylic acid.

11. A compound or a pharmaceutically acceptable salt thereof according to claim 1, wherein the compound is 5-(2-chlorobenzyl)-4-methoxy-6-methylpyrimidine-2-carboxylic acid.

12. A compound or a pharmaceutically acceptable salt thereof according to claim 1, wherein the compound is 5-(2-chlorobenzyl)-4-ethyl-6-methoxypyrimidine-2-carboxylic acid.

13. A compound or a pharmaceutically acceptable salt thereof according to claim 1, wherein the pharmaceutically acceptable salt is a hydrochloride salt, a trifluoroacetate salt, a magnesium salt, a calcium salt, a zinc salt, a sodium salt, a tert-butylamine salt, or a diisopropylamine salt.

14. A compound or a pharmaceutically acceptable salt thereof according to claim 1, wherein the compound or the pharmaceutically acceptable salt thereof is 5-(2-chlorobenzyl)-4-methoxy-6-methylpyrimidine-2-carboxylic acid, or a magnesium salt, a calcium salt, a zinc salt, a sodium salt, a tert-butylamine salt, or a diisopropylamine salt thereof.

15. A compound or a pharmaceutically acceptable salt thereof according to claim 1, which is a bis[5-(2-chlorobenzyl)-4-methoxy-6-methylpyrimidine-2-carboxylic acid] magnesium salt having a crystal form having main peaks at diffraction angles 2θ=11.82, 13.74, 14.26, 15.38, 21.56, 23.42, 24.14, 27.82, 28.72, and 31.06 in a powder X-ray diffraction pattern obtained by irradiation with copper Kα radiation (wavelength λ=1.54 angstroms).

16. A compound or a pharmaceutically acceptable salt thereof according to claim 1, which is a bis[5-(2-chlorobenzyl)-4-methoxy-6-methylpyrimidine-2-carboxylic acid] magnesium salt having a crystal form having main peaks at diffraction angles 2θ=5.18, 10.44, 18.98, 19.68, 22.36, 23.76, 26.34, and 27.96 in a powder X-ray diffraction pattern obtained by irradiation with copper Kα radiation (wavelength λ=1.54 angstroms).

17. A compound or a pharmaceutically acceptable salt thereof according to claim 1, which is 5-(2-chlorobenzyl)-4-methoxy-6-methylpyrimidine-2-carboxylic acid having a crystal form having main peaks at diffraction angles 2θ=6.68, 10.54, 16.16, 20.16, 21.22, 21.58, 24.20, 25.16, and 33.92 in a powder X-ray diffraction pattern obtained by irradiation with copper Kα radiation (wavelength λ=1.54 angstroms).

18. A pharmaceutical composition comprising a compound or a pharmaceutically acceptable salt thereof according to claim 1.

19. A method for treating cystic fibrosis comprising administering a pharmacologically effective amount of a compound or a pharmaceutically acceptable salt thereof according to claim 1 to a warm-blooded animal.

20. A method for treating cystic fibrosis comprising administering a pharmacologically effective amount of a compound or a pharmaceutically acceptable salt thereof according to claim 11 to a warm-blooded animal.

21. A method for treating cystic fibrosis comprising administering a pharmacologically effective amount of a compound or a pharmaceutically acceptable salt thereof according to claim 12 to a warm-blooded animal.

22. A method for treating cystic fibrosis comprising administering a pharmacologically effective amount of a compound or a pharmaceutically acceptable salt thereof according to claim 14 to a warm-blooded animal.

23. A method for treating cystic fibrosis comprising administering to a warm-blooded animal a pharmacologically effective amount of a compound or a pharmaceutically acceptable salt thereof according to claim 1, which is a bis[5-(2-chlorobenzyl)-4-methoxy-6-methylpyrimidine-2-carboxylic acid]magnesium salt having a crystal form having main peaks at diffraction angles 2θ=11.82, 13.74, 14.26, 15.38, 21.56, 23.42, 24.14, 27.82, 28.72, and 31.06 in a powder X-ray diffraction pattern obtained by irradiation with copper Kα radiation (wavelength λ=1.54 angstroms).

24. A method for treating cystic fibrosis comprising administering to a warm-blooded animal a pharmacologically effective amount of a compound or a pharmaceutically acceptable salt thereof according to claim 1, which is a bis[5-(2-chlorobenzyl)-4-methoxy-6-methylpyrimidine-2-carboxylic acid]magnesium salt having a crystal form having main peaks at diffraction angles 2θ=5.18, 10.44, 18.98, 19.68, 22.36, 23.76, 26.34, and 27.96 in a powder X-ray diffraction pattern obtained by irradiation with copper Kα radiation (wavelength λ=1.54 angstroms).

25. A method for treating cystic fibrosis comprising administering to a warm-blooded animal a pharmacologically effective amount of a compound or a pharmaceutically acceptable salt thereof according to claim 1, which is 5-(2-chlorobenzyl)-4-methoxy-6-methylpyrimidine-2-carboxylic acid having a crystal form having main peaks at diffraction angles 2θ=6.68, 10.54, 16.16, 20.16, 21.22, 21.58, 24.20, 25.16, and 33.92 in a powder X-ray diffraction pattern obtained by irradiation with copper Kα radiation (wavelength λ=1.54 angstroms).

\* \* \* \* \*